(12) United States Patent
Zimmerman et al.

(10) Patent No.: US 8,877,970 B2
(45) Date of Patent: Nov. 4, 2014

(54) INHIBITORS OF CARBONIC ANHYDRASE IX

(75) Inventors: Craig Zimmerman, Topsfield, MA (US); John W. Babich, Cambridge, MA (US); John Joyal, Melrose, MA (US); Genliang Lu, Winchester, MA (US); Kevin P. Maresca, Tewksbury, MA (US); Chris Barone, Roxbury Crossing, MA (US)

(73) Assignee: Molecular Insight Pharmaceuticals, Inc., Tarrytown, NY (US)

(*) Notice: Subject to any disclaimer, the term of this patent is extended or adjusted under 35 U.S.C. 154(b) by 541 days.

(21) Appl. No.: 12/350,894

(22) Filed: Jan. 8, 2009

(65) Prior Publication Data

US 2009/0175794 A1 Jul. 9, 2009

Related U.S. Application Data

(60) Provisional application No. 61/020,043, filed on Jan. 9, 2008, provisional application No. 61/088,980, filed on Aug. 14, 2008, provisional application No. 61/142,002, filed on Dec. 31, 2008.

(51) Int. Cl.
| | |
|---|---|
| C07C 311/15 | (2006.01) |
| A61K 49/00 | (2006.01) |
| A61K 31/555 | (2006.01) |
| A61K 51/04 | (2006.01) |
| A61K 31/444 | (2006.01) |
| A61K 31/4192 | (2006.01) |
| A61K 31/18 | (2006.01) |

(52) U.S. Cl.
CPC ......... *A61K 51/0406* (2013.01); *A61K 51/0459* (2013.01); *A61K 51/0455* (2013.01); *A61K 31/555* (2013.01); *A61K 51/0453* (2013.01); *A61K 31/444* (2013.01); *A61K 51/0474* (2013.01); *A61K 51/0446* (2013.01); *A61K 31/4192* (2013.01); *A61K 31/18* (2013.01)
USPC ............ 564/85; 424/9.1; 424/1.65; 514/188; 514/185; 546/10; 534/10

(58) Field of Classification Search
None
See application file for complete search history.

(56) References Cited

U.S. PATENT DOCUMENTS

| | | |
|---|---|---|
| 2,730,456 A | 1/1956 | Green et al. |
| 2,730,457 A | 1/1956 | Green et al. |
| 2,800,457 A | 7/1957 | Green et al. |
| 3,625,214 A | 12/1971 | Higuchi |
| 4,272,398 A | 6/1981 | Jaffe |
| 4,798,734 A | 1/1989 | Kaneda |
| 4,906,474 A | 3/1990 | Langer et al. |
| 4,925,673 A | 5/1990 | Steiner et al. |
| 2003/0100594 A1 | 5/2003 | Masferrer et al. |
| 2003/0235843 A1 | 12/2003 | Babich et al. |
| 2004/0191174 A1 | 9/2004 | Linder et al. |
| 2004/0209921 A1 | 10/2004 | Bridger et al. |
| 2005/0038258 A1 | 2/2005 | Koike et al. |
| 2006/0057068 A1 | 3/2006 | Supuran et al. |
| 2008/0227962 A1 | 9/2008 | Mazzanti |
| 2009/0192182 A1 | 7/2009 | Kusumi et al. |
| 2010/0178246 A1 | 7/2010 | Babich et al. |
| 2010/0178247 A1 | 7/2010 | Babich et al. |
| 2010/0183509 A1 | 7/2010 | Babich et al. |

FOREIGN PATENT DOCUMENTS

| | | |
|---|---|---|
| CN | 102272102 | 12/2011 |
| EP | 0 544 412 A2 | 6/1993 |
| EP | 1 389 460 A1 | 2/2004 |
| EP | 1 550 657 A1 | 7/2005 |
| EP | 1 961 744 A1 | 8/2008 |
| JP | 04-342560 | 11/1992 |
| JP | 4342560 | 11/1992 |
| JP | 05-239046 | 9/1993 |
| JP | 08-282117 | 10/1996 |
| JP | 2002-506858 | 3/2002 |
| JP | 2005-519957 | 7/2005 |
| JP | 2005-539023 | 12/2005 |
| JP | 2006-509844 | 3/2006 |
| JP | 2007-523902 | 8/2007 |
| JP | 2007-524685 | 8/2007 |
| JP | 2010-523599 | 7/2010 |
| WO | WO-99/47507 | 9/1999 |

Radiochromatogram of the crude reaction for $^{99m}Tc(CO)_3$ MIP-1162
$R_t = 16.7$ min

| | | |
|---|---|---|
| WO | WO-03/013617 A2 | 2/2003 |
| WO | WO-03/077727 A2 | 9/2003 |
| WO | WO-2004/014352 A2 | 2/2004 |
| WO | WO-2004/048544 A2 | 6/2004 |
| WO | WO-2005/056520 A1 | 6/2005 |
| WO | WO-2005/079865 | 9/2005 |
| WO | WO-2006/080993 A1 | 8/2006 |
| WO | WO-2006/116736 | 11/2006 |
| WO | WO-2007/031640 | 3/2007 |
| WO | WO-2007/042504 | 4/2007 |
| WO | WO-2007/090461 A1 | 8/2007 |
| WO | WO-2007/148738 A1 | 12/2007 |
| WO | WO-2008/028000 A2 | 3/2008 |
| WO | WO-2008/058192 A2 | 5/2008 |
| WO | WO-2008/124703 A2 | 10/2008 |
| WO | WO-2009/076434 A1 | 6/2009 |
| WO | WO-2009/089383 A2 | 7/2009 |
| WO | WO-2010/036814 A1 | 4/2010 |
| WO | WO-2010/065899 A2 | 6/2010 |
| WO | WO-2010/065906 A2 | 6/2010 |

OTHER PUBLICATIONS

Dubois, L., et al., Imaging the hypoxia surrogate marker CA IX requries expression and catalytic activity for binding fluorescent sulfonamide inhibitors, 2007, Radiotherap and Oncology, vol. 83, pp. 367-373.*
Pastorekov, S., et al., Carbonic anhydrase IX (CA IX) as potential target for cancer therapy, 2004, Cancer Therapy, vol. 2, (19 pages).*
Steffens MG., et al., Targeting of renal cell carcinoma with iodine-131-labeled chimeric monoclonal antibody G250, 1997, J. Clin. Oncol., 15(4), 1529-37 (1 page abstract).*
EPA, Commonly Encountered Radionuclides, 2011, 2 pages.*
Alberto et al., "A Novel Organometallic Aqua Complex of Technetium for the Labeling of Biomolecules: Synthesis of [99Tc(OH2)3(CO3] [99mTcO4}- in Aqueous Solution and Its Reaction with a Bifunctional Ligand", Journal of American Chemical Society, American Chemical Society, vol. 120, No. 31, 1998, pp. 7987-7988.
Banerjee et al., "{RE(III)Cl3} Core Complexes with Bifunctional Single Amino Acid Chelates", Inorganic Chemistry, American Chemical Society, vol. 41, No. 22, 2002, pp. 5795-5802.
Banerjee et al., Bifunctional Single Amino Acid Chelates for Labeling of Biomolecules with the {Tc(CO)3} and {Re(CO)3} Cores. Crystal and Molecular Structures of [ReBr(CO)3(H2NCH2C5H4N)], [Re(CO)3{C5H4NCH2)2NH}Br, [Re(CO)3{C5H4NCH2)2NCH2CO2H}Br, [Re(CO)3{X(Y)NCH2CO2CH2CH3}Br(X=Y=2-pyridylmethyl; X=2-pyridylmethyl, Y=2-(1-methylimidazolyl)methyl,[ReBr(CO)3{C5H4NCH2)NH(CH2C4H3S)}], and [Re(CO)3{C5H4NCH2)N(CH2C4H3S)(CH2CO2)}], Inorganic Chemistry, vol. 41, No. 24, 2002, pp. 6417-6425.
Banerjee et al., "Synthesis and Evaluation of Technetium-99m- and Rhenium-Labeled Inhibitors of the Prostate-Specific Membrane Antigen (PSMA)", Journal of Medicinal Chemistry, vol. 15, pp. 4504-4517, 2008.
Benita, S. et al., "Characterization of Drug-Loaded Poly(d,l-lactide) Microspheres," Journal of Pharmaceutical Sciences, vol. 73, No. 12, Dec. 1984, pp. 1721-1724.
Berge et al., "Pharmaceuticals Salts," J. Pharm. Sci, vol. 66, No. 1, pp. 1-19., 1977.
Bonomi et al., Renato, "Phosphate Diester and DNA Hydrolysis by a Multivalent, Nanoparticle-Based Catalyst", Journal of the American Chemical Society, vol. 130, 2008, pp. 15744-15745.
Casini, Angela et al., "Carbonic Anhydrase Inhibitors: Synthesis of Water Soluble Sulfonamides Incorporating a 4-sulfamoylphenylmethylthiourea Scaffold, with Potent Intraocular Pressure Lowering Properties," Journal of Enzyme Inhibition and Medicinal Chemistry, 2002, vol. 17, No. 5, pp. 333-343.
Database Beilstein [Online]; Beilstein Institute for Organic Chemistry, 1958, Database Accession No. Citation No. 990210, XP002577062.
Deasy, Patrick et al., Microencapsulation and Related Drug Processes, 1984, School of Pharmacy, University of Dublin, Marcel Dekker, Inc.
Feng et al., Guoqiang, "Comparing a mononuclear Zn(II)complex with hydrogen bond donors with a dinuclear Zn(II) complex for catalysing phosphate ester cleavage", The Royal Society of Chemistry, 2006, pp. 1845-1847.

Greene, T. W. et al., Protective Groups in Organic Synthesis, Second Edition, Wiley, New York, 1991.
Greene, T. W. et al., Protective Groups in Organic Synthesis, Third Edition, Wiley, New York, 1999.
Gregoriadis, G., et al., Drug Carriers in Biology and Medicine, Chapter 14: Liposomes, pp. 287-341.
Henson et al., Mark J., "Resonance Raman Investigation of Equatorial Ligand Donor Effects on the Cu2O22 Core in End-On and Side-On u-Perozo-Dicopper(II) and Bis-u-oxo-Dicopper(III) Complexes", Journal of American Chemical Society, vol. 125, 2003, pp. 5186-5192.
International Search Report and Written Opinion mailed Oct. 14, 2010 in International Application No. PCT/US2009/066832.
International Search Report and Written Opinion mailed Dec. 28, 2010 in International Application No. PCT/US2009/066836.
Invitation to Pay Additional Fees mailed May 17, 2010 in International Application No. PCT/US2009/066832.
Invitation to Pay Additional Fees mailed May 17, 2010 in International Application No. PCT/US2009/066836.
Invitation to Pay Additional Fees mailed May 17, 2010 in International Application No. PCT/US2009/066842.
Jalil, R. et al., "Biodegradable poly(lactic acid) and poly(lactide-co-glycolide) microcapsules: problems associated with preparative techniques and release properties", J. Microencapsulation, 1990, vol. 7, No. 3, pp. 297-325.
Kojima et al., "Synthesis and Characterization of Mononuclear Ruthenium (III) Pyridylamine Complexes and Mechanistic Insights into Their Catalytic Alkane Functionalization with m-Chloroperbenzoic Acid", Chemistry, vol. 13, 2007, pp. 8212-8222.
Krebs, H.A., "Inhibition of Carbonic Anhydrase by Sulphonamides," The Biochemical Journal, vol. 43, 1948, pp. 525-528.
Kularatne, S.A. et al., "Design, Synthesis, and Preclinical Evaluation of Prostate-Specific Membrane Antigen Targeted 99mTc-Radioimaging Agents," Molecular Pharmaceutics, vol. 6, No. 3, pp. 790-800, Apr. 11, 2009.
Lewis et al., "Maleimidocysteineamido-DOTA Derivatives: New Reagents for Radiometal Chelate Conjugation to Antibody Sulfhydryl Groups Undergo pH-Dependent Cleavage Reactions", Bioconjugate Chemistry, American Chemical Society, vol. 9, No. 1, 1998, pp. 72-86.
Lim, Franklin et al, "Microencapsulation of Living Cells and Tissues," Journal of Pharmaceutical Sciences, Apr. 1981, vol. 70, No. 4, pp. 351-354.
Mathiowitz, E. et al., "Mophology of Polyanhydride Miscrosphere Delivery Systems," Scanning Microscopy, 1990, vol. 4, No. 2, pp. 329-340.
Mathiowitz, E. et al., "Polyanhydride Microspheres as Drug Carriers. II. Microencapsulation by Solvent Removal," Journal of Applied Polymer Science, 1988, vol. 35, pp. 755-774.
Nakano, M. et al., "Sustained Urinary Excretion of Sulfamethizole Following Oral Administration of Enteric Coated Microcapsules in Humans," International Journal of Pharmaceutics, 1980, vol. 4, pp. 291-298.
Nonat et al., Aline, "Structure, Stability, Dynamics, High-Field Relaxivity and Ternary-Complex Formation of a New Tris(aquo) Gadolinium Complex", Chemistry, vol. 13, 2007, pp. 8489-8506.
Roy et al, Bidham C., "Two-Prong Inhibitors for Human Carbonic Anhydrase II", Journal of American Chemical Society, vol. 126, 2004, pp. 13206-13207.
Salib, N. et al., "Utilization of Sodium Alginate in Drug Microencapsulation," Pharm. Ind., vol. 40, No. 11a, 1978, pp. 1230-1234.
Sawhney, A. et al., "Bioerodible Hydrogels Based on Photopolymerized Poly(ethylene glycol)-co-poly(a-hydroxy acid) Diacrylate Macromers," Macromolucules, vol. 26, 1993, pp. 581-587.
Thallaj, Nasser K., "A Ferrous Center as Reaction Site for Hydration of a Nitrile Group into a Carboxamide in Mild Conditions", Journal of American Chemical Society, vol. 130, 2007, pp. 2414-2415.
Yao, Zhen et al., Synthesis of Porphyrins Bearing 1-4 hydroxymethyl Groups and other One-carbon oxygenic Substituents in Distinct Patterns, Tetrahedron, vol. 63, 2007, pp. 10657-10670.
Cecchi, et al., "Carbonic Anhydrase Inhibitors. Design of Fluorescent Sulfonamides as Probes of Tumor-assoicated Carbonic Anhydrase IX that Inhibit Isozyme IX-Mediated Acidification of Hypoxic Tumores," Journal of Medicinal Cheimistry, vol. 48, No. 15, Jul. 2005, pp. 4834-4841.

Thiry, et al., "Targeting Tumor-Associated Carbonic Anhydrase IX in Cancer Therapy," Trends in Pharmacological Sciences, vol. 27, No. 11, Nov. 2006, pp. 566-573.
PCT International Search Report corresponding to PCT/US2009/030487, dated Jun. 26, 2009; 8 pages.
PCT Written Opinion corresponding to PCT/US2009/030487, dated Jun. 26, 2009; 15 pages.
Hanada et al., "Preparation of 2,8-diazaspiro[4.5]decane containing bis(imidazol-2-ylmethyl_amines as CXCR4 antagonists for treatment of inflammation and immune disease", caplus an 2008:159048, 5 pages.
Kusumi et al., "Preparation of heterocycle compounds having (un)protected acidic group as CXCR4 antagonists", caplus an 2007:1332283, 8 pages.
Non-final Office Actin received for U.S. Appl. No. 12/631,312 dated Mar. 6, 2012.
Notice of Allowance received for U.S. Appl. No. 12/631,337 dated Mar. 15, 2012.
Notice of Allowance received for U.S. Appl. No. 12/631,343 dated Mar. 12, 2012.
Saitou et al., "Preparation of N-arylmethyl or N-hererocyclylmethyl-N-(imidazol-2-ymethyl)amines as antagonists of chemokine receptor CXCR4", caplus an 2005:1004718, 6 pages.
Non-Final Office Action mailed Feb. 27, 2013, in U.S. Appl. No. 12/631,312.
Office Action in EP Appln No. 09 701 293.4 dated Dec. 20, 2012.
Banerjee, A. et al. "Inhibition of matrix metalloproteinase-9 by "multi-prong" surface binding groups", Chem. Commun., 2005, No. 20, pp. 2549-2551.
Communication—EP Search Report in EP Appln No. 13195617.9 dated Jan. 31, 2014.
Communication pursuant to Article 94(3) EPC in EP Appln No. 09 775 430.3 dated Aug. 8, 2013.
De Leval, et al. "Carbonic Anhydrase Inhibitors: Synthesis and Topical Intraocular Pressure Lowering Effects of Fluorine-Containing Inhibitors Devoid of Enhanced Reactivity", Journal of Medicinal Chemistry, 2004, vol. 47, No. 11, pp. 2796-2804.
Decision of Rejection in CN Appln No. 200980107793.4 dated Feb. 12, 2014.
Dubenko, et al. "Thiocarbanilide Derivatives. IV. Synthesis of unsymmetrical monohalothiocarbanilides", Zhurnal Obshchei Khimii, 1962, vol. 32, pp. 626-628.
Gallagher, J. et al. "Protease Activity of 1,10-Phenanthroline-Copper(I). Targeted Scission of the Catalytic Site of Carbonic Anhydrase", Biochemistry, 1998, vol. 37, pp. 2096-2104.
Gracheva, et al. "Chemical changes during beta-decay of bismuth-210 (RaE) entering into the composition of tris(p-sulfamoylphenyl)bismuth", STN on the Web, File CAPLUS, 1968, vol. 83, p. 305.
Office Action—Final—Reasons for Rejection in JP Appln No. 2010-542351 dated Apr. 1, 2014.
Office Action in CN Appln No. 200980153877.1 dated Sep. 17, 2013.
Office Action in CN Appln No. 200980153878.6 dated Mar. 7, 2014.
Office Action in JP Appln No. 2010-542351 dated Aug. 20, 2013.
Office Action in JP Appln No. 2011-539757 dated Dec. 24, 2013.
Rami, M. et al. "Carbonic Anhydrase Inhibitors: Design of Membrane-Impermeant Copper(II) Complexes of DTPA-, DOTA-, and TETA-Tailed Sulfonamides Targeting the Tumor-Associated Transmembrane isoform IX", Chemmedchem, 2008, vol. 3, pp. 1780-1788.
Shah, et al. "Benzylthioureas, Part III", Journal of Indian Chemical Society, 1959, vol. 36, No. 7, pp. 507-508.
Singh, et al. "The Enzyme-Inhibitor Approach to Cell-Selective Labelling-II. In Vivo Studies with pIBS in Small Animals and Man", Applied Radiation and Isotopes, 1991, vol. 42, No. 3, pp. 261-267.
Thiry, et al. "Indanesulfonamides as Carbonic Anhydrase Inhibitors. Toward Structure-Based Design of Selective Inhibitors of the Tumor-Associated Isozyme CA IX", Journal of Medicinial Chemistry, 2006, vol. 49, No. 9, pp. 2743-2749.
Viswanathan, et al. "Metanilamide-Substituted Thiourea Derivatives", Current Science, 1952, No. 12, pp. 342-343.
Communication received in EP Appln. No. 09701293.4 dated May 3, 2012.
Database WPI, Week 199302, Thomas Scientific, London, GB; AN 1993-014070 & JP4342560 A (Daiichi Radioisotope Kenkyusho)Nov. 30, 1992 (English Abstract of JP4342560).
Database CAPLUS, [Online] Nov. 30, 1992, Karube Yoshiharu et al: "Preparation of sulfanilamide derivatives and their technetium complexes as radiodiagnostic agents", XP002577771, retrieved from CAPLUS Database accession No. 1993-427837.
Final Office Action received for U.S. Appl. No. 12/631,312 dated Sep. 6, 2012.
Kojima, "Synthesis and Characterization of Mononuclear Ruthenium(III) Pyridylamine Complexes and Mechanistic Insights into Their Catalytic Alkane Functionalization with m-Chloroperbenzoic Acid", Chemistry, 2007, vol. 13, No. 29, pp. 8212-8222.
Notice of Reasons for Rejection in JP Appln No. JP 2011-539752 dated Mar. 25, 2014.
Office Action in CN Appln No: 200980153877.1 dated Apr. 8, 2014.

* cited by examiner (Continued)

*Primary Examiner* — Yate K Cutliff

(74) *Attorney, Agent, or Firm* — Gilberto M. Villacorta; Jeffrey R. Lomprey; Foley & Lardner LLP

(57) ABSTRACT

Novel radiopharmaceuticals that are useful in diagnostic imaging and therapeutic treatment of disease characterized by over expression of CA-IX comprise a complex that contains a sulfonamide moiety which is capable of binding the active catalytic site of CA-IX, and a radionuclide adapted for radioimaging and/or radiotherapy:

(I)
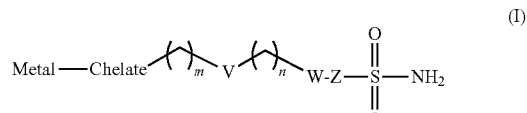

(II)
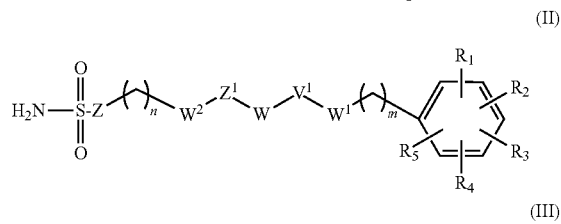

(III)
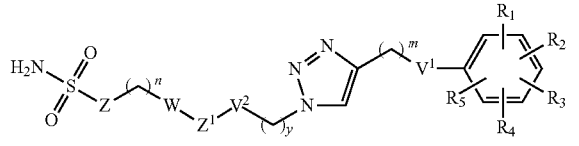

(IV)
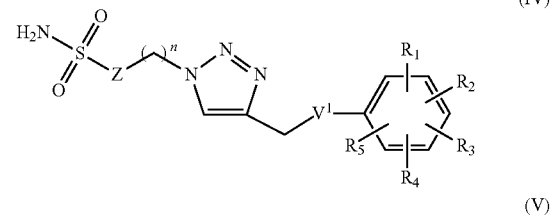

(V)
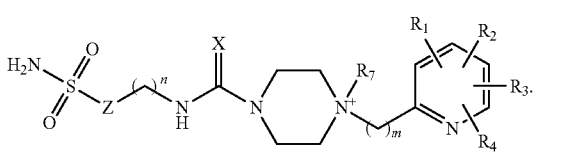

9 Claims, 5 Drawing Sheets

Radiochromatogram of the crude reaction of I-131 NaI with the 4-trimethylstannane of MIP-1222

UV-vis chromatogram of the reference standard MIP-1222 eluting at 13 minutes

INHIBITORS OF CARBONIC ANHYDRASE IX

CROSS-REFERENCE TO RELATED APPLICATIONS

This application claims priority to U.S. provisional application No. 61/020,043 filed Jan. 9, 2008; U.S. provisional application No. 61/088,980 filed Aug. 14, 2008 and U.S. provisional application No. 61/142,002 filed Dec. 31, 2008, the disclosures of which are incorporated herein by reference.

TECHNICAL FIELD

This invention relates in general to radiopharmaceuticals for diagnostic imaging and therapeutic treatment of diseases, and in particular, to radiolabeled inhibitors of carbonic anhydrase IX (CA-IX).

BACKGROUND

The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins allow the use of noninvasive imaging techniques, such as molecular imaging or nuclear medicine, for detecting the presence and quantity of tumor associated proteins, thereby providing vital information related to the diagnosis and extent of disease, prognosis and therapeutic management options. In addition, as radiopharmaceuticals can be prepared that are not only capable of imaging disease but also delivering a therapeutic radionuclide to the diseased tissue, therapy, in particular cancer therapy, can be realized. The selective expression of CA-IX on tumors in response to hypoxia makes it an attractive target to exploit for noninvasive imaging as well as targeted radiotherapy.

It is known that to grow beyond more than a few millimeters in diameter, tumor micrometastasis need to obtain a supply of oxygen to sustain the high metabolic rate characteristic of rapid growth, and do so by inducing the formation of new blood vessels. The distance that tumor cells reside from blood vessels is inversely proportional to the oxygen pressure of the tumor. Even when angiogenesis occurs and a blood supply is established, the less vascular interior region of the growing tumor mass remains hypoxic and eventually undergoes necrosis.

Hypoxia is associated with a poor response to radiation therapy, and leads to tumor resistance. Since oxygen is necessary for the cytotoxic actions of free radicals generated by radiation, higher, often incompatible, levels of radiation are required to promote damage to the tumor. Therefore, there is a need for non-invasive techniques to stratify patients based on cancer hypoxia who are not expected to respond to radiation therapy because of low oxygen, and who may be candidates for alternative hypoxia-activated chemotherapies that are becoming available. As hypoxia constitutes a major difference between the tumor and normal tissues, it can be exploited for the development of tumor specific probes.

Hypoxia is a potent stimulus for the expression of specific genes, several which function to trigger vasculogenesis and therefore supply oxygen to the tumor, increase metabolism to increase the oxygen extraction factor, and promote a favorable environment for tumor growth. The activation of hypoxia inducible genes is in part mediated by a transcription factor, HIF-1α. Under normoxic conditions, HIF-1α is hydroxylated on proline residues that reside in the oxygen induced degradation domain of the protein by proline hydroxylase. Hydroxyproline facilitates binding of Von-Hippel-Lindau Factor (VHL), a tumor suppressor that, when bound, promotes the ubiquitination and degradation of HIF-1α. During hypoxia, proline hydroxylase is inhibited, and VHL no longer binds HIF-1α; the now stabilized HIF-1α translocates to the nucleus and associates with HIF-1α. This heterodimeric transcription factor then binds to HIF-1 responsive DNA sequences in the promoter region of target genes including the carbonic anhydrase isoform CA-IX, as well as VEGF, erythropoietin, and glucose transporters.

Carbonic anhydrases are a family of enzymes comprised of 16 isozymes that catalyze the reaction: $CO_2 + H_2O \leftrightarrow HCO_3^- + H^+$, and therefore play an important role in pH regulation. Specific isozymes are found either in the cytosol, anchored to the membrane, within the mitochondria, or secreted from the cell. The well studied constitutively expressed isozyme, carbonic anhydrase II, is found in the cytosol of most cell types, and is the primary isoform responsible for the regulation of intracellular pH.

CA-IX is a membrane-anchored isoform of the enzyme with its catalytic domain in the extracellular space. It has a limited tissue distribution and is found at low levels primarily in the gastrointestinal tract. The expression of CA-IX is under the control of HIF-1α, and this isozyme is highly expressed in tumors cells exposed to hypoxia both in vitro and in vivo. Increased CA-IX expression has been detected in carcinomas of the cervix, ovary, kidney, esophagus, lung, breast, and brain. CA-IX has been reported to promote extracellular acidification. The low extracellular pH as a result of the activity of CA-IX leads to tumorigenic transformation, chromosomal rearrangements, extracellular matrix breakdown, migration and invasion, induction of growth factors, protease activation, and chemoresistance.

CA-IX has been shown by immunohistochemistry and by a variety of molecular techniques to be correlated with tumor progression and poor survival, and has been proposed as a clinical diagnostic and prognostic marker for breast, renal and non-small cell lung cancers. A chimeric $^{124}$I-labeled anti-CA-IX antibody G250 is currently undergoing clinical trials for the detection of clear cell renal carcinoma, validating CA-IX as a cancer target.

While intact antibodies such as G250 offer potential for tumor radiotargeting, long circulating half-life and poor tissue penetrability limit their effectiveness as radiodiagnostic and radiotherapeutic agents. A variety of biologically active molecules have been exploited as carriers for the radionuclides. However, small molecules offer significant advantages over antibodies and proteins. In general, the affinity of small molecules for their receptors is similar to that of monoclonal antibodies. Small molecules by definition exhibit enhanced diffusibility to the extravascular space, faster blood clearance resulting in lower background radiation. In addition, the opportunity to synthesize analogs exhibiting diverse chemical properties allows alteration of binding affinity and pharmacokinetics.

Currently, many small molecule inhibitors for CA-IX show undesired side effects due to inhibition of other CA isozymes present in the target organ. Due to the extracellular location of CA-IX, the applicants have discovered that membrane-impermeant CA inhibitors would inhibit selectively only membrane-associated CA isozymes, thus potentially reducing undesired side effects that may arise from inhibition of other, including non-membrane-associated, CA isozymes.

SUMMARY

The invention provides novel radiopharmaceuticals that are useful in diagnostic imaging and therapeutic treatment of disease which is characterized by overexpression of CA-IX. The radiopharmaceuticals comprise a complex or compound that contains a sulfonamide moiety which is capable of binding the active catalytic site of CA-IX, and a radionuclide adapted for radioimaging and/or radiotherapy.

In one aspect, a complex of formula I, its stereoisomer or pharmaceutically acceptable salt is provided:

$$\text{Metal—Chelate} \overset{}{\underset{m}{\longleftarrow}} V \overset{}{\underset{n}{\longleftarrow}} W\text{-}Z\overset{O}{\underset{O}{-\overset{\|}{\underset{\|}{S}}}}\text{—NH}_2 \tag{I}$$

wherein:

V is a bond, O, C=O, C(=X)—NH, a group of

<span style="display:inline-block;">W ~~~~ C(O)CH₂CH₂C(O)NH</span> or a group of

U—NH—C(X)—NH wherein X is O or S; U is a bond or a group of (O—CH₂—CH₂—O)$_p$—CH₂—CH₂ wherein p is an integer ranging from 1 to 3;

W is a bond, O, or NH;

Z is an aromatic, bicyclic aromatic, heteroaromatic, bicyclic heteroaromatic or heterocyclic ring;

m is an integer ranging from 0 to 8;

n is an integer ranging from 0 to 8;

Metal represents a metallic moiety comprising a radionuclide; and

Chelate represents a chelating moiety that coordinates with said radionuclide to form said complex.

In another aspect, a compound of general formula II, its stereoisomer or pharmaceutically acceptable salt is provided:

$$\text{(II)}$$

wherein:

$V^1$ is selected from the group consisting of a bond, O, NH, O—(CH$_2$—CH$_2$—O)$_q$, a group of

[structure showing iminodiacetic acid / EDTA-like linker with CO₂H, HO₂C groups]

a group of CHR$_6$—CO or CHR$_6$—CO—NH—CHR$_6$—CO wherein R$_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

W is a bond, O, or NH;

$W^1$ and $W^2$ are independently a bond, NH, C=X, or a group of

[structure: —NH—C(=X)—NH—]

wherein X is O or S;

Z is an aromatic, bicyclic aromatic, heteroaromatic, bicyclic heteroaromatic or heterocyclic ring;

$Z^1$ is a bond, aromatic, bicyclic aromatic, heteroaromatic, bicyclic heteroaromatic or heterocyclic ring;

m is an integer ranging from 0 to 8;

n is an integer ranging from 0 to 8;

q is an integer ranging from 1 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In a still another aspect, a compound of general formula III or its stereoisomer or pharmaceutically acceptable salt is provided:

$$\text{(III)}$$

wherein:

$V^1$ and $V^2$ are independently selected from the group consisting of a bond, O, NH, O—(CH$_2$—CH$_2$—O)$_q$, a group of

[structure showing iminodiacetic acid / EDTA-like linker with CO₂H, HO₂C groups]

a group of CHR$_6$—CO or CHR$_6$—CO—NH—CHR$_6$—CO wherein R$_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

$W^1$ is a bond, NH, C=X, or a group of

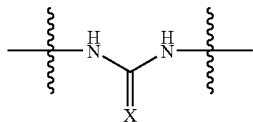

wherein X is O or S;

Z, is an aromatic, bicyclic aromatic, heteroaromatic, bicyclic heteroaromatic or heterocyclic ring;

$Z^1$ is a bond, aromatic, bicyclic aromatic, heteroaromatic, bicyclic heteroaromatic or heterocyclic ring;

m is an integer ranging from 0 to 8;

n is an integer ranging from 0 to 8;

q is an integer ranging from 1 to 6;

y is an integer ranging from 0 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In a still another aspect, a compound of formula IV, its stereoisomer or pharmaceutically acceptable salt is provided:

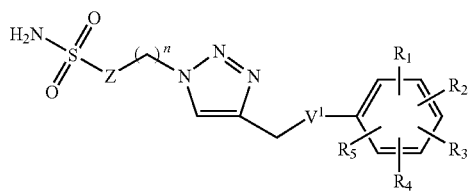

(IV)

wherein:

$V^1$ is selected from the group consisting of a bond, O, NH, O—(CH$_2$—CH$_2$-O)$_q$, a group of

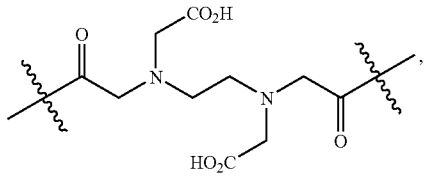 [SMILES: *C(=O)CN(CCN(CC(*)=O)CC(=O)O)CC(=O)O]

a group of CHR$_6$—CO or CHR$_6$—CO—NH—CHR$_6$—CO wherein R$_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

Z is an aromatic, bicyclic aromatic, heteroaromatic, bicyclic heteroaromatic or heterocyclic ring;

n is an integer ranging from 0 to 8;

q is an integer ranging from 1 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In a further aspect, a compound of formula V, its stereoisomer or pharmaceutically acceptable salt is provided:

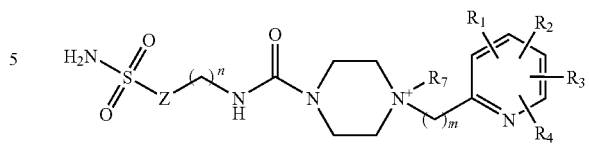

(V)

wherein:

X is O or S;

m is an integer ranging from 0 to 8;

n is an integer ranging from 0 to 8;

$R_1$, $R_2$, $R_3$, and $R_4$ are independently selected from the group consisting of hydrogen, carboxyl, halogen, alkyl, alkoxy, and substituted or unsubstituted amino wherein at least one halogen is selected; and $R_7$ is H or lower alkyl.

In another aspect, a method of imaging tissue of a mammal which expresses CA-IX is provided which comprises administering to the mammal an effective amount of a radiolabeled compound or complex that selectively inhibits CA-IX. In a preferred embodiment, the radiolabeled complex includes a radionuclide-containing chelate derivative of a CA-IX inhibitor. In another preferred embodiment, the radiolabeled compound includes a radioactive halogenated derivative of a CA-IX inhibitor. In a particular preferred embodiment, an effective amount of a complex or compound represented by formula I, II, III, IV and V and attendant definitions is administered to the mammal. Moreover, the invention includes a method of imaging a mammal suspected of harboring a tumor that expresses CA-IX comprising administering to said mammal an effective amount of a radiolabeled CA-IX inhibitor.

In a further aspect, the invention provides a method of treating a mammal suffering a disease which is characterized by over expression of CA-IX. The method comprises administering to the mammal a therapeutically effective amount of a radiolabeled CA-IX inhibitor, preferably a radionuclide-containing chelate derivative or a radioactive halogen derivative, and more preferably a complex or compound represented by formulas I, II, III, IV and V and attendant definitions. Moreover, the invention encompasses a method of treating a mammal suspected of harboring a tumor that expresses CA-IX comprising administering to said mammal an effective amount of a radiolabeled CA-IX inhibitor.

In still another aspect, a kit is provided comprising the subject complexes or compounds and a pharmaceutically acceptable carrier, and optionally instructions for their use. Uses for such kids include therapeutic management and medical imaging applications.

BRIEF DESCRIPTION OF THE DRAWINGS

These and various other features and advantages of the present invention will become better understood upon reading of the following detailed description in conjunction with the accompanying drawings and the appended claims provided below, where:

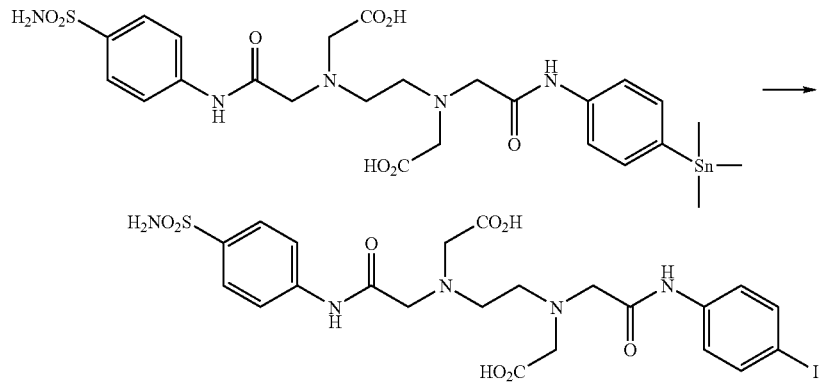

Figure 5:
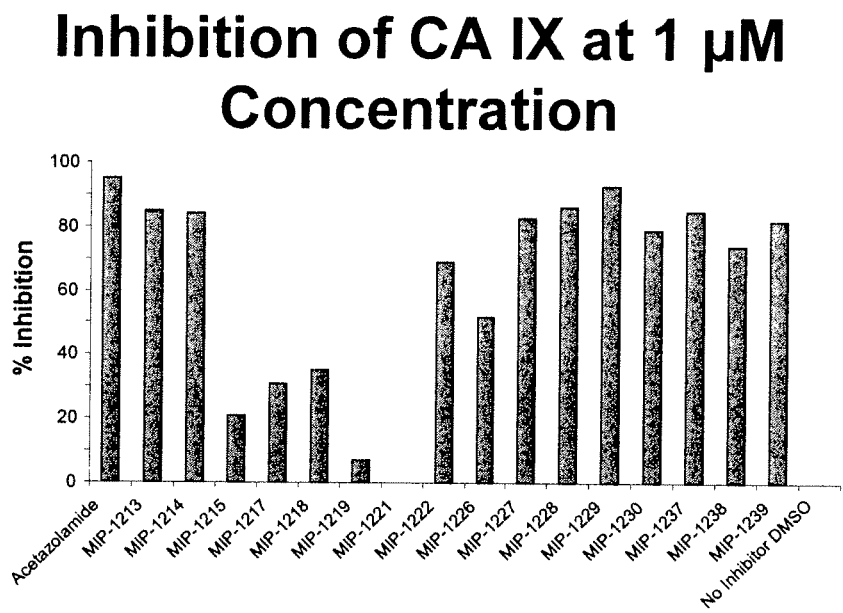

FIG. 5 is a graph illustrating percent inhibition of CA-IX activity by some compounds in accordance with several embodiments of the present invention.

DETAILED DESCRIPTION OF PREFERRED EMBODIMENTS

Various embodiments of the invention are described hereinafter. It should be noted that the specific embodiments are not intended as an exhaustive description of the invention or as a limitation on the scope of the invention. One aspect described in conjunction with a particular embodiment of the present invention is not necessarily limited to that embodiment and can be practiced with any other embodiment(s) of the invention.

As used herein, the following definitions of terms shall apply unless otherwise indicated.

"Complex" refers to a compound formed by the union of one or more electron-rich and electron-poor molecules or atoms capable of independent existence with one or more electronically poor molecules or atoms, each of which is also capable of independent existence.

"Ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

"Chelate" or "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

"Radionuclide" refers to molecule that is capable of generating a detectable image that can be detected either by the naked eye or using an appropriate instrument, e.g. positron emission tomography (PET) and single photon emission tomography (SPECT). Radionuclides useful within the present disclosure include penetrating photon emitters including gamma emitters and X-ray emitters. These rays accompany nuclear transformation such as electron capture, beta emission and isomeric transition. Radionuclides useful include those with photons between 80 and 400 keV and positron producers, 511 keV annihilation photons and acceptable radiation doses due to absorbed photons, particles and half life. Radionuclides include radioactive isotopes of an element. Examples of radionuclides include $^{123}$I, $^{125}$I, $^{99m}$Tc, $^{18}$F, $^{68}$Ga, $^{62}$Cu, $^{111}$In, $^{131}$I, $^{186}$Re, $^{188}$Re, $^{90}$Y, $^{212}$Bi, $^{211}$At, $^{89}$Sr, $^{166}$Ho, $^{153}$Sm, $^{67}$Cu, $^{64}$Cu, $^{100}$Pd, $^{212}$Pb, $^{109}$Pd, $^{67}$Ga, $^{94}$Tc, $^{105}$Rh, $^{95}$Ru, $^{177}$Lu, $^{170}$Lu $^{11}$C, and $^{76}$Br.

"Coordination" refers to an interaction in which one multi-electron pair donor coordinatively bonds (is "coordinated") to one metal ion.

"Tether" refers to a chemical linking moiety between a metal ion center and another chemical moiety.

"Lewis base" and "Lewis basic" are art-recognized and generally refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O_2^-$). In certain, less common circumstances, a Lewis base or ligand may be positively charged. A Lewis base, when coordinated to a metal ion, is often referred to as a ligand. Further description of ligands relevant to the present invention is presented herein.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the E and Z isomers or mixtures of these isomers. "Lower alkyl" refers to monovalent saturated aliphatic hydrocarbyl groups having from 1 to 4 carbon atoms. Alkyl or lower alkyl may be substituted or unsubstituted.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH) and propargyl (—$CH_2$C≡CH).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Amino acid" refers to all compounds, whether natural, unnatural or synthetic, which include both an amino functionality and an acid functionality, including amino acid analogs and derivatives.

"Carboxy" or "carboxyl" refers to —COOH or salts thereof.

"Sulfonamide" refers to —S(=O)$_2$—$NH_2$.

"Amino" refers to the group —$NH_2$. "Cyano" refers to the group —CN. "Halo" or "halogen" refers to fluoro, chloro, bromo and iodo and preferably is fluoro or chloro. "Carbonyl" refers to the divalent group —C(O)— which is equivalent to —C(=O)—. "Nitro" refers to the group —$NO_2$. "Oxo" refers to the atom (=O). "Sulfonyl" refers to the divalent group —S(O)$_2$—. "Thiol" refers to the group —SH. "Thiocarbonyl" refers to the divalent group —C(S)— which is equivalent to —C(=S)—. "Hydroxy" or "hydroxyl" refers to the group —OH.

"Heteroatom" refers to an atom of any element other than carbon or hydrogen. Exemplary heteroatoms are boron, nitrogen, oxygen, phosphorus, sulfur and selenium.

"Halogen" refers to F, Cl, Br and I and their corresponding radionuclides.

"Haloalkyl" refers to alkyl groups substituted with 1 to 5, 1 to 3, or 1 to 2 halo groups, wherein alkyl and halo are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" refers to the group —C(O)$NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)$NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$$NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Bicyclic aromatic" refers to a bicyclic structure with at least one aromatic ring, e.g.,

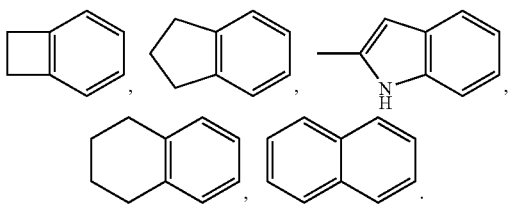

"Bicyclic heteroaromatic" refers to a bicyclic structure with at least one heteroaromatic ring, e.g.,

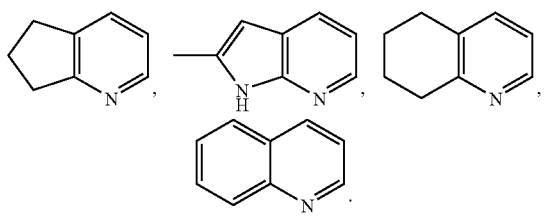

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl, thiadiazolyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, thiadiazolyl and furanyl.

"Heteroaromatic" refer to optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, thiadiazole or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, 1,3,4-thiadiazole, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Stereoisomer" or "stereoisomers" refer to compounds that differ in the chirality of one or more stereocenters. Stereoisomers include enantiomers and diastereomers.

The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

"Pharmaceutically acceptable salts" refers to relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1-19 (1977).

The phrase "pharmaceutically acceptable carrier" is art-recognized, and includes, for example, pharmaceutically acceptable materials, compositions or vehicles, such as a liquid or solid filler, diluent, solvent or encapsulating material, involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "therapeutically effective amount" refers to a therapeutically effective, CA-IX inhibitive amount of a complex or compound of formula I, II, III or IV. A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the use of concomitant medication; and other relevant circumstances.

"Subject" refers to mammals and includes humans and non-human mammals.

"Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease.

The invention contemplates the use of radiolabeled derivatives of CA-IX inhibitors in diagnostic imaging and treatment of diseases which are characterized by expression of CA-IX.

The invention is generally based on identification of compounds that afford affinity and/or selectivity for CA-IX. In some aspects, compounds that contain an arylsulfonamide moiety capable of binding zinc in the CA-IX active site are incorporated with a chelate-metallic moiety comprising a radionuclide. Due to its bulky structure, the formed complex containing the arylsulfonamide moiety is cell impermeant, thus render it selective for extracellular CA-IX over other carbonic anhydrases, most notably the constitutively expressed cytosolic carbonic anhydrase CA-II. The complex may be prepared containing charges, which provide additional hindrance for the complex to enter the cell. The radionuclide incorporated into the complex is adapted for radioimaging and/or radiotherapy.

In one aspect, the invention provides a complex of formula I, its stereoisomer or pharmaceutically acceptable salt:

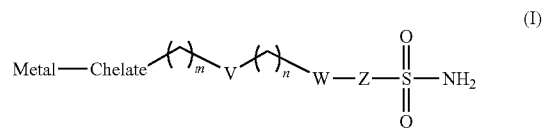

wherein:
V is a bond, O, C=O, C(=X)—NH, a group of

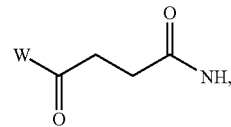

or a group of

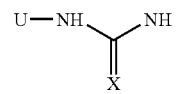

wherein X is O or S; U is a bond or a group of (O—$CH_2$—$CH_2$—O)$_p$—$CH_2$—$CH_2$ wherein p is an integer ranging from 1 to 3;
W is a bond, O, or NH;
Z is an aromatic, bicyclic aromatic, heteroaromatic, bicyclic heteroaromatic or heterocyclic ring;
m is an integer ranging from 0 to 6;
n is an integer ranging from 0 to 6;
Metal represents a metallic moiety comprising a radionuclide; and
Chelate represents a chelating moiety that coordinates with said radionuclide to form said complex.

In some embodiments, Metal represents a metallic carbonyl ligand comprising a radionuclide. Exemplary radionuclides include technetium (Tc), rhenium (Re), yttrium (Y), indium (In), and copper (Cu). In some embodiments, the radionuclide is a low oxidization state metal. Examples of low oxidization state metals include metals with an oxidation state less than or equal to about 4, for example Tc(I), Re(I), and Cu(0). By way of example, in some embodiments, Metal represents a $^{185/186/188}$Re-carbonyl or $^{185/186/188}$Re-tricarbonyl ligand. In some preferred embodiments, Metal represents a $^{99m}$Tc-carbonyl ligand or a $^{99m}$Tc-tricarbonyl ligand.

Any suitable chelating moiety may be used to provide a covalent or other association with a radionuclide. Examples of chelating agents include a substituted or unsubstituted $N_2S_2$ structure, a $N_4$ structure, an isonitrile, a hydrazine, a triaminothiol, a chelating agent with a hydrazinonicotinic acid group, a phosphorus group, phosphinothiols, thioesters, thioethers, a picolineamine monoacetic acid, a pyridine or bipyridyl based compound, and a substituted or unsubstituted cyclopentadienyl. By way of example, suitable chelating agents include, but are not limited to, tetra-azacyclododecanetetra-acetic acid (DOTA), diethylenetriaminepentaacetic acid (DTPA), bis(pyridin-2-ylmethyl)amine (DPA), quinolinemethylamino acetic acid (QAA), bis(isoquinolinemethyl)amine, bis(quinolinemethyl)amine (DQA), pyridine-2-ylmethylamino acetic acid (PAMA), isoquinolin-3-ylmethylamino acetic acid, bis(thiazol-2-ylmethyl)amine (DTK), and thiazol-2-ylmethylamino acetic acid (MTMA), bis(N-carboxymethylimidazoylamine) (DCMI) bis(N-1,1- dimethoxyethylimidazoylamine) (DMEI), bis(N-methylimidazoylamine) (DMI): bis(N-hydroxyethylimidazoylamine) (DHI).

The distance between the Metal-Chelate moiety and the arylsulfonamide moiety of the complex represented by formula I can be varied by altering the tether and/or expanding the length of the tether between them to modify the affinity and selectivity of the complex for CA-IX. The pharmacokinetics properties of the complex can also be modified by incorporating heteroatoms into the tethers. The following structures represented by formulas I-a to I-h are some exemplary embodiments with different tethers and/or the length of tethers. To facilitate description, the complexes are described below with embodiments where the Metal-Chelate moiety has the following structure:

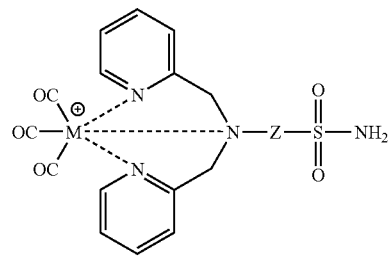

where M is technetium (Tc) or rhenium (Re). It will be appreciated that the claimed invention is not so limited and other Metal-Chelate structures are anticipated within the scope of the invention as described above.

In some embodiments, the complex has the structure of formula I-a where M is technetium (Tc) or rhenium (Re); and Z is an aromatic, bicyclic aromatic, heteroaromatic, bicyclic heteroaromatic or heterocyclic ring:

(I-a)

In some embodiments, the complex has the structure of formula I-b where M is technetium or rhenium; W is a bond, O or NH; Z is an aromatic, bicyclic aromatic, heteroaromatic, bicyclic heteroaromatic or heterocyclic ring and m is an integer ranging from 1 to 6:

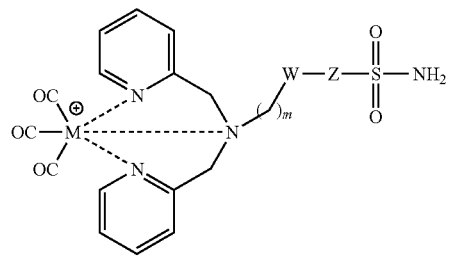

In some embodiments, the complex has the structure of formula I-c where M is technetium or rhenium; W is a bond, O or NH; Z is an aromatic, bicyclic aromatic, heteroaromatic, bicyclic heteroaromatic or heterocyclic ring and n is an integer ranging from 0 to 3:

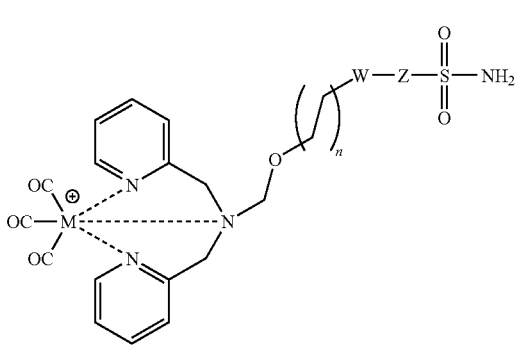

In some embodiments, the complex has the structure of formula I-d where M is technetium or rhenium; Z is an aromatic, bicyclic aromatic, heteroaromatic, bicyclic hetero aromatic or heterocyclic ring; m is an integer ranging from 1 to 6, and n is an integer ranging from 0 to 6:

(I-d)

In some embodiments, the complex has the structure of formula I-e where M is technetium or rhenium; Z is an aromatic, bicyclic aromatic, heteroaromatic, bicyclic hetero aromatic or heterocyclic ring; m is an integer ranging from 1 to 6, and n is an integer ranging from 1 to 6:

(I-e)

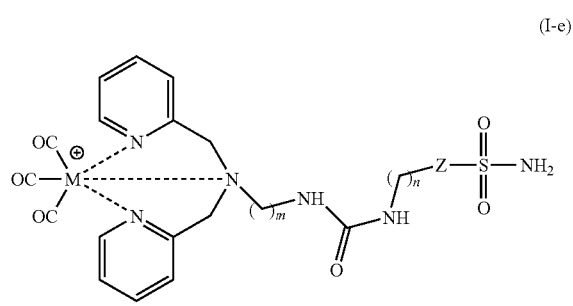

In some embodiments, the complex has the structure of formula I-f where M is technetium or rhenium; Z is an aromatic, bicyclic aromatic, heteroaromatic, bicyclic hetero aromatic or heterocyclic ring; p is an integer ranging from 1 to 3; and n is an integer ranging from 1 to 6:

(I-f)

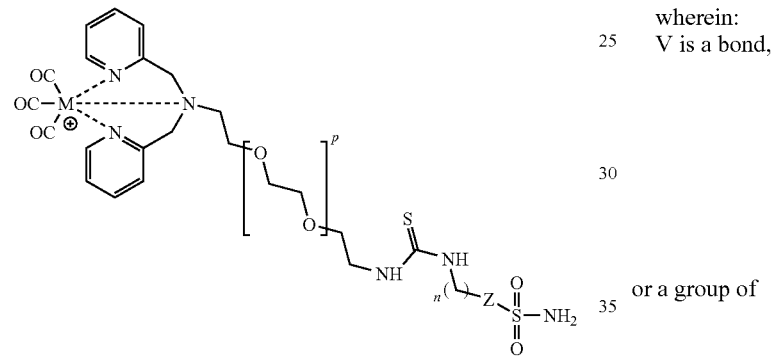

In some embodiments, the complex has the structure of formula I-g where M is technetium or rhenium; Z is an aromatic, bicyclic aromatic, heteroaromatic, bicyclic hetero aromatic or heterocyclic ring; m is an integer ranging from 1 to 6, and n is an integer ranging from 1 to 6:

(I-g)

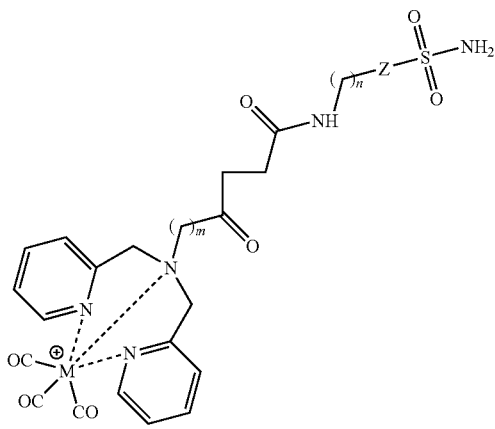

In some embodiments, the complex has the formula of I-h where M is technetium or rhenium, and m is an integer ranging from 0 to 6:

(I-h)

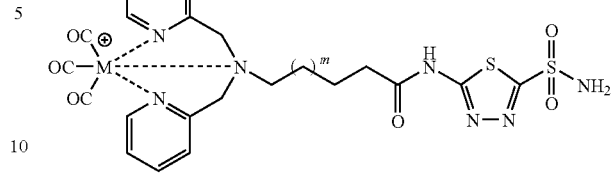

In some embodiments, the complex has the formula of I-i:

(I-i)

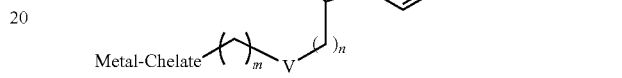

wherein:
V is a bond, O, C=O, C(=X)—NH, a group of

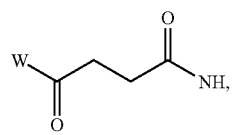

or a group of

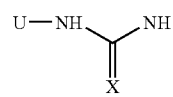

wherein X is O or S; U is a bond or a group of (O—CH$_2$—CH$_2$—O)$_p$—CH$_2$—CH$_2$ wherein p is an integer ranging from 1 to 3;
m is an integer ranging from 0 to 6;
n is an integer ranging from 0 to 6;
Metal represents a metallic moiety comprising a radionuclide; and
Chelate represents a chelating moiety that coordinates with said radionuclide to form said complex.

In some embodiments, the complex has the formula of I-j:

(I-j)

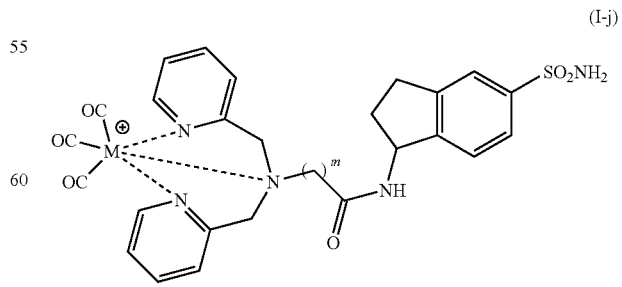

wherein M is technetium or rhenium, and m is an integer ranging from 1 to 6.

In some embodiments, the complex has the formula of I-k:

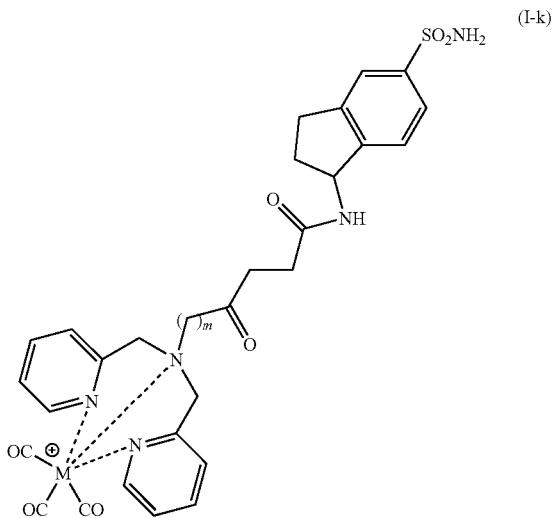

wherein M is technetium or rhenium, m is an integer ranging from 1 to 6.

In some embodiments, the complex has the formula of I-l:

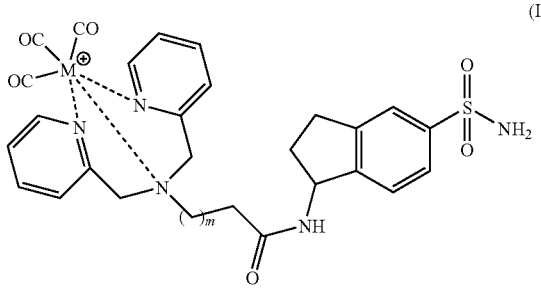

wherein M is technetium or rhenium, m is an integer ranging from 1 to 6.

In another aspect, the invention provides halogenated analogs of compounds that show selectivity for CA-IX over other carbonic anhydrases. The halogenated analogs of compounds comprise charged and/or hydrophobic functional groups that increase cell impermeability. The charged functional groups incorporated herein may be, for example, negatively charged functional groups comprising carboxylic acid, sulfonic acid, sulfuric acid, phosphonic acid, phosphinic acid, phosphoric acid, or ionizable nitrogen-containing heterocycles, such as tetrazoles and triazoles, which present a negatively ionized (e.g., carboxylate) form of a molecule at physiologic pH. The charged functional groups incorporated herein may also be positively charged functional groups comprising amine, guanidine, amidine or N-containing heterocycle, which present a positively ionized form of a molecule at lower pH. The charged groups may also comprise positively charged quaternary amine. The hydrophobic functional groups may be a urea, thiourea, amide, sulfonamide, aromatic ring(s), heteroaromatic ring(s) such as pyridine and pyrimidines, aliphatic hydrocarbon ring(s) and chain(s), ether ring(s) and or chain(s), thioether ring(s) and or chain(s), or the like. The length between the sulfonamide moiety and the charged or hydrophobic functional groups of the compound can be varied to modify the affinity and selectivity of the compound for CA-IX. The pharmacokinetic properties of the compound can also be modified by variations in sulfonamide. Provided below is a compound of general formula II, its stereoisomer or pharmaceutically acceptable salt:

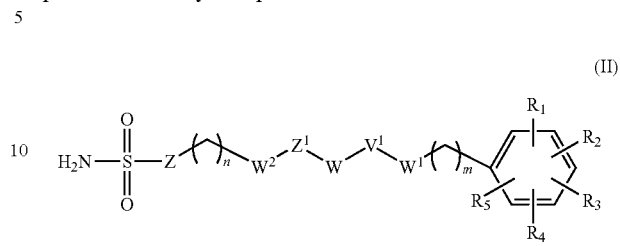

wherein:

$V^1$ is selected from the group consisting of a bond, O, NH, O—$(CH_2—CH_2-0)_q$, a group of

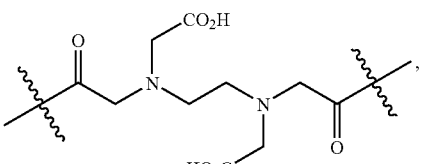

a group of $CHR_6$—CO or $CHR_6$—CO—NH—$CHR_6$—CO wherein $R_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

$W^1$ and $W^2$ are independently a bond, NH, C=X, or a group of

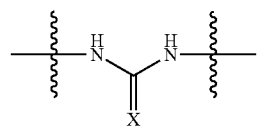

wherein X is O or S;

Z is an aromatic, bicyclic aromatic, heteroaromatic, bicyclic heteroaromatic or heterocyclic ring;

$Z^1$ is a bond, aromatic, bicyclic aromatic, heteroaromatic, bicyclic heteroaromatic or heterocyclic ring;

m is an integer ranging from 0 to 8;

n is an integer ranging from 0 to 8;

q is an integer ranging from 1 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-a where $R_2$ is S elected from the group consisting of hydrogen, carboxyl, halogen, alkoxy, alkyl and substituted or unsubstituted amino:

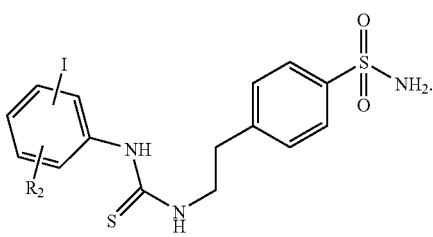
(II-a)

In some embodiments, the compound has the structure of formula II-b:

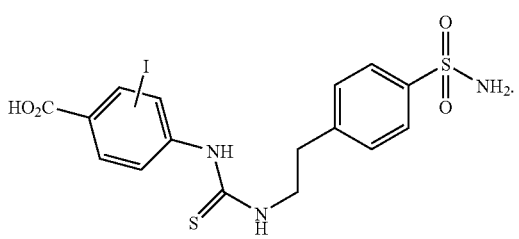
(II-b)

In some embodiments, the compound has the structure of formula II-c where $R_2$, $R_3$ and $R_4$ are independently selected from the group consisting of hydrogen, halogen, carboxyl, alkoxy, alkyl and substituted or unsubstituted amino:

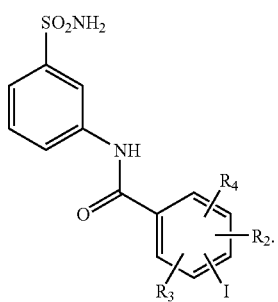
(II-c)

In some embodiments, the compound has the structure of formula II-d where q is 1, and $R_2$, $R_3$ and $R_4$ are independently selected from the group consisting of hydrogen, halogen, carboxyl, alkoxy, alkyl and substituted or unsubstituted amino:

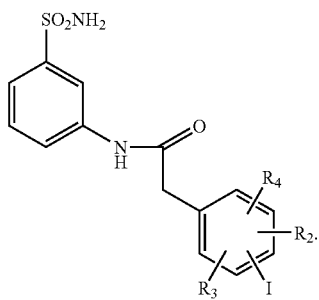
(II-d)

In some embodiments, the compound has the structure of formula II-e where $R_2$ is selected from the group consisting of hydrogen, carboxyl, halogen, alkyl, alkoxy and substituted or unsubstituted amino:

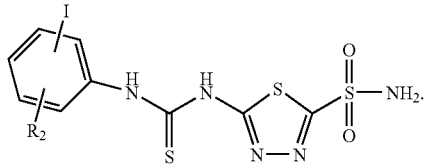
(II-e)

In some embodiments, the compound has the structure of formula II-f where r is an integer ranging from 0 to 6; and $R_2$ is independently selected from the group consisting of hydrogen, halogen, carboxyl, alkoxy, alkyl and substituted or unsubstituted amino:

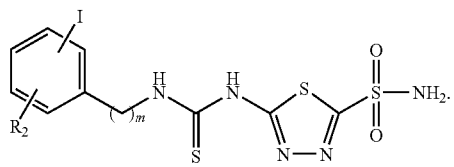
(II-f)

In some embodiments, the compound has the structure of formula II-g where m is an integer ranging from 0 to 6; and $R_2$ is independently selected from the group consisting of hydrogen, halogen, carboxyl, alkoxy, alkyl and substituted or unsubstituted amino:

(II-g)

In some embodiments, the compound has the structure of formula II-h:

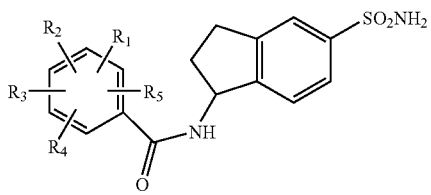
(II-h)

where $R_1$ is iodine; and $R_2$, $R_3$, $R_4$ and $R_5$ is independently selected from the group consisting of hydrogen, halogen, alkyl, and alkoxy.

In some embodiments, the compound of formula II-h is a R-isomer. It is anticipated that the R-isomer of the compound of formula III can adopt a relatively flat conformation with respect to the benzamide aryl ring thus fitting readily in the CA-IX active site.

In some embodiments, the compound has the structure of formula II-i.

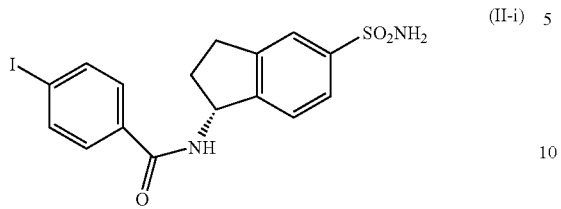
(II-i)

In some embodiments, the compound has the structure of formula I-j.

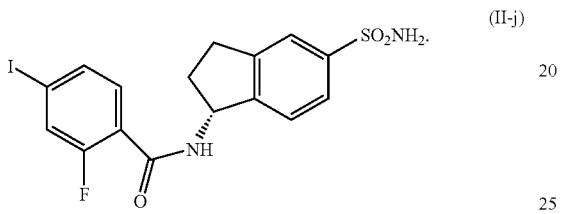
(II-j)

In some embodiments, the compound has the structure of formula II-k.

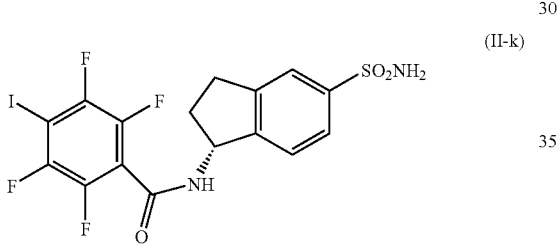
(II-k)

In some embodiments, the compound has the structure of formula II-l:

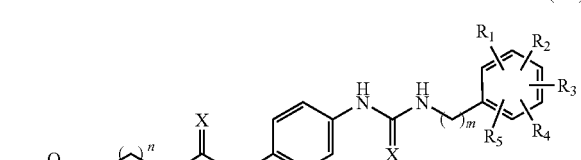
(II-l)

where

X is O or S;

Z is an aromatic, bicyclic aromatic, heteroaromatic, bicyclic heteroaromatic or heterocyclic ring;

m is an integer ranging from 0 to 8;

n is an integer ranging from 0 to 8; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-m:

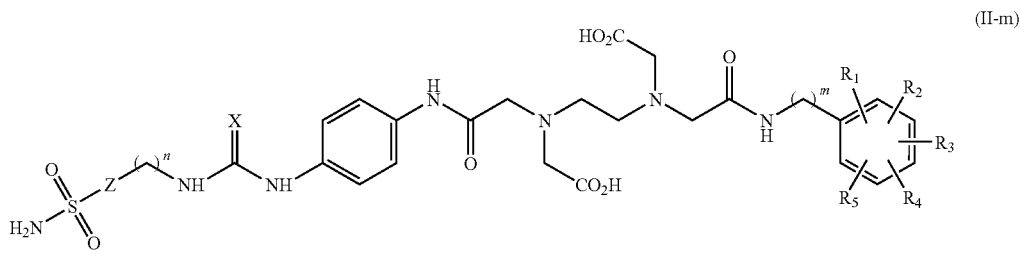
(II-m)

where

X is O or S;

Z is an aromatic, bicyclic aromatic, heteroaromatic, bicyclic heteroaromatic or heterocyclic ring;

m is an integer ranging from 0 to 8;

n is an integer ranging from 0 to 8; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-n:

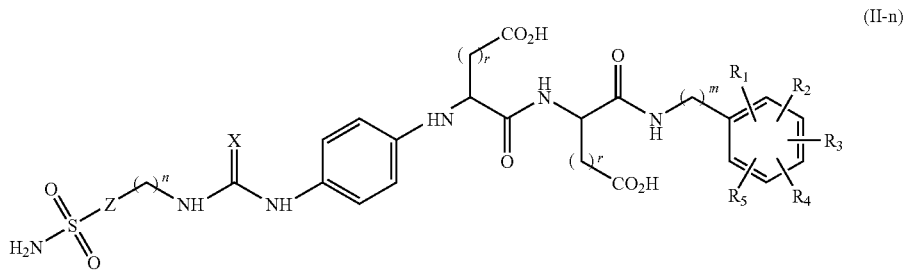

(II-n)

where
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8;
r=1 or 2; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-o:

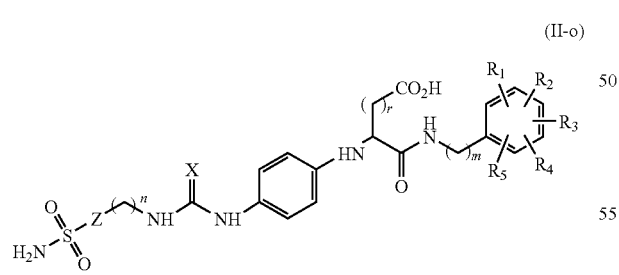

(II-o)

where
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8;
r=1 or 2; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-p:

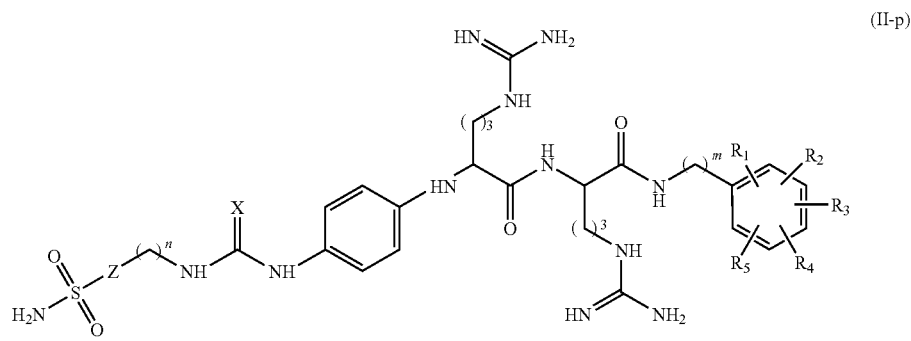

(II-p)

where
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-q:

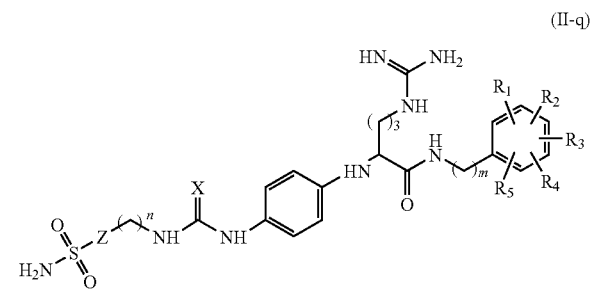

(II-q)

wherein:
X is O or S;
Z is an aromatic, bicyclic aromatic, heteroaromatic, bicyclic heteroaromatic or heterocyclic ring;

m is an integer ranging from 0 to 8;
n is an integer ranging from 0 to 8; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-r:

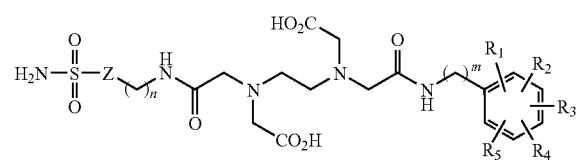

(II-r)

wherein:
Z is an aromatic, bicyclic aromatic, heteroaromatic, bicyclic heteroaromatic or heterocyclic ring;
m is an integer ranging from 0 to 8;
n is an integer ranging from 0 to 8; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-s:

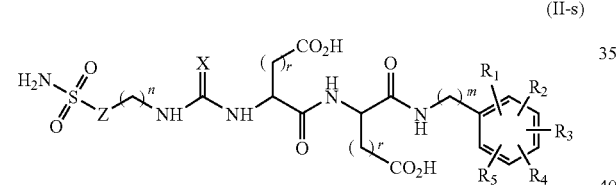

(II-s)

wherein:
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8;
r=1 or 2; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-t:

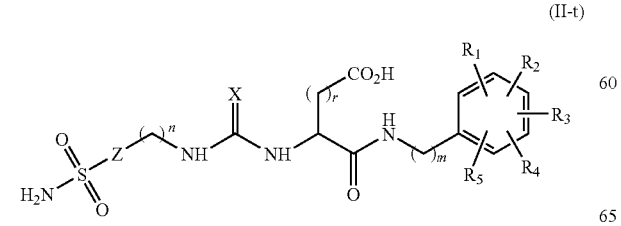

(II-t)

wherein:
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8;
r=1 or 2; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-u:

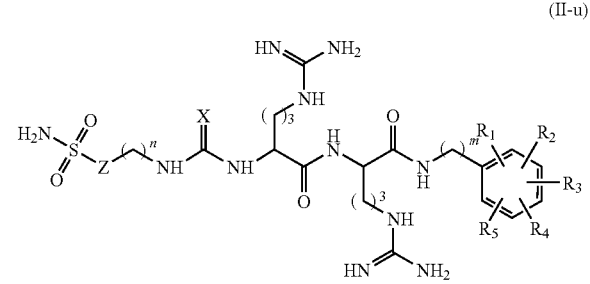

(II-u)

wherein:
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula II-v:

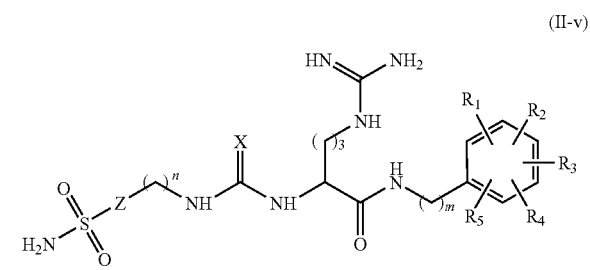

(II-v)

wherein:
X is O or S;
Z is an aromatic, bicyclic aromatic, heteroaromatic, bicyclic heteroaromatic or heterocyclic ring;
m is an integer ranging from 0 to 8;
n is an integer ranging from 0 to 8; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In a further aspect, the invention provides sulfonamide analogs with 1,2,3-triazole linker that show selectivity of CA-IX over other carbonic anhydrases. By utilizing azide-alkyne Huisgen cycloaddition, several groups of 1,2,3-triazole analogs can be easily introduced to the invention compounds of CA-IX inhibitors. Provided is a compound of general formula III or its stereoisomer or pharmaceutically acceptable salt:

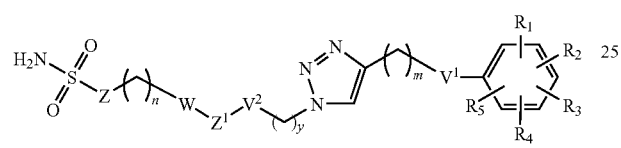
(III)

wherein:
$V^1$ and $V^2$ are independently selected from the group consisting of a bond, O, NH, $(O-CH_2-CH_2-O)_q$, a group of

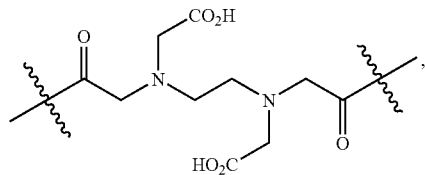 [SMILES: *C(=O)CN(CCN(CC(*)=O)CC(=O)O)CC(=O)O]

a group of $CHR_6-CO$ or $CHR_6-CO-NH-CHR_6-CO$ wherein $R_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;
$W^1$ is a bond, NH, C=X, or a group of

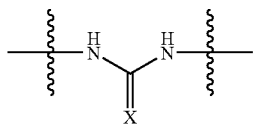

wherein X is O or S;
Z and $Z^1$ are independently an aromatic, bicyclic aromatic, heteroaromatic, bicyclic heteroaromatic or heterocyclic ring;
m is an integer ranging from 0 to 8;
n is an integer ranging from 0 to 8;
q is an integer ranging from 1 to 6;
y is an integer ranging from 0 to 6; and
$R_1, R_2, R_3, R_4$ and $R_5$ are independently selected from the group consisting of hydrogen, carboxyl, halogen, alkyl, alkoxy, and substituted or unsubstituted amino wherein at least one halogen is selected.

In some embodiments, the compound has the structure of formula III-a:

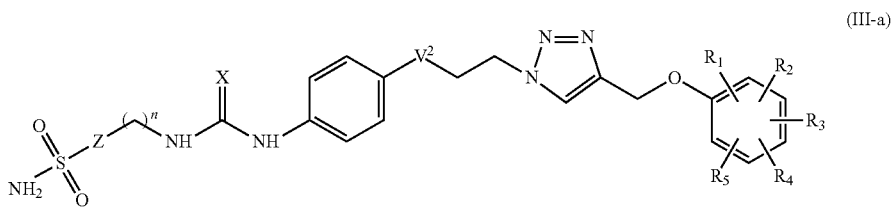
(III-a)

wherein:
$V^2$ selected from the group consisting of a bond, O, NH, $O-(CH_2-CH_2-O)_q$, a group of

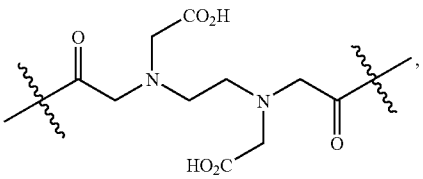

a group of $CHR_6-CO$ or $CHR_6-CO-NH-CHR_6-CO$ wherein $R_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;
X is O or S;
Z is an aromatic, bicyclic aromatic, heteroaromatic, bicyclic heteroaromatic or heterocyclic ring;
n is an integer ranging from 0 to 8;
q is an integer ranging from 1 to 6; and
$R_1, R_2, R_3, R_4$ and $R_5$ are independently selected from the group consisting of hydrogen, carboxyl, halogen, alkyl, alkoxy, and substituted or unsubstituted amino wherein at least one halogen is selected.

In another aspect, the invention provides a compound of formula IV, its stereoisomer or pharmaceutically acceptable salt:

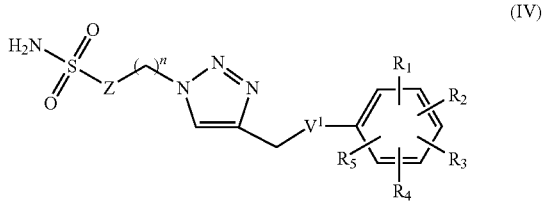
(IV)

wherein:
$V^1$ is selected from the group consisting of a bond, O, NH, $O-(CH_2-CH_2-O)_q$, a group of

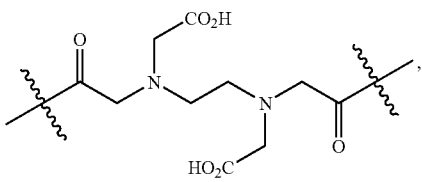 [SMILES: *C(=O)CN(CCN(CC(*)=O)CC(=O)O)CC(=O)O]

a group of $CHR_6$—CO or $CHR_6$—CO—NH—$CHR_6$—CO wherein $R_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

Z is an aromatic, bicyclic aromatic, heteroaromatic, bicyclic heteroaromatic or heterocyclic ring;

n is an integer ranging from 0 to 8;

q is an integer ranging from 1 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected.

In yet another aspect, the invention provides sulfonamide analogs incorporated with a tertiary or quaternary amine containing functional group that show selectivity of CA-IX over other carbonic anhydrases. Provided below is a compound of general formula V, its stereoisomer or pharmaceutically acceptable salt:

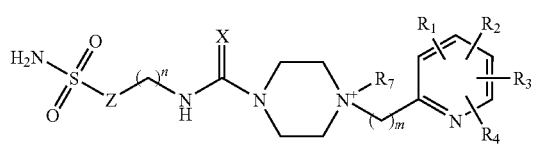

(V)

wherein:

X is O or S;

m is an integer ranging from 0 to 8;

n is an integer ranging from 0 to 8;

$R_1$, $R_2$, $R_3$, and $R_4$ are independently selected from the group consisting of hydrogen, carboxyl, halogen, alkyl, alkoxy, and substituted or unsubstituted amino wherein at least one halogen is selected; and $R_7$ is H or lower alkyl.

In another aspect, the invention provides methods of imaging tissue of a mammal which expresses CA-IX comprising administering to the mammal an effective amount of a radiolabeled compound selected from the group consisting of formulae I, II, III, IV, and V its stereoisomer or pharmaceutically acceptable salt wherein the at least one halogen is a halogen radionuclide e.g., $^{123}I$, $^{125}I$, $^{18}F$, $^{131}I$, and $^{76}Br$. In some embodiments, the methods further comprise determining the level of CA-IX in the tissue. In other embodiments, the methods further comprise monitoring the changes of the level of CA-IX in the tissue over a period of time. The administration in the methods is carried out intravenously.

In yet another aspect, the invention provides methods of treating a mammal suffering a disease which is characterized by over expression of CA-IX. The methods comprise administering to the mammal a therapeutically effective amount of a compound selected from the group consisting of formulae I, II, III, IV, and V its stereoisomer or pharmaceutically acceptable salt.

The complex or compound represented by formula I, II, III or IV may be prepared by methods known in the art. In general, the complex represented by formula I may be prepared by incorporating a Metal-Chelate moiety into a compound containing sulfonamide moiety that exhibits selective binding to CA-IX.

By way of example, the Metal-Chelate compounds may be made by Single Amino Acid Chelate (SAAC™) technology, which is described in U.S. Patent Application Publication No. 2003/0235843, the disclosure of which is incorporated herein by reference in its entirety. A variety of structurally diverse molecules can be made using the SAAC technology. The SAAC technology may provide a rapid, high yield, one pot synthesis of mono-, di-, and mixed alkylated amino acid derivatives. The alkylated amino acid derivatives may possess a tridentate chelating moiety distal to an amino acid functionality. The tridentate chelating group allows facile and robust coordination of a metallic moiety or metallic core such as $\{M(CO)_3\}^{+1}$ core (M is a radionuclide such as Tc or Re). In some embodiments, a metallic core may be inserted prior to performing standard chemistries, including standard deprotection and peptide cleavage chemistries, without loss of the metal from the SAAC complex. Studies on the coordination chemistry of the $\{M(CO)_3\}^{+1}$ core have established that amine, aromatic, heterocyclic, and carboxylate donors provide effective chelating ligands. The tridentate chelate-M(CO)$_3$ complex provide chemical inertness and a broad utility of the amino acid functionality. Various tridentate chelating moieties can be made so as to alter the charge, hydrophobicity, and distance of the tridentate chelate-M(CO)$_3$ complex from the functional moiety of the compound. Scheme 1 illustrate preparation of alkylated SAAC molecules by direct reductive N-alkylations of t-butyloxycarbonyl (BOC) protected lysine with the desired aldehydes with NaBH(OAc)$_3$ as the reducing agent.

Scheme 1: Preparation of mono-, di- and mixed alkylated SAAC molecules

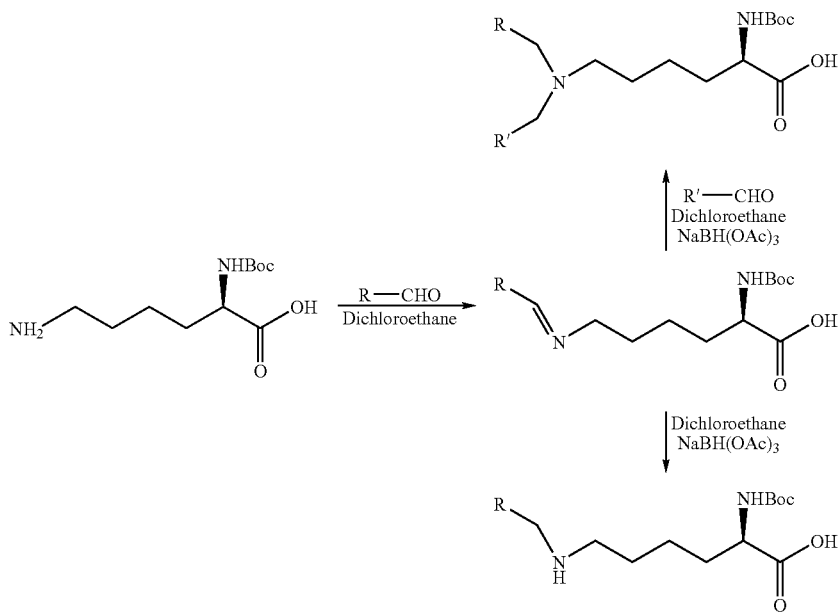

wherein R and R' are independently selected from the group consisting of a-g.

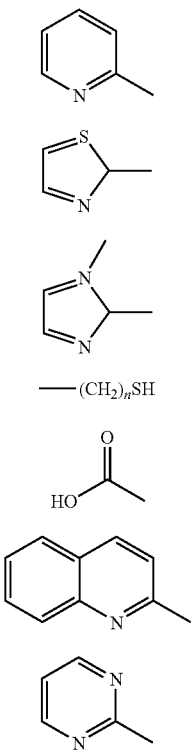

R, R' = a-g

The $\{M(CO)_3\}^{+1}$ (M is e.g. Tc or Re) complexes of the bifunctional chelates can be readily prepared from for example and $[Et_4N]_2[Re(CO)_3Br_3]$, $[Re(CO)_3(H_2O)_3]Br$, or $[Tc(CO)_3(H_2O)_3]$ which is generated in situ from the commercial tricarbonyl kit (Mallinckrodt), respectively.

Scheme 2 illustrates the synthesis of sulfanilamide and homosulfanilamide-$M^+(CO)_3$ complexes having the structures of formula I or IV. Similarly, the 1,3,4-thiadiazole-2-sulfonamide-$M^+(CO)_3$ complexes having the structures of formula I-a can be prepared from the appropriate 1,3,4-thiadiazole starting material. The effect of the distance of the metal complex from the sulfonamide moiety on the affinity and selectivity of CA-IX can be investigated with the exemplary complexes.

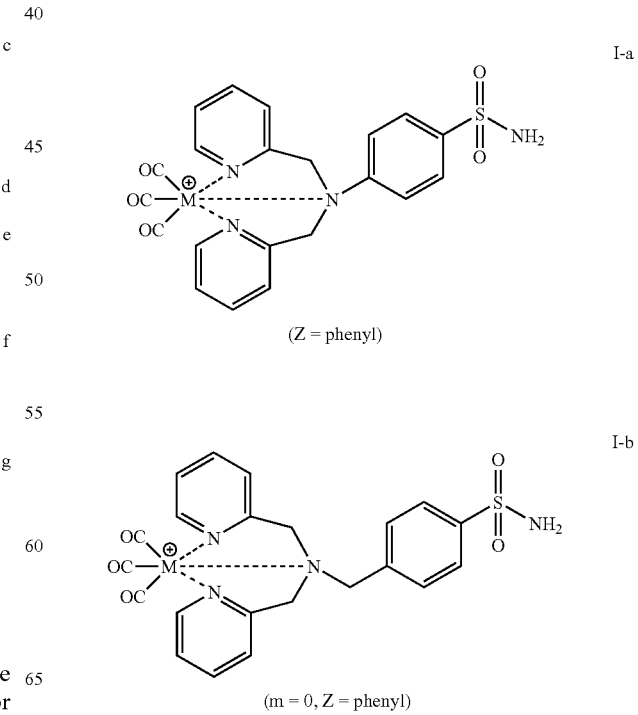

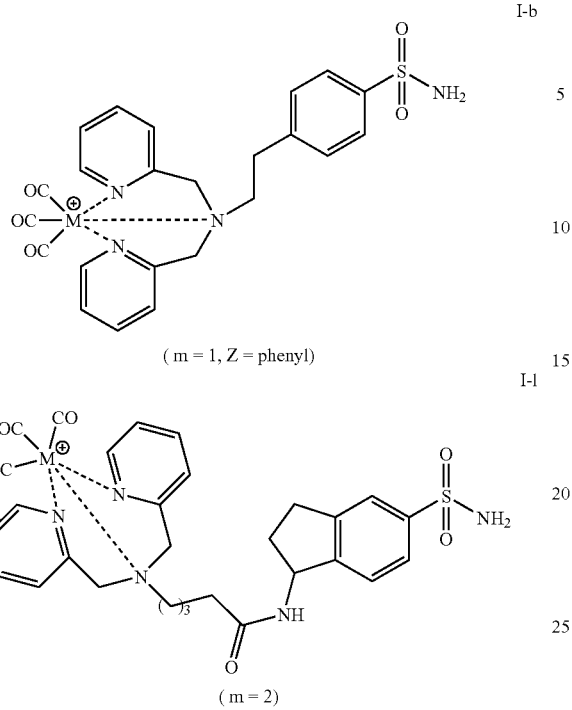
I-b (m = 1, Z = phenyl)
I-l (m = 2)
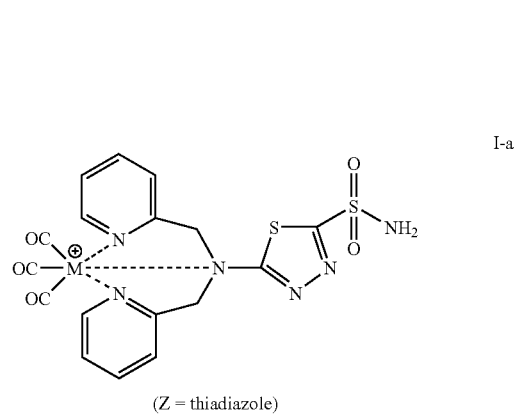
I-a (Z = thiadiazole)
Scheme 2: Synthesis of sulfanilamide-$M^+(CO)_3$ and 1,3,4-thiadiazole-2-sulfonamide-$M^+(CO)_3$ complexes
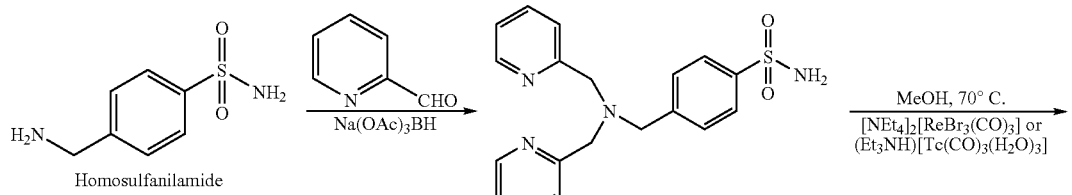
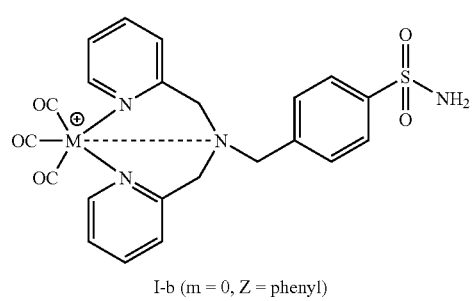
I-b (m = 0, Z = phenyl)
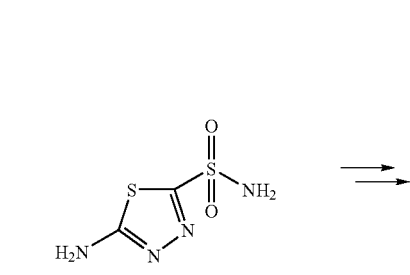
5-amino-1,3,4-thiadiazole-2-sulfonamide
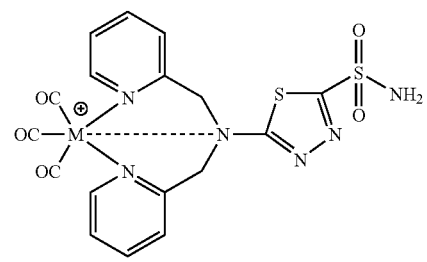
I-a (Z = thiadiazole)

The syntheses can be accomplished by reductive amination of the appropriate amines (e.g. homosulfanilamide and 5-amino-1,3,4-thiadiazole-2-sulfonamide) with two equivalents of 2-pyridinecarboxaldehyde using sodium triacetoxyborohydride as the reducing agent. The obtained free ligands can then be complexed with the desired metal to afford the desired metal complex I-b and I-a.

Scheme 3 illustrates the synthesis of 6-aminoalkanoic acid-$M^+(CO)_3$ complex from preformed $M^+(CO)_3$ ligand. In Scheme 3, the synthetic route utilizes the preformed chelate as the starting material to the homosulfanilamide $M(CO)_3$ Dpa analog (I-d wherein, n=1, m=4, Metal=Re or Tc, Z=phenyl) or the 1,3,4-thiadiazole-2-sulfonamide analog (I-h where m=2, Metal=Re or Tc).

Scheme 3: Synthesis of 6-aminoalkanoic acid-$M^+(CO)_3$ complex from preformed $M^+(CO)_3$ ligand

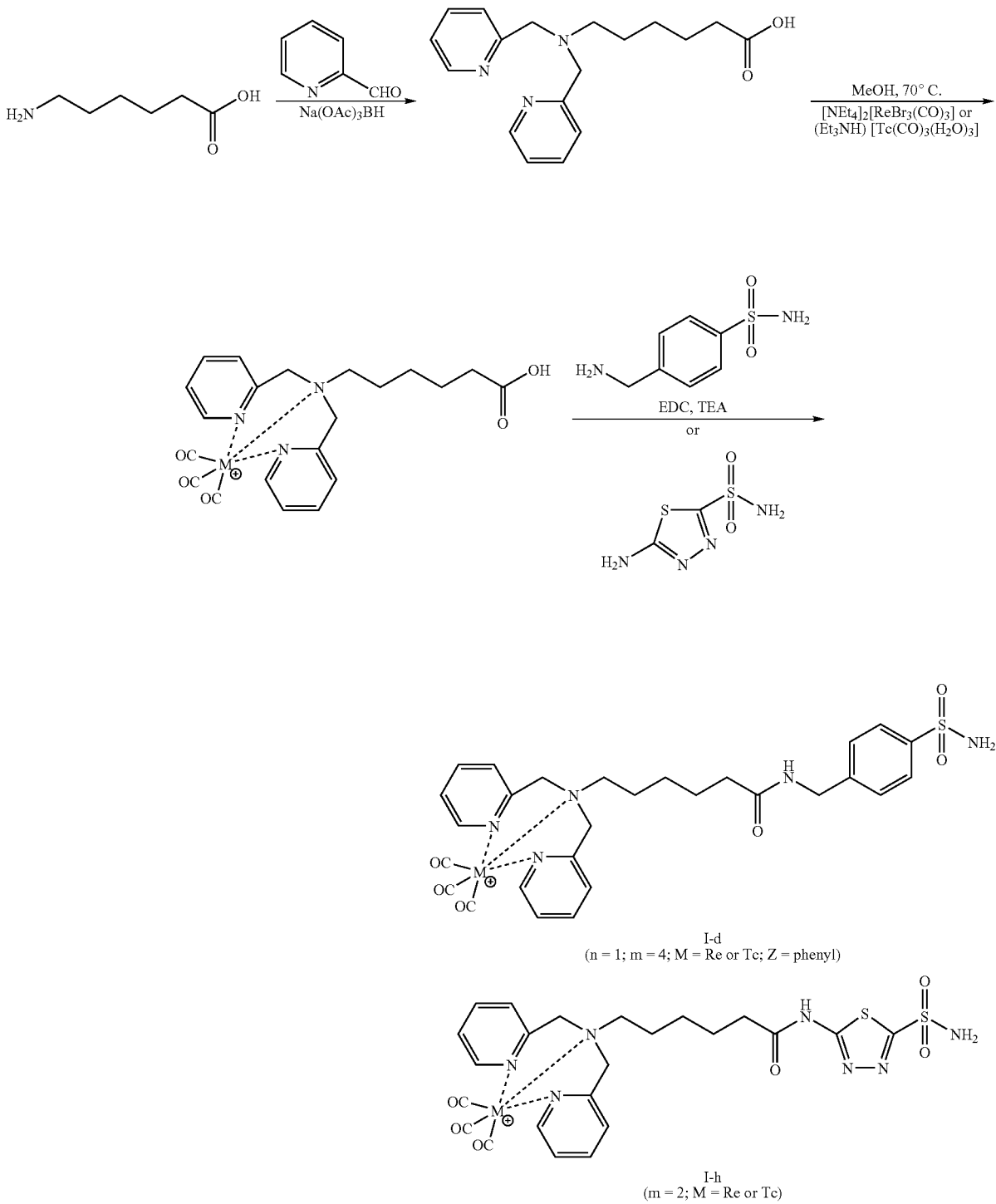

Alternatively, the 6-aminoalkanoic acid-M⁺(CO)₃ complex can be prepared according to Scheme 4 via the non-metalated ligand.

Scheme 4: Alternate synthesis of 6-aminoalkanoic acid-M⁺(CO)₃ complex

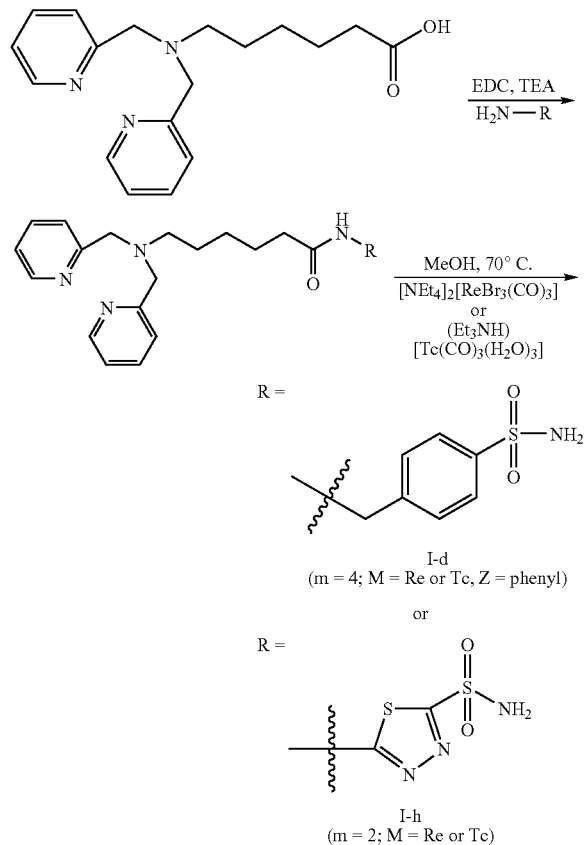

I-d
(m = 4; M = Re or Tc, Z = phenyl)

or

I-h
(m = 2; M = Re or Tc)

Schemes 3 and 4 can be used to synthesize aminoalkanoic acid-M⁺(CO)₃ complexes to explore the effect of more significant variations of the distance of the metal chelator from the sulfonamide moiety by incorporating a tether into these structures. Terminal aminoalkanoic acids such as β-alanine, 4-aminobutanoic acid, 5-aminopentanoic acid, 6-aminohexanoic acid and the 8-aminooctanoic acid are commonly utilized tethers which allow a thorough exploration of the chelate distance from the sulfonamide moiety in a detailed fashion as exemplified by the general structures I-d:

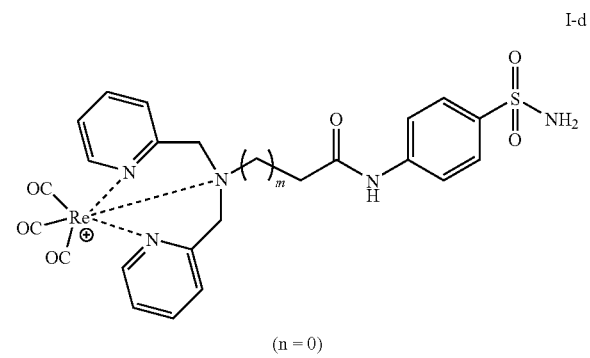

I-d
(n = 0)

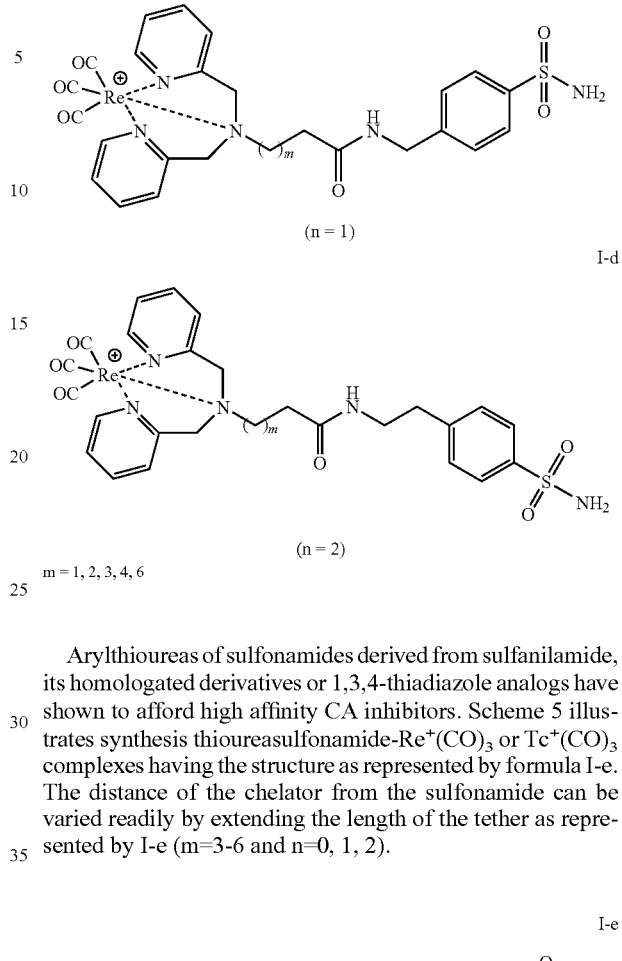

I-d (n = 1)

I-d (n = 2)

m = 1, 2, 3, 4, 6

Arylthioureas of sulfonamides derived from sulfanilamide, its homologated derivatives or 1,3,4-thiadiazole analogs have shown to afford high affinity CA inhibitors. Scheme 5 illustrates synthesis thioureasulfonamide-Re⁺(CO)₃ or Tc⁺(CO)₃ complexes having the structure as represented by formula I-e. The distance of the chelator from the sulfonamide can be varied readily by extending the length of the tether as represented by I-e (m=3-6 and n=0, 1, 2).

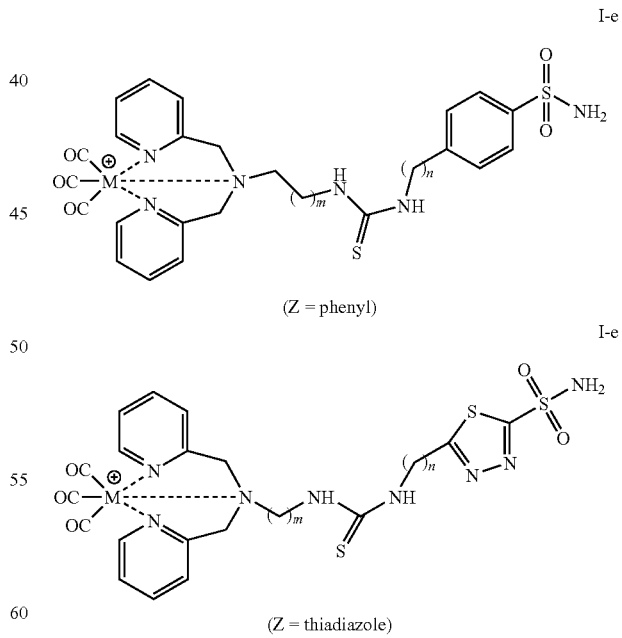

I-e (Z = phenyl)

I-e (Z = thiadiazole)

The molecules in this class may be prepared from the corresponding isothiocyanates as illustrated in Scheme 5. The (homosulfanilamide)thiourea-Re—(CO)₃ complex 16 can be prepared from isothiocyanate 14. Homosulfanilamide can readily be converted to the isothiocyanate 14. Reaction of 14 with the amine metal complex 15 affords the desired sulfonamide rhenium complex 16. Similarly, 5-amino-1,3,4-thiadiazole-2-sulfonamide can readily be converted to the correspondent isothiocyanate followed by reaction with the amine metal complex to afford I-e (m=4, n=0, Z=thiadiazole).

toms into the tether such as oxygen can take advantage of the commercially availability of a variety of short polyethylene glycol (PEG) diamines that can be readily incorporated into the complexes.

Scheme 5: Synthesis of Thioureasulfonamide-M$^+$(CO)$_3$ Complex from Preformed M$^+$(CO)$_3$ Ligand

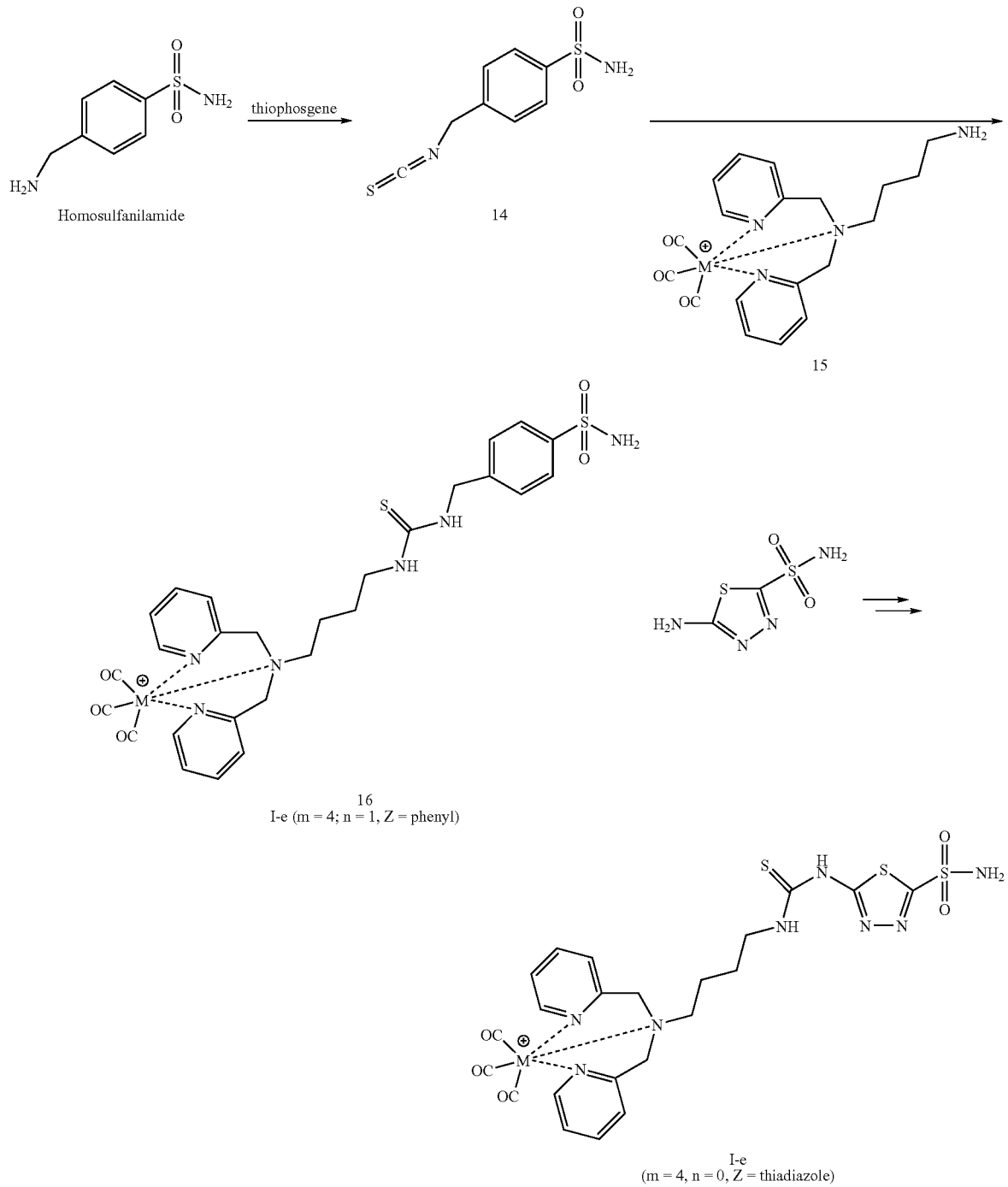

The above reaction scheme is applicable to any modification of the tether by incorporation of heteroatoms into the tether chain. This may have additional benefits on the affinity as well as the selectivity for CA-IX. Incorporation of heteroa- Scheme 6 illustrates the synthesis of sulfanilamide or homosulfanilamide analogs with negative charged functional group, EDTA, having the structures of formula II. Other sulfonamide such as 1,3,4-thiadiazole-2-sulfonamide analogs can be prepared from the appropriate 1,3,4-thiadiazole starting material. The effect of the distance of the negatively charged functional group from the sulfonamide moiety on the affinity and selectivity of CA-IX can be investigated with the exemplary compounds.

The syntheses can be accomplished by reaction of EDTA di-anhydride with the appropriate amines (e.g. sulfanilamide, homosulfanilamide or 5-amino-1,3,4-thiadiazole-2-sulfonamide followed by addition of 4-iodoaniline in situ at room temperature. The obtained iodinated compounds can be further converted to the desired halogen radionuclide, e.g. $^{131}$I by the known methods.

Scheme 7 illustrates the synthesis of thiourea-glutamic acid linked sulfonamides. In Scheme 7, the synthetic route utilizes reaction of di-glutamic acid derivatives (which is prepared from the iodinated starting material with glutamic acid utilizing standard peptide coupling conditions) and isocyanatobenzenesulfonamide to furnish the thiourea linkage. Starting with the different isocyanate sulfonamide analogs, e.g., 4-(isothiocyanatomethyl)benzenesulfonamide or 5-(isothiocyanatomethyl)-1,3,4-thiadiazole-2-sulfonamide, the corresponding homosulfanilamide analogs or 1,3,4-thiadiazole-2-sulfonamide analogs can be prepared after the deprotection step.

Scheme 6: Synthesis of negatively charged Ethylenediaminetetraacetic acid (EDTA) derived analogs

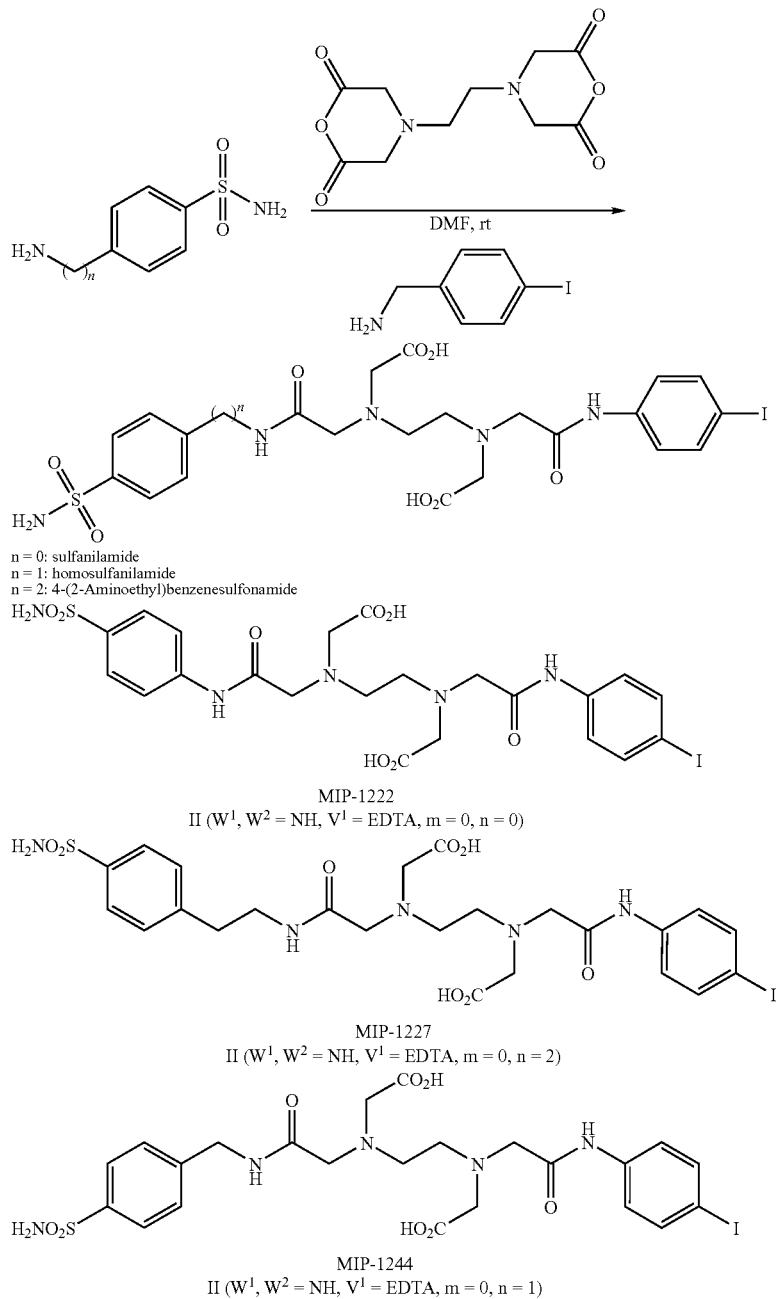

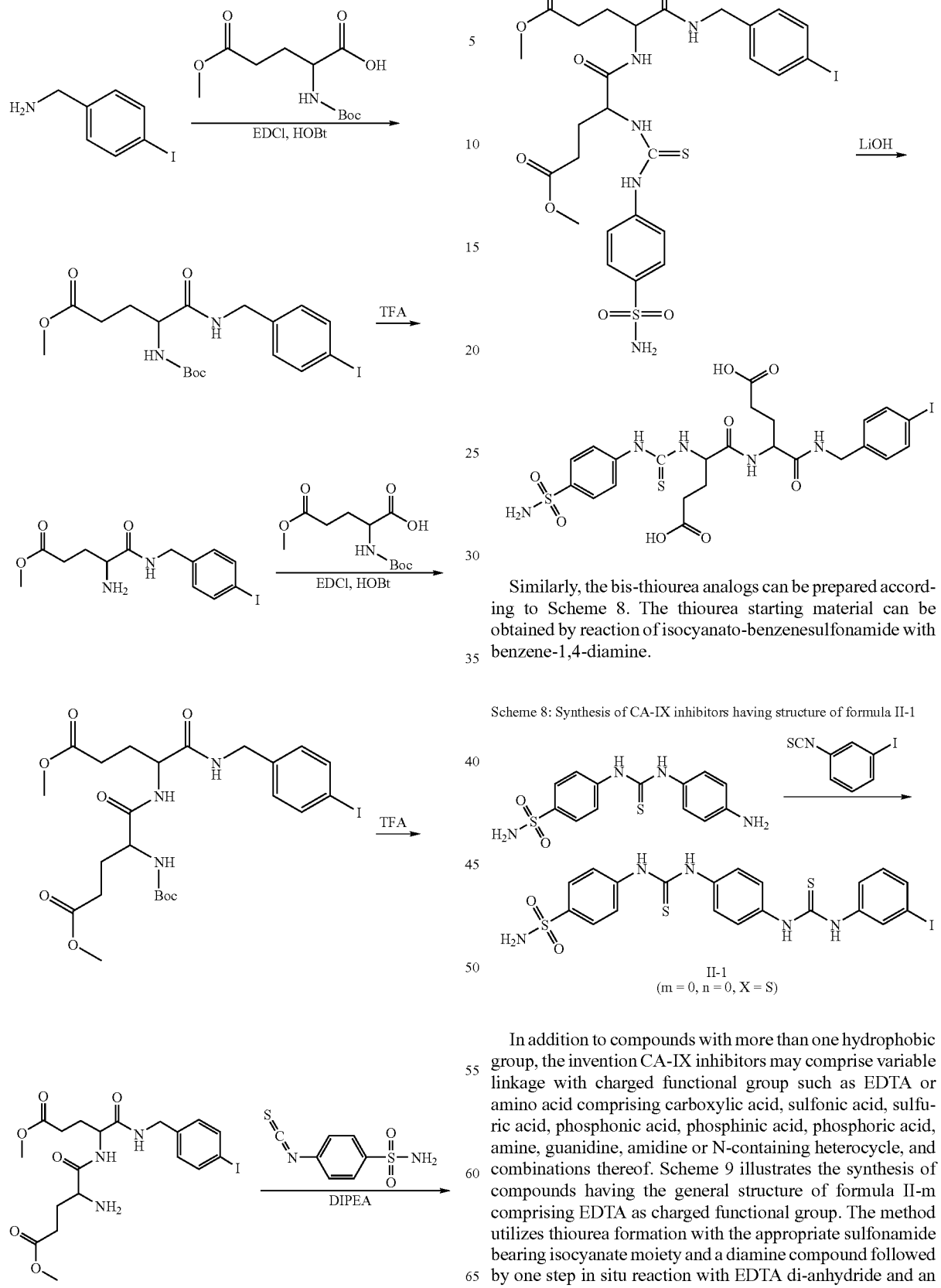

Similarly, the bis-thiourea analogs can be prepared according to Scheme 8. The thiourea starting material can be obtained by reaction of isocyanato-benzenesulfonamide with benzene-1,4-diamine.

In addition to compounds with more than one hydrophobic group, the invention CA-IX inhibitors may comprise variable linkage with charged functional group such as EDTA or amino acid comprising carboxylic acid, sulfonic acid, sulfuric acid, phosphonic acid, phosphinic acid, phosphoric acid, amine, guanidine, amidine or N-containing heterocycle, and combinations thereof. Scheme 9 illustrates the synthesis of compounds having the general structure of formula II-m comprising EDTA as charged functional group. The method utilizes thiourea formation with the appropriate sulfonamide bearing isocyanate moiety and a diamine compound followed by one step in situ reaction with EDTA di-anhydride and an amine compound (e.g. iodoaniline, iodobenzylamine) to afford compounds having the structure of formula II-m.

Scheme 9: Synthesis of CA-IX inhibitors having structure of formula II-m

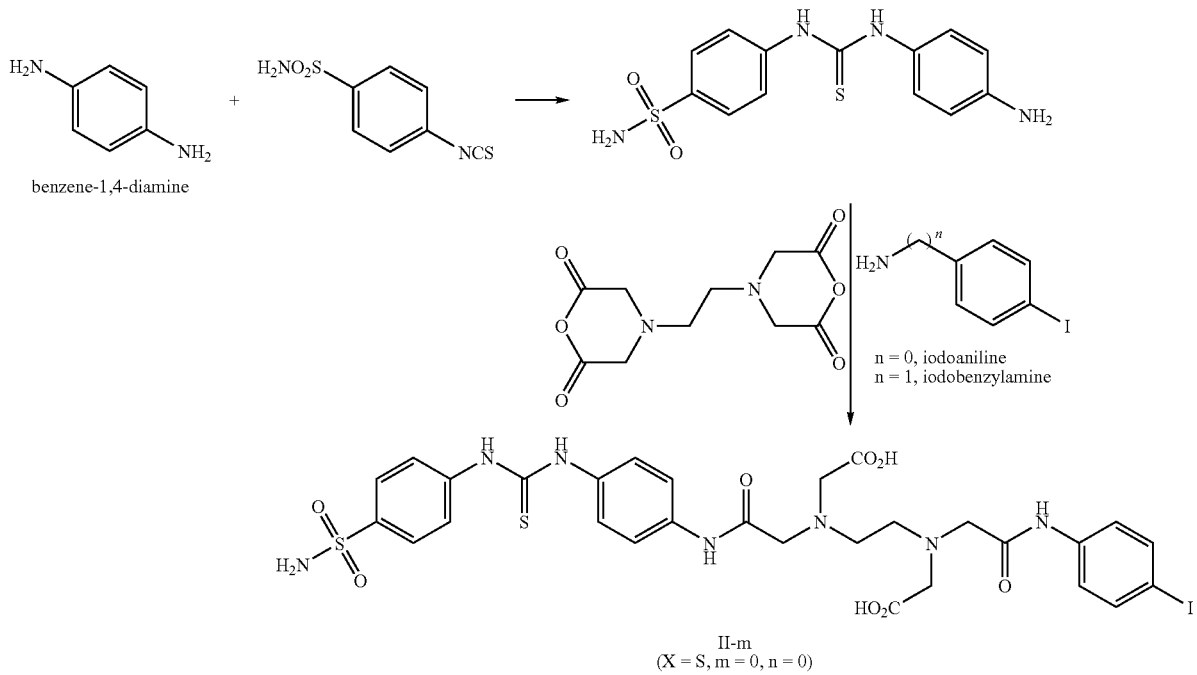

Besides thiourea, other hydrophobic moieties can be introduced to the invention CA-IX inhibitors. For example, employing the efficient preparation of 1,2,3-triazole analogs by azide-alkyne Huisgen cycloaddition, compounds having the structures of formula III or IV can be prepared as illustrated in Scheme 10 and 11.

In Scheme 10, the azido intermediate can be prepared via a simple ether formation between a hydroxyphenyl, e.g., tert-butyl 4-hydroxyphenylcarbamate, and a tosylated azido precursor, e.g., 2-(2-(2-azidoethoxy)ethoxy)ethyl 4-methylbenzenesulfonate. Triazole linkage is then furnished by reacting the azido intermediate with the appropriate acetylene compounds, e.g., 1-iodo-4-(prop-2-ynyloxy)benzene. After deprotection and thiourea formation, compounds having the structure of formula III-a with the thiourea, triazole and polyethylene glycol (PEG) functional groups can be prepared.

Similarly, compounds having the structure of formula IV can be prepared via triazole formation (Scheme 11). The acetylene intermediate with PEG functional group can be prepared under the similar ether formation between the hydroyphenyl and the tosylated acetylene precursor. The triazole is formed between the acetylene intermediate and the azido sulfonamide compound.

Scheme 10. Synthesis of CA-IX inhibitors comprising triazole moiety

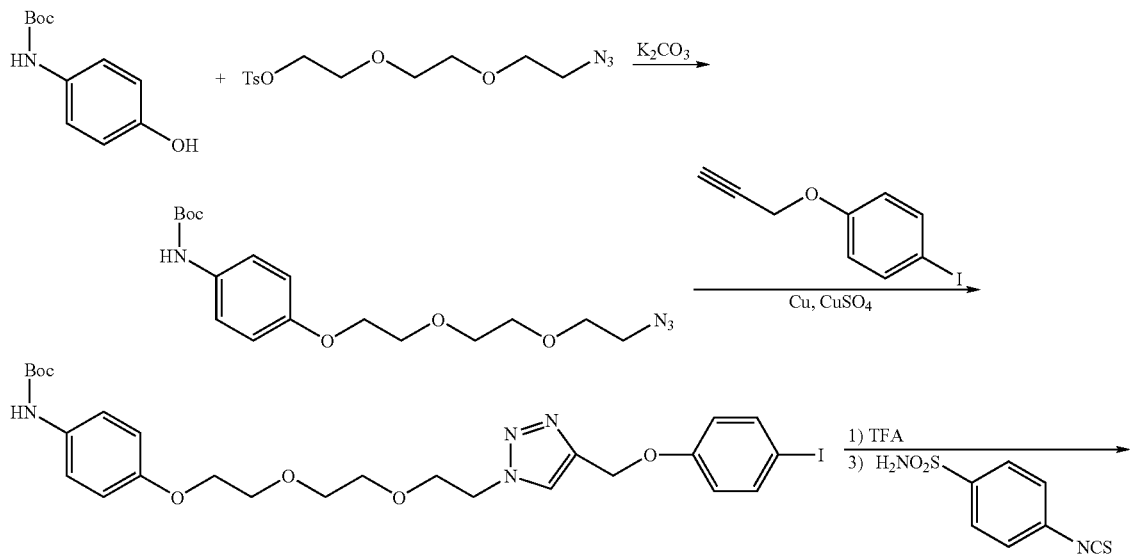

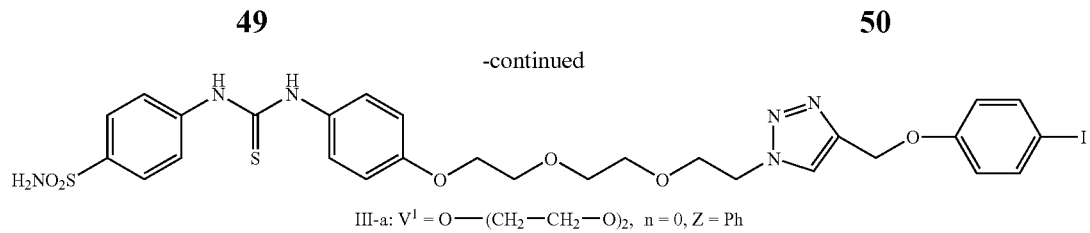

III-a: V¹ = O—(CH₂—CH₂—O)₂, n = 0, Z = Ph

Scheme 11: Synthesis of CA-IX inhibitors having structure of formula IV

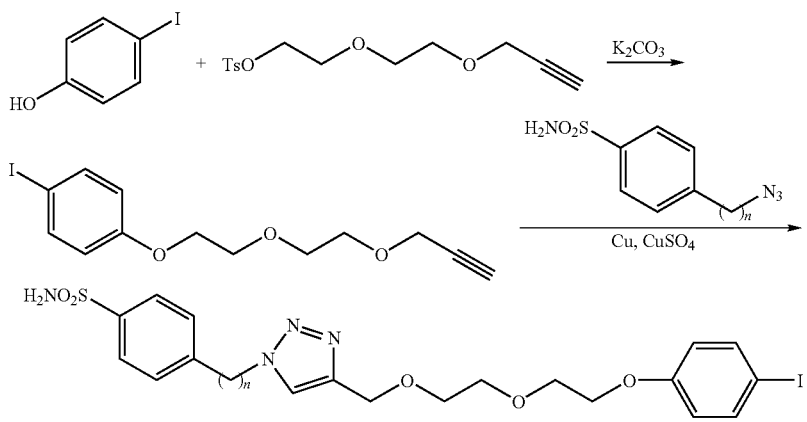

The above reaction schemes are applicable to any modification of the azido or acetylene precursors by incorporation of charged or hydrophobic functional groups into the precursors. See examples in Scheme 12. This may have additional benefits on the affinity as well as the selectivity for CA-IX.

Scheme 12: Examples of acetylene or azido precursors for preparation of the triazole analogs of CA-IX inhibitors

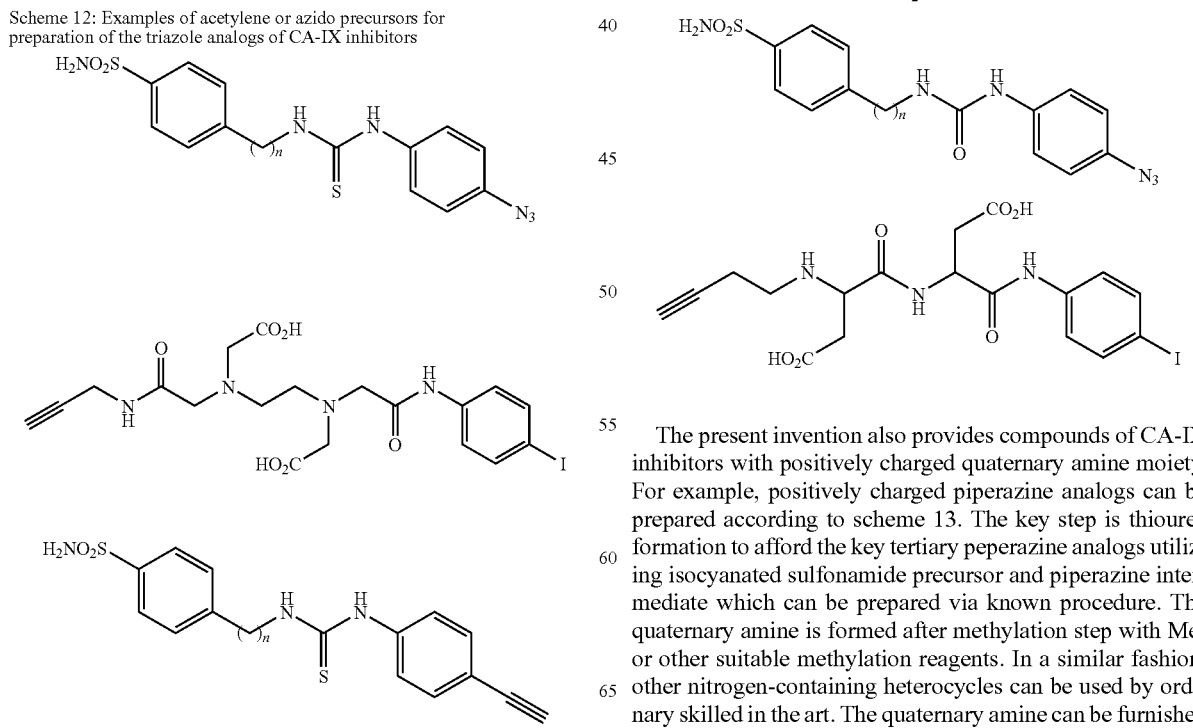

The present invention also provides compounds of CA-IX inhibitors with positively charged quaternary amine moiety. For example, positively charged piperazine analogs can be prepared according to scheme 13. The key step is thiourea formation to afford the key tertiary peperazine analogs utilizing isocyanated sulfonamide precursor and piperazine intermediate which can be prepared via known procedure. The quaternary amine is formed after methylation step with MeI or other suitable methylation reagents. In a similar fashion, other nitrogen-containing heterocycles can be used by ordinary skilled in the art. The quaternary amine can be furnished by other alkylation reagents known in the art.

Scheme 13. Synthesis of CA-IX inhibitors comprising charged quaternary amine group

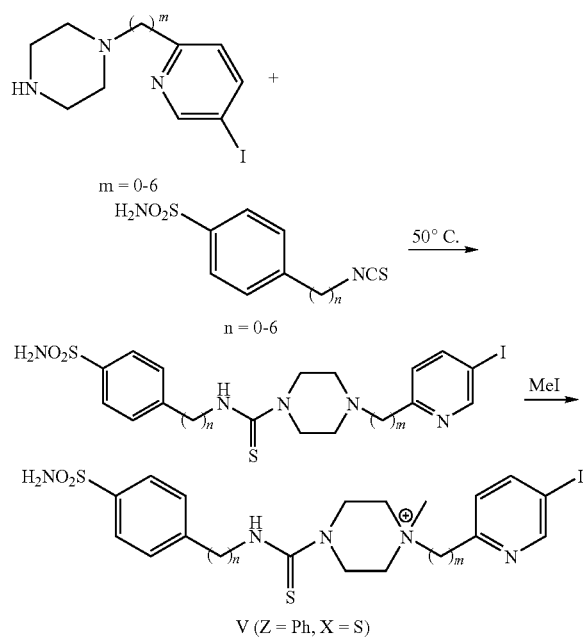

V (Z = Ph, X = S)

The complex or compound of the invention may be used in accordance with the methods described herein by those skilled in the art, e.g., by specialists in nuclear medicine, for diagnostic imaging of tissue which expresses CA-IX, and therapeutic treatment of diseases which are characterized by over expression of CA-IX.

The complex or compound of the invention may be used in the following manner. An effective amount of the compound (from 1 to 50 mCi) may be combined with a pharmaceutically acceptable carrier for use in imaging studies. In accordance with the invention, "an effective amount" of the compound is defined as an amount sufficient to yield an acceptable image using equipment which is available for clinical use. An effective amount of the complex may be administered in more than one injection. Effective amounts of the complex will vary according to factors such as the degree of susceptibility of the individual, the age, sex, and weight of the individual, idiosyncratic responses of the individual and dosimetry. Effective amounts of the complex will also vary according to instrument and film-related factors. Optimization of such factors is well within the level of skill of a person skilled in the art.

As used herein, the pharmaceutically acceptable carrier includes any and all solvents, dispersion media, coatings, antibacterial and antifungal agents, isotonic agents, absorption delaying agents, and the like. The use of such media and agents for pharmaceutically active substances is well known in the art. The complex or compound may be administered to an individual in an appropriate diluent or adjuvant, or in an appropriate carrier such as human serum albumin or liposomes. Supplementary active compounds can also be used with the complex. Pharmaceutically acceptable diluents include saline and aqueous buffer solutions. Adjuvants contemplated herein include resorcinols, non-ionic surfactants such as polyoxyethylene oleyl ether and hexadecyl polyethylene ether.

In one embodiment, the complex or compound is administered parenterally as injections (intravenous, intramuscular or subcutaneous). The complex or compound may be formulated as a sterile, pyrogen-free, parenterally acceptable aqueous solution. The preparation of such parenterally acceptable solutions, having due regard to pH, isotonicity, stability, and the like, is within the skill in the art. Certain pharmaceutical compositions suitable for parenteral administration comprise one or more imaging agents in combination with one or more pharmaceutically acceptable sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. A formulation for injection should contain, in addition to the cardiovascular imaging agent, an isotonic vehicle such as sodium chloride solution, Ringer's solution, dextrose solution, dextrose and sodium chloride solution, lactated Ringer's solution, dextran solution, sorbitol solution, a solution containing polyvinyl alcohol, or an osmotically balanced solution comprising a surfactant and a viscosity-enhancing agent, or other vehicle as known in the art. The formulation used in the present invention may also contain stabilizers, preservatives, buffers, antioxidants, or other additives known to those skilled in the art.

The amount of the complex or compound used for diagnostic or therapeutic purposes will depend upon the nature and severity of the condition being treated, on the nature of therapeutic treatments which the patient has undergone, and on the idiosyncratic responses of the patient. Ultimately, the attending physician will decide the amount of complex or compound to administer to each individual patient and the duration of the imaging study.

In another aspect, the invention provides a kit for imaging which comprises one or more of the complex or compound described above, in combination with a pharmaceutically acceptable solution containing a carrier such as human serum albumin or an auxiliary molecule such as mannitol or gluconate. Human serum albumin for use in the kit of the invention may be made in any way, for example, through purification of the protein from human serum or through recombinant expression of a vector containing a gene encoding human serum albumin. Other substances may also be used as carriers, for example, detergents, dilute alcohols, carbohydrates, and the like. In one embodiment, a kit according to the invention may contain from about 1 to about 50 mCi of a complex or compound. In another embodiment, a kit may contain the unlabeled fatty acid stereoisomer which has been covalently or non-covalently combined with a chelating agent, and an auxiliary molecule such as mannitol, gluconate, and the like. The unlabeled fatty acid stereoisomer/chelating agent may be provided in solution or in lyophilized form. The kits may also include other components which facilitate practice of the methods of the invention. For example, buffers, syringes, film, instructions, and the like may optionally be included as components of the kits of the disclosure.

EXAMPLES

The following examples are provided to illustrate certain aspects of the present invention and to aid those of skill in the art in practicing the invention. These examples are not intended to limit the scope of the invention.

In the following examples, reactions were carried out in dry glassware under an atmosphere of argon or nitrogen unless otherwise noted. Reactions were purified by flash column chromatography, medium pressure liquid chromatography using a Biotage SP4 or by preparative high pressure liquid chromatography (HPLC). $^1$H NMR was obtained on a Bruker 400 MHz instrument. Spectra are reported as ppm □ and are referenced to the solvent resonances in CDCl₃, DMSO-d₆ or methanol-d₄. Solvents were obtained from Sigma-Aldrich and Fisher Scientific. Reagents were obtained from Sigma Aldrich, Bachem, Fisher Scientific, Alfa Aesar, and Acros.

The following abbreviations are used in the examples: dichloromethane (DCM), ethyl acetate (EA), hexanes (Hex), dichloroethane (DCE), dimethyl formamide (DMF), trifluoroacetic acid (TFA), tetrahydrofuran (THF), carbonyldiimidazole (CDI), dicyclohexyl carbodiimide (DCC), dimethylaminopyridine (DMAP), t-butyloxycarbonyl (BOC), diisopropylethylamine (DIPEA), triethylamine (TEA), benzyloxycarbonyl (CBZ), ethanol (EtOH), and methanol (MeOH). If not defined, the abbreviations or terms have their generally accepted meanings.

Example 1

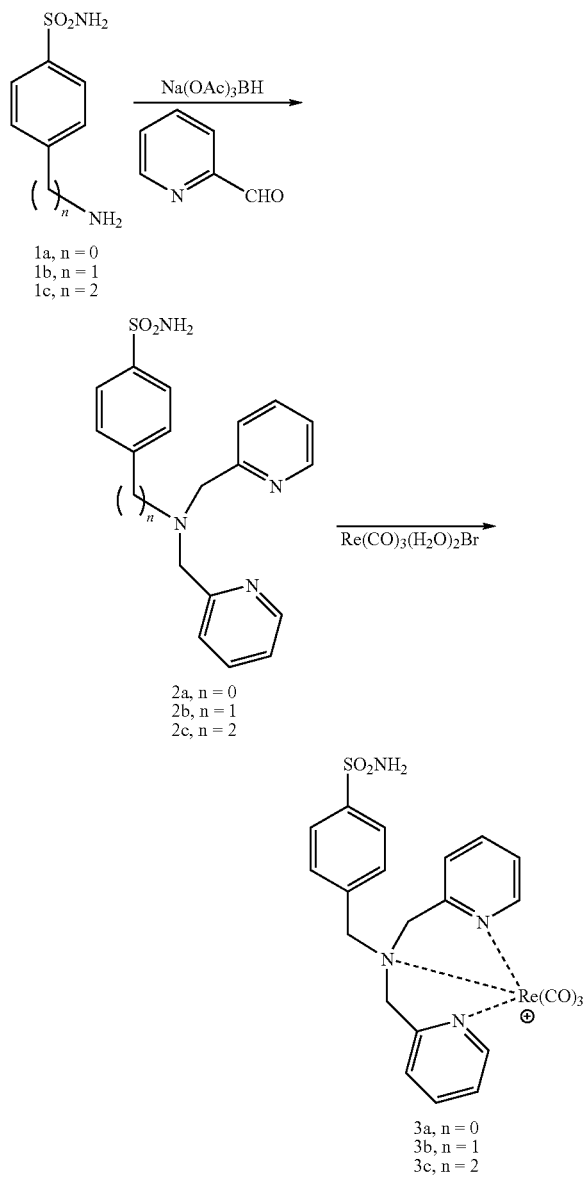

4-(bis(pyridin-2-ylmethyl)amino)benzenesulfonamide (2a)

A suspension of sulfonilamide (1a, 5.0 g, 29 mmol) and pyridine-2-carboxaldehyde (6 mL, 64 mmol), in EtOH (100 mL) was heated to reflux and then stirred at room temperature for 30 min. The solvents were removed in vacuo to afford a yellow solid. The resulting residue was dissolved in EtOH (100 mL), cooled to 0° C., and sodium triacetoxyborohydride (4.4 g, 120 mmol) was added in portions. The resulting mixture was stirred at 0° C. for 1 h and then allowed to warm to room temperature for 3 h. The reaction was quenched by careful addition of 2N sodium hydroxide (25 mL). The resulting mixture was poured into saturated sodium bicarbonate (200 mL) and extracted with DCM (3×150 mL). The pooled organic extracts were dried (sodium sulfate) and concentrated. Flash chromatography (DCM/MeOH, 1:0 to 9:1) as the gradient followed by crystallization from ethyl acetate afforded 2a as a white solid (3.41 g, 33%). ¹H NMR (400 MHz, CDCl₃) δ 8.58 (m, 2H), 7.65 (m, 4H), 7.28 (m, 2H), 7.23 (m, 4H), 6.62 (d, J=8.8 Hz, 2H), 4.22 (d, J=8.8 Hz, 2H); (M+H)⁺ (355).

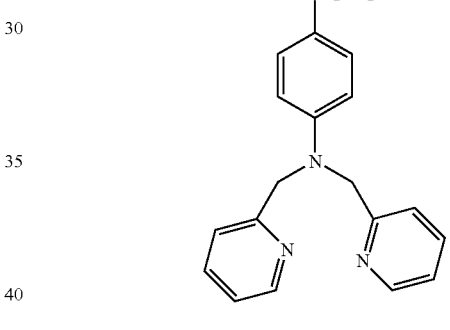

4-((bis(pyridin-2-ylmethyl)amino)methyl)benzenesulfonamide (2b)

A suspension of aminomethylbenzenesulfonamide hydrochloride (1b) (2.2 g, 10 mmol) and pyridine-2-carboxaldehyde (2.4 mL, 25 mmol), in EtOH (50 mL) was heated to a reflux briefly, and the solvents were removed in vacuo to afford a yellow solid. The resulting residue was suspended in 1,2-dichloroethane (50 mL) and sodium triacetoxyborohydride (12.7 g, 60 mmol) was added in portions. The resulting mixture was stirred at room temperature for 18 h. The reaction was quenched by the careful addition of 2N sodium hydroxide (20 mL). The resulting mixture was poured into water (100 mL) and extracted with DCM (3×100 mL). The pooled organic extracts were dried (sodium sulfate) and concentrated. Crystallization from ethyl acetate afforded 2b as a white solid (1.26 g, 34%). ¹H NMR (400 MHz, CDCl₃) δ 8.52 (d, J=4.9 Hz, 2H), 7.83 (d, J=7.2 Hz, 2H), 7.66 (m, 2H), 7.50 (m, 4H), 7.15 (dd, J=5.2, 6.6 Hz, 2H), 3.78 (s, 4H), 3.70 (s, 2H); (M+H)⁺ (369).

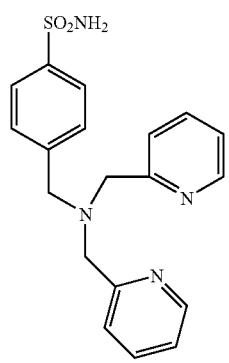 [SMILES: NS(=O)(=O)c1ccc(CN(Cc2ccccn2)Cc2ccccn2)cc1]

4-(2-(bis(pyridin-2-ylmethyl)amino)ethyl)benzene-sulfonamide (2c)

A suspension of 2-aminoethylbenzenesulfonamide (1c) (2.0 g, 10 mmol) and pyridine-2-carboxaldehyde (2.4 mL, 25 mmol), in EtOH (50 mL) was heated to a reflux briefly, and the solvents were removed in vacuo to afford a yellow solid. The resulting residue was suspended in 1,2-dichloroethane (50 mL), and sodium triacetoxyborohydride (12.7 g, 60 mmol) was added in portions. The resulting mixture was stirred at room temperature for 18 h. The reaction was quenched by the careful addition of 2N sodium hydroxide (20 mL). The resulting mixture was poured into water (100 mL) and extracted with DCM (3×100 mL). The pooled organic extracts were dried (sodium sulfate) and concentrated. Crystallization from ethyl acetate afforded 2c as a white solid (2.17 g, 57%). $^1$H NMR (400 MHz, CDCl$_3$) δ 8.46 (m, 2H), 7.69 (m, 4H), 7.28 (m, 6H), 7.21 (m, 2H), 3.79 (s, 4H), 2.87 (t, J=7.2 Hz, 2H), 2.70 (t, J=7.2 Hz, 2H); (M+H)$^+$ (383).

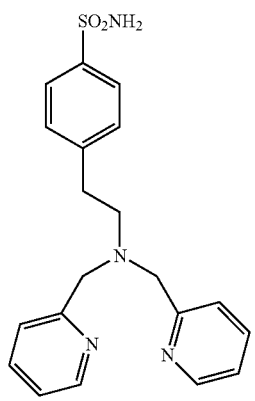 [SMILES: NS(=O)(=O)c1ccc(CCN(Cc2ccccn2)Cc2ccccn2)cc1]

Tricarbonyl Rhenium (I) 4-(bis(pyridin-2-ylmethyl) amino)benzenesulfonamide Bromide (3a) (MIP-1160)

A suspension of 2a (2.0 g, 5.6 mmol) and Re(CO)$_3$(H$_2$O)Br (2.51 g, 6.2 mmol), in MeOH (10 mL) was placed in a pressure tube. The reaction mixture was heated on a bath at 100° C. for 42 hours and then cooled to room temperature. The resulting yellow suspension was diluted with water (75 mL) and extracted with DCM (3×50 mL). The pooled extracts were passed through a pad of silica gel using 10% MeOH in DCM (100 mL) as the eluent. The solvents were removed in vacuo and the residue was crystallized from ethanol to afford MIP-1160 as a yellow solid (27 mg). $^1$H NMR (400 MHz, DMSO-d$_6$) δ 8.72 (d, J=5.4 Hz, 2H), 7.99 (m, 2H), 7.70 (m, 2H), 7.51 (d, J=8.5 Hz, 2H), 7.48 (d, J=8.5 Hz, 2H), 7.40 (m, 2H), 6.60 (d, J=9.8 Hz, 2H), 6.55 (d, J=9.6 Hz, 2H); (M+H)$^+$ (625).

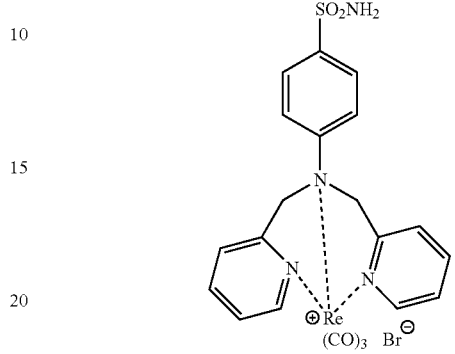

Tricarbonyl Rhenium (I) 4-((bis(pyridin-2-ylmethyl) amino)methyl)-benzenesulfonamide Bromide (3b) (MIP-1161)

A suspension of 2b (300 mg, 0.80 mmol) and Re(CO)$_3$(H$_2$O)Br (405 mg, 0.88 mmol), in MeOH (5 mL) was placed in a pressure tube. The reaction mixture was heated on an oil bath at 100° C. for 42 hours and then cooled to room temperature. The resulting yellow suspension was diluted with water (25 mL) and extracted with DCM (3×25 mL). The pooled extracts were passed through a pad of silica gel using 10% MeOH in DCM (100 mL) as the eluent. The solvents were removed in vacuo and the residue was crystallized from water-methanol to afford MIP-1161 as a brown solid (18 mg, 4%). $^1$H NMR (400 MHz, DMSO-d$_6$) δ 8.81 (d, J=5.4 Hz, 2H), 8.02 (d, J=7.5 Hz, 2H), 7.96 (m, 4H), 7.49 (d, J=8.4 Hz, 2H), 7.37 m, 2H), 5.28 (d, J=16 Hz, 2H), 4.99 (s, 2H), 4.36 (d, J=16.0 Hz, 2H); (M+H)$^+$ (639).

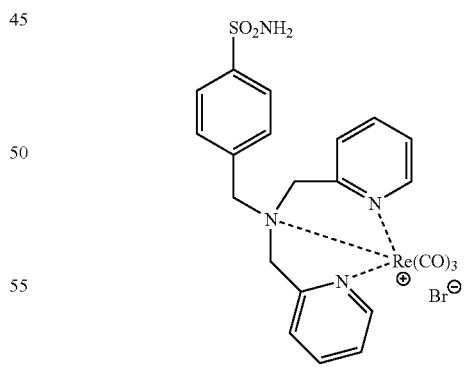

Tricarbonyl Rhenium (I) 4-(2-(bis(pyridin-2-ylmethyl)amino)ethyl)-benzenesulfonamide Bromide (3c) (MIP-1162)

A suspension of 2c (300 mg, 0.80 mmol) and Re(CO)$_3$(H$_2$O)Br (405 mg, 0.88 mmol), in MeOH (5 mL) was placed in a pressure tube. The reaction mixture was heated on an oil bath at 100° C. for 42 h and then cooled to room temperature. The resulting yellow suspension was diluted with water (25 mL) and extracted with DCM (3×25 mL). The pooled extracts were passed through a pad of silica gel using 10% MeOH in DCM (100 mL) as the eluent. The solvents were removed in vacuo and the residue was crystallized from 50% aqueous ethanol (10 mL) to afford MIP-1162 as a white solid (86 mg, 17%). $^1$H NMR (400 MHz, DMSO-$d_6$) δ 8.82 (d, J=5.4 Hz, 2H), 8.02 (m, 2H), 7.83 (d, J=8.3 Hz, 2H), 7.63 (d, J=8.3 Hz, 2H), 7.60 (d, J=7.8 Hz, 2H), 7.49 (m, 2H), 7.32 (s, 2H), 5.11 (m, 4H), 3.94 (m, 2H), 3.27 (m, 2H); (M+H)$^+$ (653).

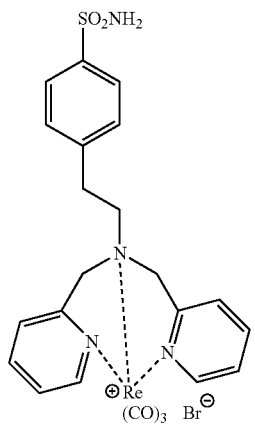

Example 2

4-oxo-4-(4-sulfamoylphenethylamino)butanoic Acid 4-(2-aminoethyl)benzene sulfonamide (1 g, 5.0 mmol) and succinic anhydride (500 mg, 5.0 mmol) were combined in a round bottom flask containing dioxane (100 mL) and the slurry was heated to a reflux overnight. The white solid was filtered and washed with cold dioxane to yield the desired product (1.4 g, 4.6 mol, 92%) as a white solid. $^1$H NMR (400 MHz, DMSO-$d_6$) δ 8.00 (s, 1H), 7.71 (d, J=8.1 Hz, 2H), 7.36 (d, J=8.1 Hz, 2H), 7.38 (s, 1H), 3.26 (m, 2H), 2.75 (t, J=7.1 Hz, 2H), 2.5 (m, 2H), 2.3 (t, J=7.1 Hz, 2H); (M+H)$^+$ (301).

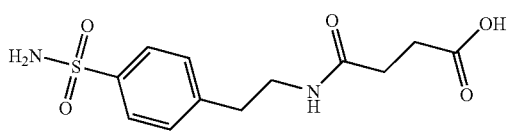 [SMILES: NS(=O)(=O)c1ccc(CCNC(=O)CCC(=O)O)cc1]

Tricarbonyl Rhenium (I) $N^1$-(4-(bis(pyridin-2-ylmethyl)amino)butyl)-$N^4$-(4-sulfamoylphenethyl)succinamide Bromide 4-oxo-4-(4-sulfamoylphenethylamino)butanoic acid (210 mg, 0.68 mmol) and tricarbonyl rhenium(I) ($N^1$,$N^1$-bis(pyridin-2-ylmethyl)propane-1,4-diamine) bromide (404 mg, 1.34 mmol) were dissolved in DMF (2 mL) and DIPEA (1.5 mL). The slurry was stirred at room temperature until all the components were in solution. DCC (148 mg, 0.72 mmol) was then added in one portion and the reaction was stirred overnight. The solution was evaporated to dryness and cold acetone (20 mL) was added to the crude reaction mixture which was filtered to remove dicyclohexylurea. The acetone solution was dried under vacuum and crude solid purified by flash column chromatography (reverse phase) to afford the desired product as an off-white solid. (M+H)$^+$ (823).

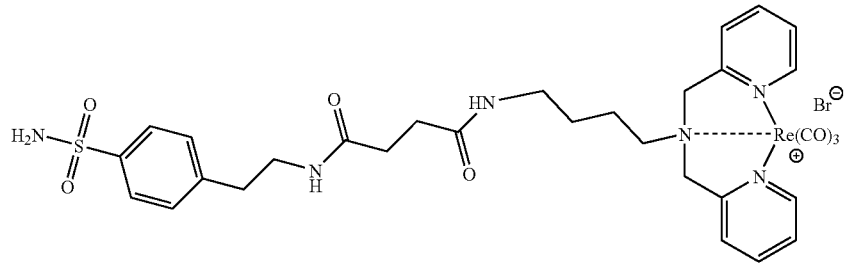

Example 3 t-Butyl 6-(bis(pyridin-2-ylmethyl)amino)hexylcarbamate

The commercially available BOC-1,6-diaminohexane (5.0 g, 23.5 mmol) was added to DCE (250 mL) and vigorously stirred at room temperature while 2-pyridine carboxaldehyde (4.1 mL, 51.7 mmol) was added in one portion. The solution was stirred for 10 min at room temperature then sodium triacetoxyborohydride (11.5 g, 54 mmol) was added in one portion. The solution was stirred overnight at room temperature. The bright yellow solution was evaporated to dryness, treated with 2N sodium hydroxide (150 mL) and extracted with DCM (4×150 mL). The organic extracts were dried over sodium sulfate and concentrated to afford a yellow oil (7.15 g, 76% yield). (M+H)$^+$ (399).

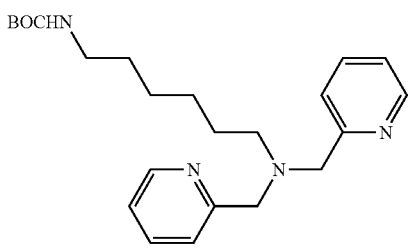

Tricarbonyl Rhenium(I) t-Butyl 6-(bis(pyridin-2-ylmethyl)amino)hexylcarbamate Bromide t-Butyl 6-(bis(pyridin-2-ylmethyl)amino)hexylcarbamate (355 mg, 0.89 mmol) was combined in methanol (4 mL) in a pressure tube and Re(CO)$_3$(H$_2$O)$_2$Br (360 mg, 0.9 mmol) was added and stirred under argon overnight at 125° C. The solution was concentrated under vacuum and treated with acetone (20 mL) and filtered through celite to remove rhenium salts. The solution was evaporated dry to afford the desired product (509 mg, 0.76 mmol, 85%) as a tan foam. (M+H)$^+$ (671).

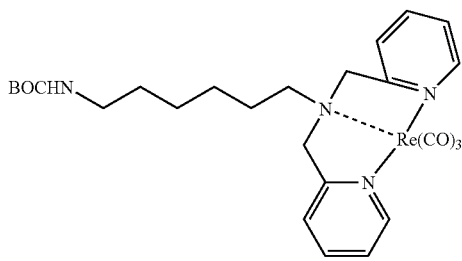

Tricarbonyl Rhenium(I) 6-(bis(pyridin-2-ylmethyl)amino)-hexylamine Bromide

Tricarbonyl Rhenium(I) t-butyl 6-(bis(pyridin-2-ylmethyl)amino)hexylcarbamate bromide (509 mg, 0.76 mmol) was dissolved in DCM (2 mL) and anisole (100 CL) was added. To this solution was added TFA (4 mL) in one portion and the solution was stirred for 2.5 h or until the deprotection was judged complete by TLC. Evaporation of the solvent gave the desired TFA salt as an oil (433 mg, 0.76 mmol, 100%). $^1$H NMR (400 MHz, DMSO-d$_6$) δ 8.00 (m, 2H), 8.01 (m, 2H), 7.83 (s, 3H), 7.55 (m, 2H), 7.41 (m, 2H), 4.89 (s, 4H), 3.75 (m, 2H), 2.75 (m, 2H), 1.85 (m, 2H), 1.6 (m, 2H), 1.35 (m, 4H); (M+H)$^+$ (571).

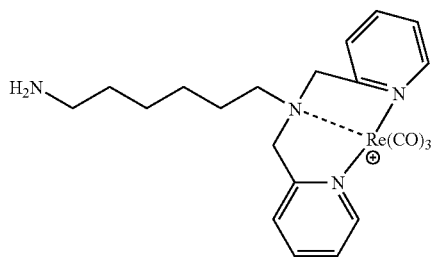

Example 4

3-(2-Aminoethyl)-2-methyl-1H-indole-5-sulfonamide

4-Hydrazinylbenzenesulfonamide hydrochloride salt (12 g, 51 mmol) and 5-chloropentanone (6.2 g, 51 mmol) were combined in ethanol (50 mL) and heated to a reflux overnight. The resulted brown solution was filtered to remove the precipitate formed and the solids were washed with ethanol (300 mL) to afford the desired product (10.9 g, 37 mmol, 73% yield) as the hydrochloride salt. $^1$H NMR (400 MHz, DMSO-d$_6$) δ 11.49 (s, 1H), 8.11 (s, 3H), 7.98 (m, 1H), 7.5 (m, 1H), 7.39 (m, 1H), 7.07 (s, 2H), 3.0 (m, 2H), 2.91 (s, 2H), 2.37 (s, 3H); (M+H)$^+$ (254).

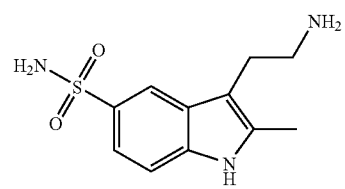 [SMILES: Cc1[nH]c2ccc(S(N)(=O)=O)cc2c1CCN]

3-(2-(bis(pyridin-2-ylmethyl)amino)ethyl)-2-methyl-1H-indole-5-sulfonamide 3-(2-Aminoethyl)-2-methyl-1H-indole-5-sulfonamide (350 mg, 1.49 mmol) was added to DCE (40 mL) and the reaction mixture was warmed to 60° C. 2-Pyridine carboxaldehyde (337 mg, 3.14 mmol) was added in one portion and the solution was stirred for 2 h. Sodium triacetoxyborohydride (761 mg, 3.59 mmol) was then added in one portion and the reaction was stirred overnight at 60° C. The reaction was concentrated to dryness, treated with 2N sodium hydroxide (50 mL) and extracted with DCM (3×150 mL). The organic layer was dried with sodium sulfate and concentrated to afford the desired product (273 mg, 0.63 mmol, 41%) as a yellow oil which was used directly. $^1$H NMR (400 MHz, DMSO-d$_6$) δ 11.13 (s, 1H), 8.50 (m, 3H), 7.91 (d, J=8.3 Hz, 1H), 7.72 (m, 3H), 7.46 (m, 4H), 7.33 (d, J=8.3 Hz, 1H), 7.22 (m, 3H), 7.01 (s, 1H), 3.86 (s, 1H), 2.90 (m, 2H), 2.60 (m, 2H), 2.21 (s, 3H); (M+H)$^+$ (436).

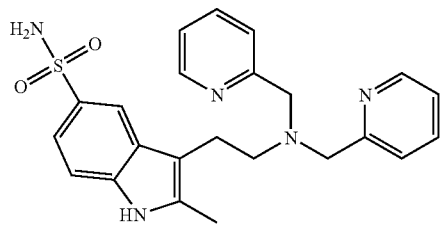 [SMILES: Cc1[nH]c2ccc(S(N)(=O)=O)cc2c1CCN(Cc1ccccn1)Cc1ccccn1]

Tricarbonyl Rhenium(I) 3-(2-(bis(pyridin-2-ylmethyl)amino)ethyl)-2-methyl-1H-indole-5-sulfonamide Bromide 3-(2-(bis(pyridin-2-ylmethyl)amino)ethyl)-2-methyl-1H-indole-5-sulfonamide (273 mg, 64 mmol) was suspended in MeOH (5 mL) in a pressure tube. To this suspension was added Re(CO)$_3$(H$_2$O)Br (257 mg, 0.64 mmol) in one portion. The solution was blanketed with argon gas and stirred for 4 h at 125° C. The yellow solution was evaporated to dryness and the crude material was treated with acetone (50 mL) and the solids which formed were filtered. The filtrate was concentrated under vacuum to afford the desired product (290 mg, 0.41 mmol, 65%) as a yellow solid. $^1$H NMR (400 MHz, DMSO-$d_6$) δ 11.47 (s, 1H), 8.83 (d, J=5.5 Hz, 2H), 8.12 (s, 1H), 8.03 (t, J=7.4 Hz, 2H), 7.62 (d, J=7.4 Hz, 2H), 7.54 (m, 1H), 7.42 (m, 3H), 7.06 (s, 2H), 5.16 (t, J=5.6 Hz, 3H), 5.11 (s, 1H), 3.81 (m, 2H), 3.27 (m, 2H), 2.47 (d, J=4.6 Hz, 5H), 2.07 (d, J=4.6 Hz, 2H); (M+H)$^+$ (706).

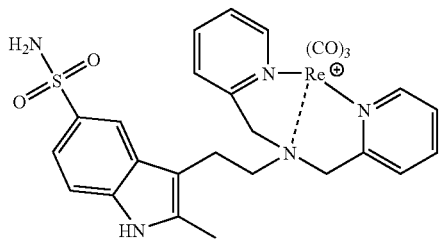

4-Thioureabenzenesulfonamides were prepared by methods illustrated in the following scheme as modified from the method described in Casini et al, *Journal of Enzyme Inhibition and Medicinal Chemistry*, 2002, Vol. 17 (5), 333-343.

In general, an appropriate substituted aniline was added to a suspension of 4-isothiocyanato-benzenesulfonamide (2.0 mmol) in dry acetonitrile (10 mL) was added and the reaction was stirred at room temperature for 3 h. The reaction mixture was concentrated to obtained crude solids, which were recrystallized from acetone-water to obtain the desired 4-thioureabenzensulfonamides as white to off-white solids in yields ranging from 45-95%. Similarly, one can prepare the 1,3,4-thiadiazole analogs from 5-isothiocyanato-1,3,4-thiadiazole-2-sulfonamide in the same fashion.

Example 5

4-(3,3-bis(pyridin-2-ylmethyl)thioureido)benzenesulfonamide (MIP-1138)

To a suspension of 4-isothiocyanatobenzenesulfonamide (401 mg, 1.87 mmol) in dry acetonitrile (10 mL) was added bis(pyridin-2-ylmethyl)amine (373 mg, 1.87 mmol). The reaction mixture went clear and a white precipitate formed. The solid was filtered, washed with acetonitrile and dried to afford MIP-1138 as a white sold (710 mg, 92%). $^1$H NMR (400 MHz, DMSO-$d_6$) δ 11.18 (s, 1H), 8.61 (br, 2H), 7.79-7.64 (m, 6H), 7.34-7.25 (m, 6H), 5.14 (br, 4H); (M+H)$^+$ (414).

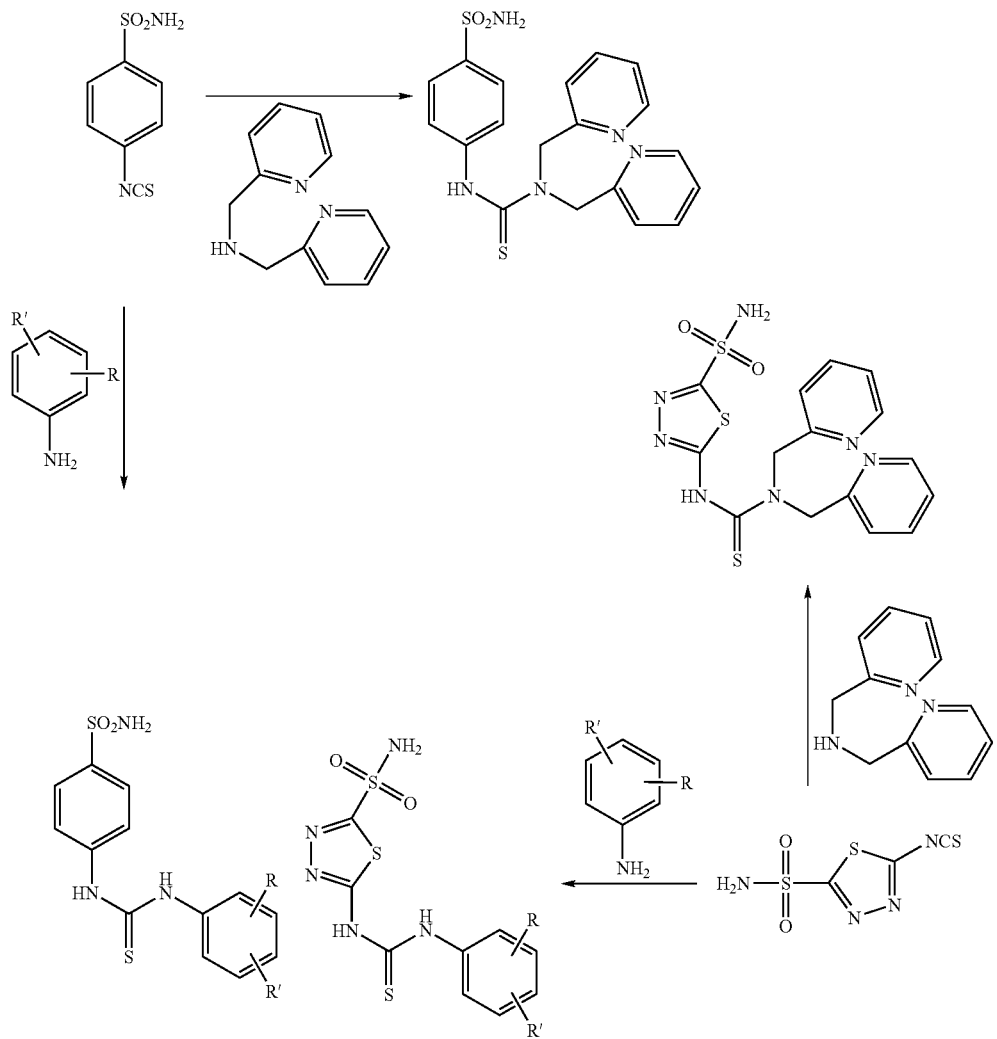

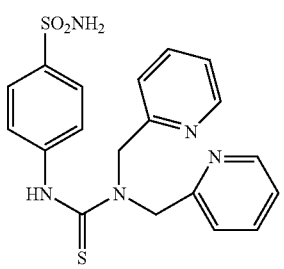 [SMILES: NS(=O)(=O)c1ccc(NC(=S)N(Cc2ccccn2)Cc2ccccn2)cc1]

Example 6

4-(3-(3-iodobenzyl)thioureido)benzenesulfonamide (MIP-1139)

To a suspension of 4-isothiocyanatobenzenesulfonamide (378 mg, 1.76 mmol) in dry acetonitrile (10 mL) and triethylamine (0.3 mL, 4.0 mmol) was added 3-iodobenzylamine hydrochloride salt (476 mg, 1.76 mmol). The reaction mixture became warm and a clear solution resulted. After stirring for 2 h the reaction was concentrated and the crude solid recrystallized from methanol/water to afford a white solid. The solid was filtered and washed with hexanes to afford the desired product MIP-1139 (715 mg, 91%). $^1$H NMR (400 MHz, DMSO-$d_6$) δ 9.95 (br, 1H), 8.48 (br, 1H), 7.74-7.61 (m, 5H), 7.36-7.12 (m, 3H), 4.70 (m, 2H); (M+H)$^+$ (448).

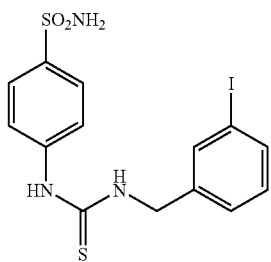 [SMILES: NS(=O)(=O)c1ccc(NC(=S)NCc2cccc(I)c2)cc1]

Similarly, the following compounds were prepared.

Example 7

4-((3-(3-iodophenyl)thioureido)methyl)benzenesulfonamide (MIP-1185)

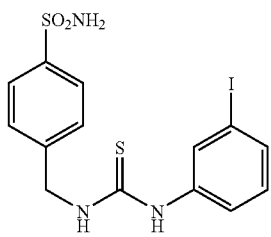 [SMILES: NS(=O)(=O)c1ccc(CNC(=S)Nc2cccc(I)c2)cc1]

$^1$H NMR (400 MHz, DMSO) δ 9.83 (s, 1H), 8.44 (s, 1H), 7.92 (s, 1H), 7.77 (d, J=8.4 Hz, 2H), 7.48-7.40 (m, 4H), 7.32 (s, 2H), 7.11 (t, J=8.0 Hz, 1H), 4.79 (d, J=5.2 Hz, 2H); MS (ESI), 447.9 (M+H)$^+$.

Example 8

4-(2-(3-(3-iodophenyl)thioureido)ethyl)benzenesulfonamide (MIP-1186)

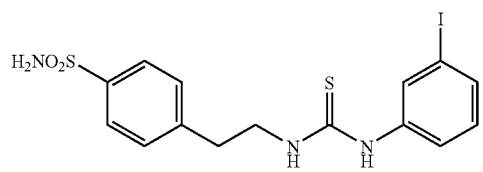

$^1$H NMR (400 MHz, DMSO) δ 9.62 (s, 1H), 7.91 (brs, 1H), 7.86 (s, 1H), 7.76 (d, J=8.4 Hz, 2H), 7.44 (d, J=8.0 Hz, 3H), 7.31 (brs, 3H), 7.08 (t, J=8.0 Hz, 1H), 3.71 (brs, 2H), 2.95 (t, J=7.2 Hz, 2H); MS (ESI), 462.0 (M+H)$^+$.

Example 9

4-(2-(3-(2-iodophenyl)thioureido)ethyl)benzenesulfonamide (MIP-1188)

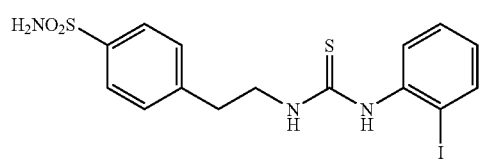 [SMILES: NS(=O)(=O)c1ccc(CCNC(=S)Nc2ccccc2I)cc1]

$^1$H NMR (400 MHz, DMSO) δ 9.12 (s, 1H), 7.87 (d, J=8.0 Hz, 1H), 7.76 (d, J=8.4 Hz, 3H), 7.43 (d, J=8.4 Hz, 2H), 7.39-7.35 (m, 2H), 7.30 (s, 2H), 7.03-6.99 (m, 1H), 3.68 (brs, 2H), 2.95 (t, J=7.0 Hz, 2H); MS (ESI), 462.3 (M+H)$^+$.

Example 10

4-(2-(3-(4-iodophenyl)thioureido)ethyl)benzenesulfonamide (MIP-1189)

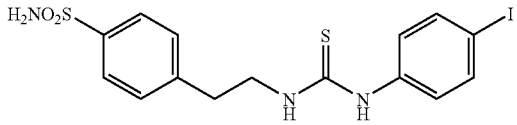 [SMILES: NS(=O)(=O)c1ccc(CCNC(=S)Nc2ccc(I)cc2)cc1]

$^1$H NMR (400 MHz, DMSO) δ 9.61 (s, 1H), 7.86 (brs, 1H), 7.76 (d, J=8.0 Hz, 2H), 7.62 (d, J=8.0 Hz, 2H), 7.43 (d, J=8.0

Hz, 2H), 7.31 (s, 2H), 7.19 (d, J=8.0 Hz, 2H), 3.72-3.69 (m, 2H), 2.94 (t, J=7.4 Hz, 2H); MS (ESI), 462.3 (M+H)⁺.

Example 11

4-((3-(2-iodophenyl)thioureido)methyl)benzene-sulfonamide (MIP-1190)

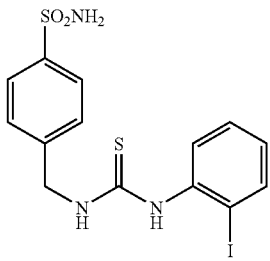 [SMILES: NS(=O)(=O)c1ccc(CNC(=S)Nc2ccccc2I)cc1]

¹H NMR (400 MHz, DMSO) δ 9.34 (s, 1H), 8.19 (brs, 1H), 7.89 (d, J=8.0 Hz, 1H), 7.76 (d, J=8.4 Hz, 2H), 7.49 (d, J=8.0 Hz, 2H), 7.41-7.38 (m, 2H), 7.31 (s, 2H), 7.06-7.02 (m, 1H), 4.78 (d, J=4.4 Hz, 2H); MS (ESI), 448.2 (M+H)⁺.

Example 12

4-((3-(4-iodophenyl)thioureido)methyl)benzene-sulfonamide (MIP-1191)

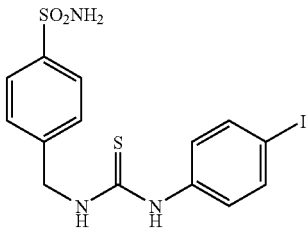 [SMILES: NS(=O)(=O)c1ccc(CNC(=S)Nc2ccc(I)cc2)cc1]

¹H NMR (400 MHz, DMSO) δ 9.78 (s, 1H), 8.35 (s, 1H), 7.77 (d, J=8.4 Hz, 2H), 7.65 (d, J=8.4 Hz, 2H), 7.45 (d, J=8.0 Hz, 2H), 7.31 (s, 2H), 7.27 (d, J=8.8 Hz, 2H), 4.78 (d, J=5.2 Hz, 2H); MS (ESI), 448.2 (M+H)⁺.

Example 13

4-(3-(4-iodophenyl)ureido)benzenesulfonamide (MIP-1192)

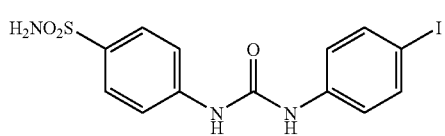 [SMILES: NS(=O)(=O)c1ccc(NC(=O)Nc2ccc(I)cc2)cc1]

¹H NMR (400 MHz, DMSO) δ 9.10 (s, 1H), 8.92 (s, 1H), 7.71 (d, J=8.8 Hz, 2H), 7.61 (d, J=8.8 Hz, 2H), 7.59 (d, J=8.8 Hz, 2H), 7.31 (d, J=8.8 Hz, 2H), 7.21 (s, 2H); MS (ESI), 418.2 (M+H)⁺.

Example 14

4-(3-(3-iodophenyl)ureido)benzenesulfonamide (MIP-1193)

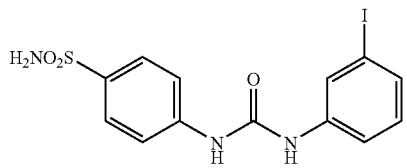 [SMILES: NS(=O)(=O)c1ccc(NC(=O)Nc2cccc(I)c2)cc1]

¹H NMR (400 MHz, DMSO) δ 9.12 (s, 1H), 8.92 (s, 1H), 8.01 (t, J=1.8 Hz, 1H), 7.72 (d, J=8.8 Hz, 2H), 7.60 (d, J=8.8 Hz, 2H), 7.34 (dd, J=8.0, 2.0 Hz, 2H), 7.21 (s, 2H), 7.09 (t, J=8.0 Hz, 1H); MS (ESI), 418.2 (M+H)⁺.

Example 15

4 4-(3-(5-iodo-2-methoxyphenyl)thioureido)benze-nesulfonamide (MIP-1195)

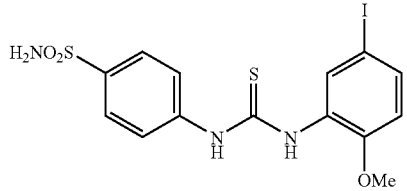 [SMILES: COc1ccc(I)cc1NC(=S)Nc1ccc(S(N)(=O)=O)cc1]

¹H NMR (400 MHz, DMSO) δ 10.30 (s, 1H), 9.43 (s, 1H), 8.23 (d, J=1.6 Hz, 1H), 7.73 (s, 4H), 7.49 (dd, J=8.4, 1.6 Hz, 1H), 7.30 (s, 2H), 6.91 (d, J=8.4 Hz, 1H), 3.82 (s, 3H); MS (ESI), 464.1 (M+H)⁺.

Example 16

4-(3-(2-iodophenyl)ureido)benzenesulfonamide (MIP-1196)

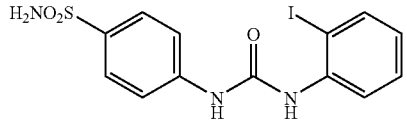 [SMILES: NS(=O)(=O)c1ccc(NC(=O)Nc2ccccc2I)cc1]

¹H NMR (400 MHz, DMSO) δ 9.77 (s, 1H), 8.01 (s, 1H), 7.84 (dd, J=8.0, 1.6 Hz, 1H), 7.80 (dd, J=8.0, 1.6 Hz, 1H), 7.73 (d, J=8.8 Hz, 2H), 7.62 (d, J=8.8 Hz, 2H), 7.36 (td, J=8.0, 1.6 Hz, 1H), 7.22 (s, 2H), 6.88 (td, J=8.0, 1.6 Hz, 1H); MS (ESI), 418.2 (M+H)+.

Example 17

4-(2-(3-(2-iodophenyl)ureido)ethyl)benzenesulfonamide (MIP-1197)

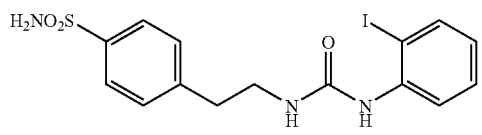 [SMILES: NS(=O)(=O)c1ccc(CCNC(=O)Nc2ccccc2I)cc1]

MS (ESI), 446.4 (M+H)+.

Example 18

4-(3-(3-fluoro-5-iodophenyl)thioureido)benzenesulfonamide (MIP-1199)

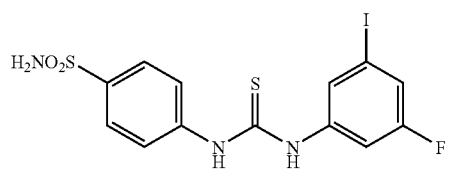 [SMILES: NS(=O)(=O)c1ccc(NC(=S)Nc2cc(F)cc(I)c2)cc1]

$^1$H NMR (400 MHz, CD$_3$OD) δ 7.77 (d, J=8.4 Hz, 2H), 7.62-7.59 (m, 3H), 7.38 (dt, J=10.8, 2.0 Hz, 1H), 7.22-7.19 (m, 1H); MS (ESI), 452.1 (M+H)+.

Example 19

4-(3-(3-iodo-4-methylphenyl)thioureido)benzenesulfonamide (MIP-1200)

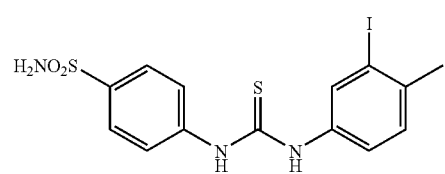 [SMILES: Cc1ccc(NC(=S)Nc2ccc(S(N)(=O)=O)cc2)cc1I]

$^1$H NMR (400 MHz, CD$_3$OD) δ 7.86 (s, 1H), 7.75 (d, J=8.4 Hz, 2H), 7.59 (d, J=8.0 Hz, 2H), 7.26 (d, J=8.0 Hz, 1H), 7.17 (d, J=8.0 Hz, 1H), 2.31 (s, 3H); MS (ESI), 448.2 (M+H)+.

Example 20

4-(2-(3-(3-iodophenyl)ureido)ethyl)benzenesulfonamide (MIP-1201)

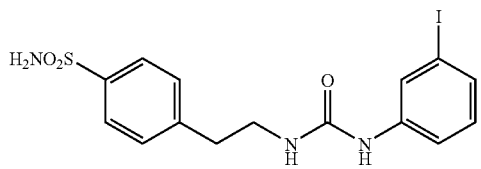

$^1$H NMR (400 MHz, CD$_3$OD) δ 7.78-7.73 (m, 3H), 7.33 (d, J=8.0 Hz, 2H), 7.19 (d, J=8.0 Hz, 1H), 7.16 (d, J=8.0 Hz, 1H), 6.88 (t, J=8.0 Hz, 1H), 3.16 (t, J=7.2 Hz, 2H), 2.81 (t, J=7.2 Hz, 2H); MS (ESI), 446.2 (M+H)+.

Example 21

4-(3-(5-iodo-2-methylphenyl)thioureido)benzenesulfonamide (MIP-1202)

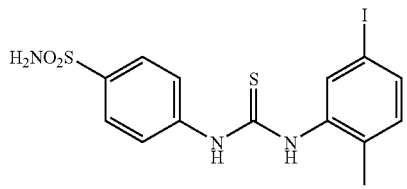 [SMILES: Cc1ccc(I)cc1NC(=S)Nc1ccc(S(N)(=O)=O)cc1]

$^1$H NMR (400 MHz, CD$_3$OD) δ 7.75 (d, J=8.8 Hz, 2H), 7.60 (d, J=8.8 Hz, 2H), 7.54 (d, J=1.6 Hz, 1H), 7.44 (d, J=8.0, 1.2 Hz, 1H), 6.95 (d, J=8.0 Hz, 1H), 2.17 (s, 3H); MS (ESI), 448.2 (M+H)+.

Example 22

4-((3-(3-iodophenyl)ureido)methyl)benzenesulfonamide (MIP-1203)

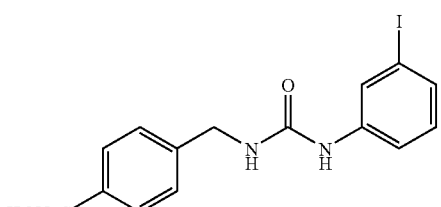

$^1$H NMR (400 MHz, CD$_3$OD) δ 7.79 (t, J=1.8 Hz, 1H), 7.76 (d, J=8.4 Hz, 2H), 7.39 (d, J=8.4 Hz, 2H), 7.22-7.19 (m, 2H), 6.90 (t, J=8.0 Hz, 1H), 4.35 (s, 2H); MS (ESI), 432.3 (M+H)+.

Example 23

Tricarbonyl Rhenium(I) 4-(3-(8-(bis(pyridin-2-ylmethyl)amino)octyl)thioureido)-benzenesulfonamide (MIP-1140)

To a suspension of 4-isothiocyanatobenzenesulfonamide (11 mg, 0.05 mmol) in dry acetonitrile (1 mL) and triethylamine (15 μL, 0.11 mmol) was added tricarbonyl rhenium(I) 6-(bis(pyridin-2-ylmethyl)amino)hexylamine trifluoroacetate (40 mg, 0.48 mmol). The reaction mixture was stirred for 3 h at room temperature. The reaction mixture was concentrated and the resulting solid recrystallized from methanol/water to afford MIP-1140 as an off-white solid (38 mg, 96%). $^1$H NMR (400 MHz, DMSO-$d_6$) δ 9.83 (br, 1H), 8.80 (d, J=5.4 Hz, 2H), 8.11 (br, 1H), 7.96 (m, 2H), 7.86-7.25 (m, 10H), 4.90 (m, 4H) 3.72 (m, 2H), 3.47 (br, 2H), 1.83 (br, 2H), 1.57 (m, 2H), 1.37 (bm, 8H); (M+H)$^+$ (811).

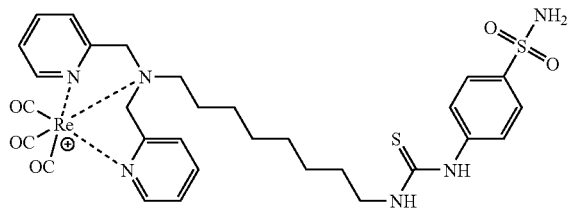

Example 24

4-(3-(2-fluoro-4-iodophenyl)thioureido)benzenesulfonamide (MIP-1147)

The subject compound was prepared utilizing the procedure described above from 4-isothiocyanatobenzenesulfonamide and 2-fluoro-4-iodoaniline. $^1$H NMR (400 MHz, DMSO-$d_6$) δ 10.35 (s, 1H), 9.77 (s, 1H), 7.86-7.37 (m, 7H), 7.29 (bs, 2H); (M+H)$^+$ (452).

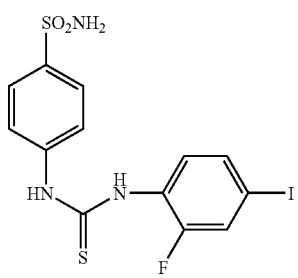 [SMILES: NS(=O)(=O)c1ccc(NC(=S)Nc2ccc(I)cc2F)cc1]

Example 25

4-(3-(2-iodophenyl)thioureido)benzenesulfonamide (MIP-1148)

The subject compound was prepared utilizing the procedure described above from 4-isothiocyanatobenzenesulfonamide and 2-iodoaniline. $^1$H NMR (400 MHz, DMSO-$d_6$) δ 10.16 (s, 1H), 9.60 (s, 1H), 7.90-7.81 (m, 8H), 7.76 (bs, 2H); (M+H)$^+$ (434).

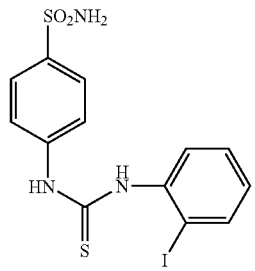 [SMILES: NS(=O)(=O)c1ccc(NC(=S)Nc2ccccc2I)cc1]

Example 26

4-(3-(4-iodophenyl)thioureido)benzenesulfonamide (MIP-1149)

The subject compound was prepared utilizing the procedure described above from 4-isothiocyanatobenzenesulfonamide and 4-iodoaniline. $^1$H NMR (400 MHz, DMSO-$d_6$) δ 10.13 (s, 1H), 10.08 (s, 1H), 7.76-7.65 (m, 6H), 7.32 (d, J=8.8 Hz, 2H), 7.29 (bs, 2H); (M+H)$^+$ (434).

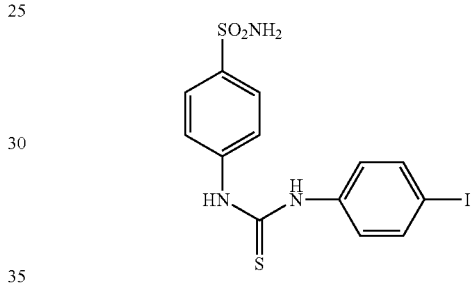

The following 3-thioureabenzenesulfonamides were prepared by methods illustrated in the following scheme as modified from the method described in Casini et al., *Journal of Enzyme Inhibition and Medicinal Chemistry,* 2002, Vol. 17 (5), 333-343.

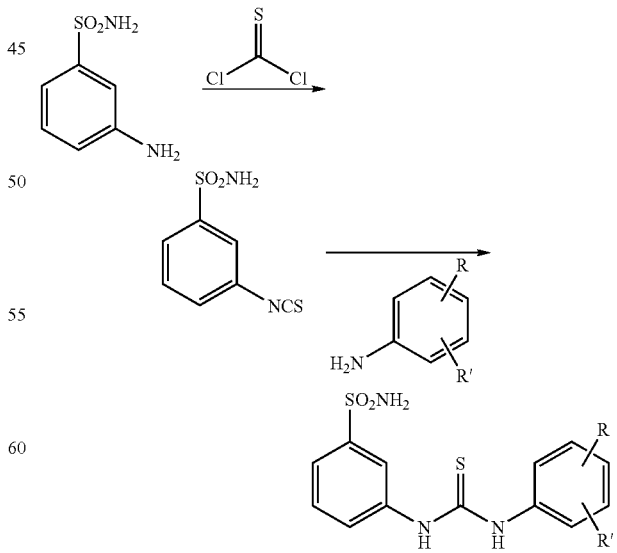

In general, an appropriate substituted aniline was added to a suspension of 3-isothiocyanato-benzenesulfonamide (2.0 mmol) in dry acetonitrile (10 mL) and the reaction was stirred at room temperature for 3 h. The reaction mixture was concentrated and the obtained crude solids were recrystallized from acetone-water to obtain the desired 3-thioureabenzensulfonamides as white to off-white solids in yields ranging from 45-95%.

Example 27

3-(3-(2-fluoro-4-iodophenyl)thioureido)benzenesulfonamide (MIP-1150)

The subject compound was prepared utilizing the procedure described above from 3-isothiocyanatobenzenesulfonamide and 2-fluoro-4-iodoaniline. $^1$H NMR (400 MHz, DMSO-$d_6$) δ 10.19 (s, 1H), 9.67 (s, 1H), 7.96 (m, 1H), 7.70 (m, 2H), 7.58-7.49 (m, 3H), 7.38 (bs, 3H); (M+H)$^+$ (452).

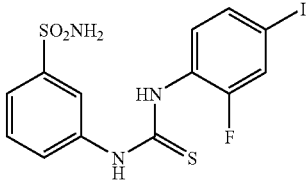 [SMILES: NS(=O)(=O)c1cccc(NC(=S)Nc2ccc(I)cc2F)c1]

Example 28

3-(3-(2-iodophenyl)thioureido)benzenesulfonamide (MIP-1151)

The subject compound was prepared utilizing the procedure described above from 3-isothiocyanatobenzenesulfonamide and 2-iodoaniline. $^1$H NMR (400 MHz, DMSO-$d_6$) δ 10.07 (s, 1H), 9.52 (s, 1H), 8.01-7.37 (m, 9H), 7.04 (m, 1H); (M+H)$^+$ (434).

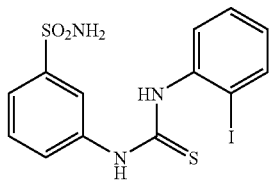 [SMILES: NS(=O)(=O)c1cccc(NC(=S)Nc2ccccc2I)c1]

Example 29

3-(3-(4-iodophenyl)thioureido)benzenesulfonamide (MIP-1152)

The subject compound was prepared utilizing the procedure described above from 3-isothiocyanatobenzenesulfonamide and 4-iodoaniline. $^1$H NMR (400 MHz, DMSO-$d_6$) δ 10.07 (s, 1H), 10.01 (s, 1H), 7.94 (m, 1H), 7.71-7.48 (m, 5H), 7.37 (bs, 2H), 7.31 (d, J=8.5 Hz, 2H); (M+H)$^+$ (434).

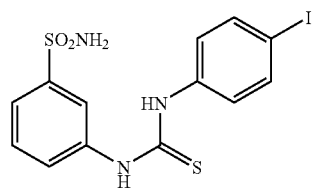 [SMILES: NS(=O)(=O)c1cccc(NC(=S)Nc2ccc(I)cc2)c1]

The following indanesulfonamides were prepared from N-(5-sulfamoyl-2,3-dihydro-1H-inden-1-yl)acetamide which was commercially available from ChemPacific, Inc. in Baltimore, Md. N-(5-sulfamoyl-2,3-dihydro-1H-inden-1-yl)acetamide may also be prepared via chlorosulfonation of acetylated aminoindane followed by conversion of the resulting sulfonyl chloride to the desired sulfonamide, as shown below.

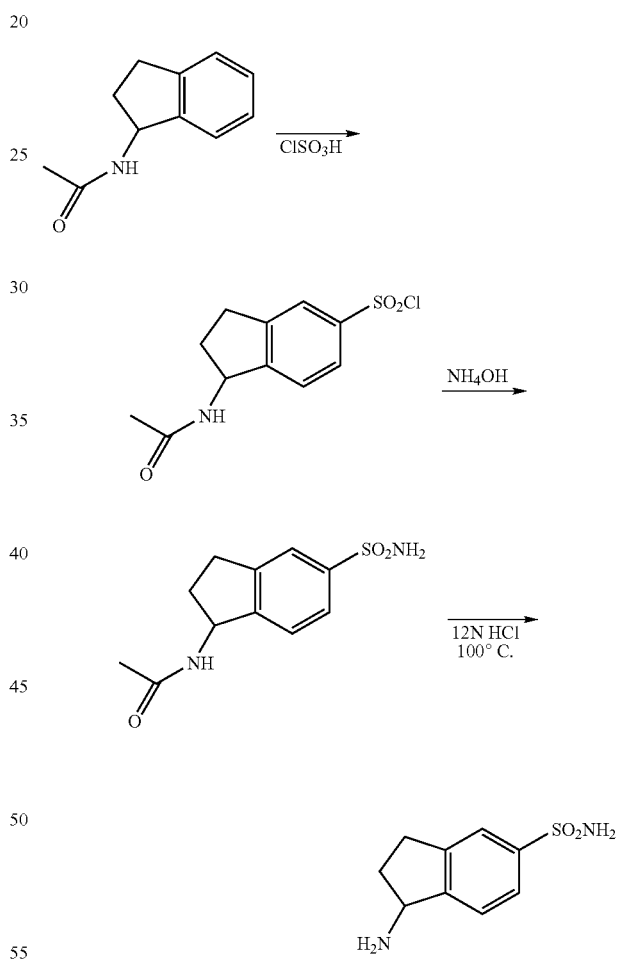

Example 30

N-(5-sulfamoyl-2,3-dihydro-1H-inden-1-yl)acetamide (MIP-1154)

$^1$H NMR (400 MHz, DMSO-$d_6$) δ 8.30 (m, 1H), 7.64 (m, 2H), 7.39 (m, 1H), 7.29 (br, 2H), 5.30 (m, 1H), 3.10-2.79 (m, 2H), 2.42-2.38 (m, 2H), 1.89 (s, 3H); (M+H)$^+$ (254).

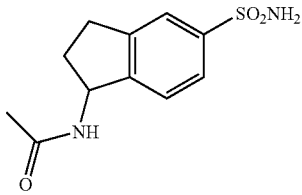 [SMILES: CC(=O)NC1CCc2cc(S(N)(=O)=O)ccc21]

Example 31

1-Amino-2,3-dihydro-1H-indene-5-sulfonamide hydrochloride salt (MIP-1153)

To a round bottom flask containing N-(5-sulfamoyl-2,3-dihydro-1H-inden-1-yl)acetamide (1 g, 3.9 mmol) was added 12N hydrochloric acid (100 mL) and the reaction was heated to a reflux for 2 days. The reaction was cooled and concentrated to afford MIP-1153 (785 mg, 96%) as a light tan solid. $^1$H NMR (400 MHz, DMSO-d$_6$) δ 7.46-7.20 (m, 3H), 3.78 (br, 6H), 3.21-1.97 (m, 4H); (M+H)$^+$ (212).

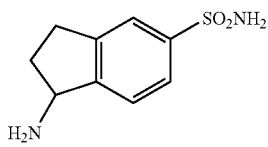 [SMILES: NC1CCc2cc(S(N)(=O)=O)ccc21]

Example 32

4-iodo-N-(5-sulfamoyl-2,3-dihydro-1H-inden-1-yl)benzamide (MIP-1146)

To a round bottom flask containing 1-amino-2,3-dihydro-1H-indene-5-sulfonamide hydrochloride salt (93 mg, 0.38 mmol) suspended in dichloromethane (3 mL) was added triethylamine (61 μL) followed by 4-iodobenzoylchloride (100 mg, 0.38 mmol) and the reaction was stirred overnight at room temperature. The reaction was diluted with dischloromethane (25 mL) and washed with 10% aqueous hydrochloric acid (10 mL), water (10 mL), brine (10 mL), dried over sodium sulfate and concentrated to afford the crude material as an off-white solid. Recrystallization from ethanol/water afforded MIP-1146 (19 mg, 21%) as a white solid. $^1$H NMR (400 MHz, DMSO-d$_6$) δ 8.96 (m, 2H), 7.85-7.35 (m, 8H), 5.60 (m, 1H), 3.15-2.75 (m, 2H), 2.15-1.90 (m, 2H); (M+H)$^+$ (443).

Example 33

4-iodo-N-(5-sulfamoyl-1,3,4-thiadiazol-2-yl)benzamide

To a solution of 5-amino-1,3,4-thiadiazole-2-sulfonamide (0.133 g, 0.50 mmol) in pyridine (5.0 mL) was added 4-iodobenzoyl chloride (0.162 g, 0.75 mmol). The reaction mixture was stirred at room temperature for overnight under nitrogen. Solvent was concentrated and water (60 mL) was added the mixture. The precipitated sulfonamide was filtered and dried over vacuum to give desired compound (27.3 mg, 13%) as a white solid.

$^1$H NMR (400 MHz, DMSO) δ 13.12 (brs, 1H), 7.91 (d, J=8.4 Hz, 2H), 7.88 (d, J=8.4 Hz, 2H); MS (ESI), 411 (M+H)$^+$.

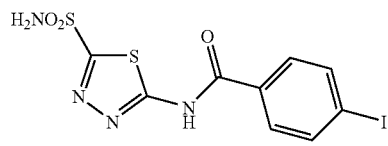 [SMILES: NS(=O)(=O)c1nnc(NC(=O)c2ccc(I)cc2)s1]

Example 34

5-(3-(3-iodophenyl)thioureido)-1,3,4-thiadiazole-2-sulfonamide

To a solution of 1-iodo-3-isothiocyanatobenzene (0.13 g, 0.50 mmol) in acetonitrile (10 mL) was added 5-amino-1,3,4-thiadiazole-2-sulfonamide (0.108 g, 0.50 mmol) and anhydrous K$_2$CO$_3$ (0.40 g). The mixture was stirred at 75° C. for 4 hrs. Solvent was evaporated and diluted with water. The precipitated solid was filtered and dried over vacuum to give desired compound (99 mg, 45%) as a white solid. $^1$H NMR (400 MHz, DMSO) δ 8.99 (brs, 1H), 8.24 (brs, 1H), 7.78 (d, J=8.0 Hz, 1H), 7.69 (t, J=1.8 Hz, 1H), 7.35 (m, 1H), 7.26 (t, J=7.8 Hz, 1H), 7.02 (s, 2H).

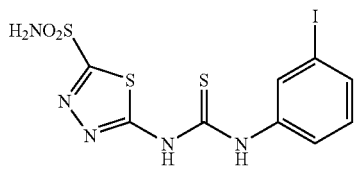 [SMILES: NS(=O)(=O)c1nnc(NC(=S)Nc2cccc(I)c2)s1]

Example 35

General Technetium-99m Radiolabeling Procedure and Radiolabeling of MIP-1162

Figure 1A:
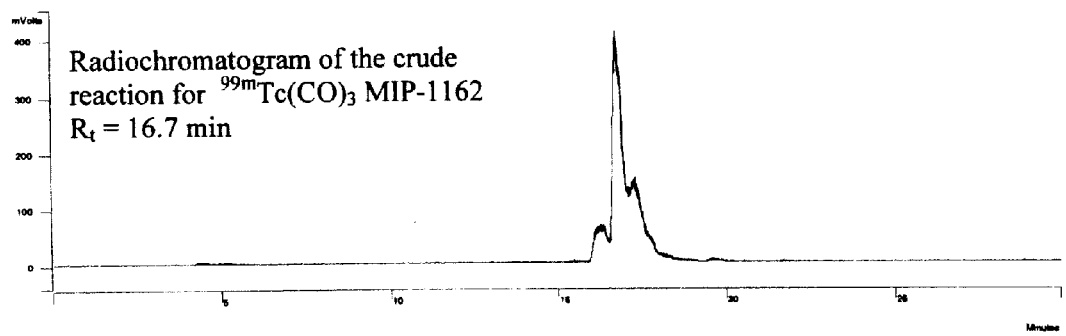
FIGS. 1A and 1B are graphs showing a radiochromatogram of $^{99m}$Tc(CO)$_3$ MIP-1162 and an UV-Visible trace of Re(CO)$_3$ MIP-1162 in accordance with one embodiment of the present invention.
Figure 1B:
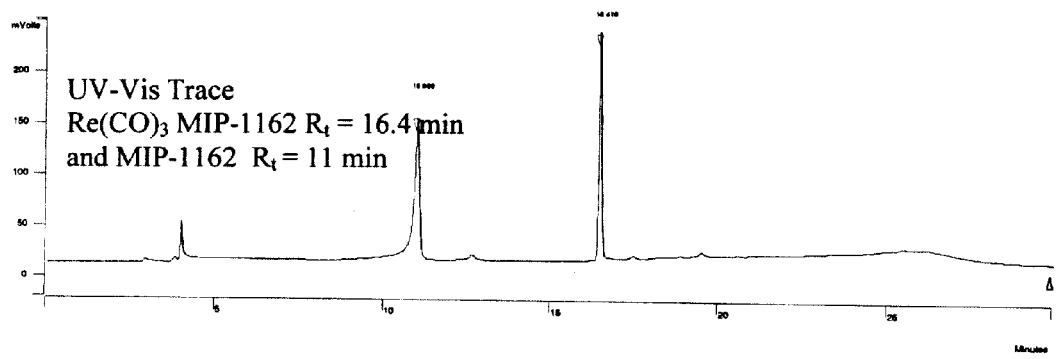

[$^{99m}$Tc(CO)$_3$(H$_2$O)$_3$]$^+$ was prepared by the methods known in the art using the Isolink® radiolabeling kits available from Tyco Healthcare, St. Louis, Mo. Sodium Pertechnetate, 7400 MBq (200 mCi), in saline (2.5 mL) was added to an Isolink® radiolabeling kit and the vial was placed in an oil bath at 100° C. The reaction was heated for 45 minutes and 1N HCl (200 μL) was then added to neutralize the reaction mixture. The product, [$^{99m}$Tc(CO)$_3$(H$_2$O)$_3$]$^+$, was removed from the vial via syringe and added to another vial containing MIP-1162 (200 μL of a 1 mg/mL solution in methanol) followed by an additional amount of methanol (0.3 mL). The reaction was heated for 1 hour at 80° C. and the crude reaction was injected on the HPLC to determine radiochemical yield (RCY) (72%). $^{99m}$Tc(CO)$_3$ MIP-1162 and Re MIP-1162 were co-injected to show that the desired product was present (FIG. 1).

Example 36

2-((2-((carboxymethyl)(2-(4-iodophenylamino)-2-oxoethyl)amino)ethyl)-(2-oxo-2-(4-sulfamoylphenylamino)ethyl)amino)acetic Acid (MIP-1222)

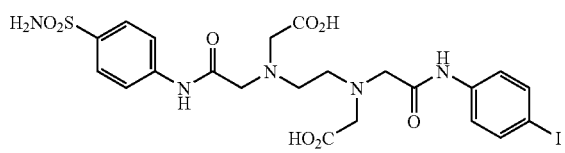 [SMILES: NS(=O)(=O)c1ccc(NC(=O)CN(CCN(CC(=O)O)CC(=O)Nc2ccc(I)cc2)CC(=O)O)cc1]

A solution of EDTA dianhydride (256 mg, 1.0 mmol) and sulfanilamide (172 mg, 1.0 mmol) in DMF (10.0 mL) was stirred at room temperature for 4 h. 4-Iodoaniline (219 mg, 1.0 mmol) was added to the reaction mixture and the resulting reaction mixture was stirred at room temperature for at least 12 hours (overnight). The solvent was evaporated under reduced pressure and purified over AmberChrom™ resin eluting with CH$_3$CN/water to give the title compound (35.4 mg, 5.5%) as a white solid. $^1$H NMR (400 MHz, DMSO) δ 10.41 (brs, 1H), 10.19 (s, 1H), 7.79 (d, J=8.0 Hz, 2H), 7.73 (d, J=8.0 Hz, 2H), 7.61 (d, J=8.8 Hz, 2H), 7.47 (d, J=8.8 Hz, 2H), 7.24 (s, 2H), 3.50-3.46 (m, 8H), 2.80 (s, 4H); MS (ESI), 648 (M+H)$^+$.

Example 37

2-((2-((carboxymethyl)(2-(4-iodophenylamino)-2-oxoethyl)amino)ethyl)-(2-oxo-2-(4-sulfamoylphenethylamino)ethyl)amino)acetic Acid (MIP-1227)

The title compound was prepared by following the same procedure as described in the preparation of Example 36, except 4-(2-aminoethyl)benzenesulfonamide was used in place of sulfanilamide. $^1$H NMR (400 MHz, DMSO) δ 10.19 (s, 1H), 8.37 (brs, 1H), 7.73 (d, J=8.4 Hz, 2H), 7.65 (d, J=8.8 Hz, 2H), 7.45 (d, J=8.8 Hz, 2H), 7.36 (d, J=8.4 Hz, 2H), 7.30 (s, 2H), 3.70-3.30 (m, 10H), 3.05 (brs, 4H), 2.78 (t, J=7.4 Hz, 2H); MS (ESI), 676 (M+H)$^+$.

Example 38

2-((2-((carboxymethyl)(2-(4-iodophenylamino)-2-oxoethyl)amino)ethyl)-(2-oxo-2-(4-sulfamoylbenzylamino)ethyl)amino)acetic Acid (MIP-1244)

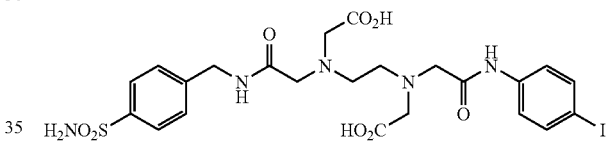

The title compound was prepared by following the same procedure as described in the preparation of Example 36, except 4-(aminomethyl)benzenesulfonamide was used in place of sulfanilamide. $^1$H NMR (400 MHz, DMSO) δ 10.25 (s, 1H), 8.88 (brs, 1H), 7.76 (d, J=8.4 Hz, 2H), 7.64 (d, J=8.8 Hz, 2H), 7.44 (s, 2H), 7.42 (s, 2H), 7.33 (s, 2H), 4.38 (d, J=5.6 Hz, 2H), 3.95-3.74 (m, 10H), 3.16 (brs, 4H); MS (ESI), 662 (M+H)$^+$.

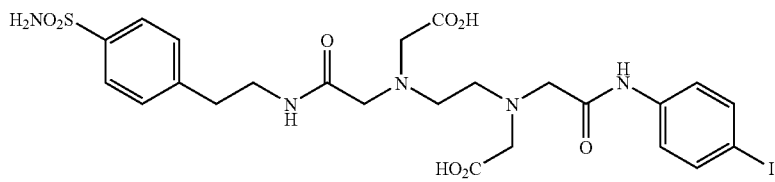 [SMILES: NS(=O)(=O)c1ccc(CCNC(=O)CN(CCN(CC(=O)O)CC(=O)Nc2ccc(I)cc2)CC(=O)O)cc1]

Example 39

2-((2-((carboxymethyl)(2-(4-iodophenylamino)-2-oxoethyl)amino)ethyl)-(2-oxo-2-(4-(3-(4-sulfamoylphenyl)thioureido)phenylamino)ethyl)amino) acetic Acid (MIP-1249)

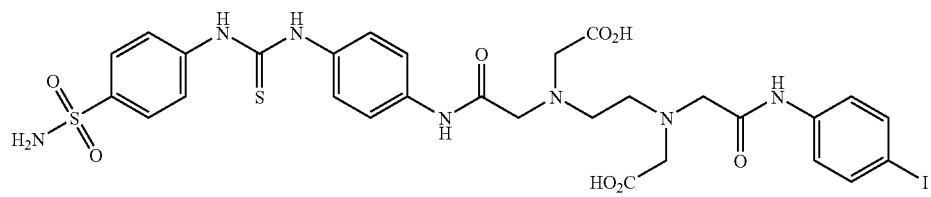 [SMILES: NS(=O)(=O)c1ccc(NC(=S)Nc2ccc(NC(=O)CN(CCN(CC(=O)O)CC(=O)Nc3ccc(I)cc3)CC(=O)O)cc2)cc1]

Step 1. Preparation of 4-(3-(4-aminophenyl)thioureido)benzenesulfonamide

To a solution of 1,4-diaminobenzene (0.324 g, 3.0 mmol) in acetonitrile was added 4-isothiocyanatobenzenesulfonamide (0.642 g, 3.0 mmol). The mixture was stirred at room temperature for 3 h. The reaction mixture went clear and a white precipitate formed. The solid was filtered, washed with acetonitrile and dried to afford 4-(3-(4-aminophenyl)thioureido)-benzenesulfonamide as a white sold (0.829 g, 86%). $^1$H NMR (400 MHz, DMSO) δ 9.65 (s, 2H), 7.71 (d, J=8.8 Hz, 2H), 7.66 (d, J=8.8 Hz, 2H), 7.26 (s, 2H), 7.00 (d, J=8.4 Hz, 2H), 6.52 (d, J=6.8 Hz, 2H), 5.08 (s, 2H); MS (ESI), 323 (M+H)$^+$.

Step 2. Preparation of 2-((2-((carboxymethyl)(2-(4-iodophenylamino)-2-oxoethyl)amino)ethyl)-(2-oxo-2-(4-(3-(4-sulfamoylphenyl)thioureido)phenylamino) ethyl)amino)acetic Acid (MIP-1249)

The title compound was prepared by following the same procedure as described in Example 36, except 4-(3-(4-aminophenyl)thioureido)benzenesulfonamide was used in place of sulfanilamide. $^1$H NMR (400 MHz, DMSO) δ 10.31 (s, 1H), 10.28 (s, 1H), 10.09 (s, 1H), 10.04 (s, 1H), 7.76 (d, J=8.8 Hz, 2H), 7.69 (d, J=8.8 Hz, 2H), 7.65 (d, J=8.8 Hz, 2H), 7.56 (d, J=8.8 Hz, 2H), 7.43 (t, J=8.6 Hz, 4H), 7.31 (s, 2H), 4.00-3.60 (m, 10H), 3.24 (s, 4H); MS (ESI), 798 (M+H)$^+$.

Example 40

4-(3-(4-(3-(3-iodophenyl)thioureido)phenyl)thioureido)benzene-sulfonamide (MIP-1230)

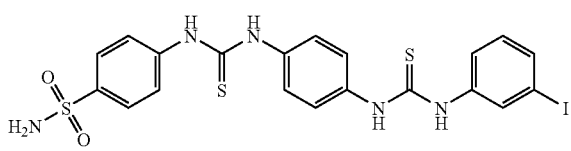 [SMILES: NS(=O)(=O)c1ccc(NC(=S)Nc2ccc(NC(=S)Nc3cccc(I)c3)cc2)cc1]

To a solution of 4-(3-(4-aminophenyl)thioureido)benzenesulfonamide (0.322 g, 1.0 mmol) in acetonitrile was added 1-iodo-3-isothiocyanatobenzene (0.261 g, 1.0 mmol). The mixture was stirred at room temperature overnight. The solvent was evaporated under reduced pressure and water was added into the crude reaction mixture. The precipitate which formed was filtered, and dried to afford the title product as a white solid (0.452 g, 78%). $^1$H NMR (400 MHz, DMSO) δ 10.05 (s, 1H), 10.02 (s, 1H), 9.90 (s, 1H), 9.81 (s, 1H), 7.94 (t, J=1.8 Hz, 1H), 7.74 (d, J=8.8 Hz, 2H), 7.68 (d, J=8.8 Hz, 2H), 7.48-7.41 (m, 5H), 7.12 (t, J=8.0 Hz, 1H); MS (ESI), 584 (M+H)$^+$.

Example 41

(S)-5-((S)-4-carboxy-1-(4-iodobenzylamino)-1-oxobutan-2-ylamino)-5-oxo-4-(3-(4-sulfamoylphenyl)thioureido)pentanoic acid (MIP-1228)

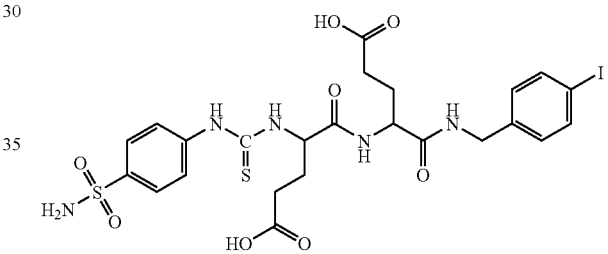

Step 1. Preparation of (S)-methyl 4-(tert-butoxycarbonylamino)-5-(4-iodobenzylamino)-5-oxopentanoate A solution of 4-iodobenzylamine hydrochloride (2.965 g, 11.0 mmol), Boc-Glu(OMe)-OH.DCHA (4.426 g, 10.0 mmol), EDCI (2.301 g, 10.0 mmol), HOBt (1.351 g, 10.0 mmol) in DCM (100 mL) containing DIPEA (5.23 mL) was stirred at room temperature under nitrogen for 20 h. The reaction mixture was diluted with DCM, washed with 1N HCl, sat. NaHCO$_3$ solution, and brine. The solvent was evaporated under reduced pressure to give a crude product, which was purified by flash chromatography eluting with hexane/ethyl acetate (3:1) to give (S)-methyl 4-(tert-butoxycarbonylamino)-5-(4-iodobenzylamino)-5-oxopentanoate (3.653 g, 77%) as a white solid. $^1$H NMR (400 MHz, CDCl$_3$) δ 7.65 (d, J=8.4 Hz, 2H), 7.00 (d, J=8.4 Hz, 2H), 6.65 (s, 1H), 5.24 (brs, 1H), 4.39 (t, J=5.4 Hz, 2H), 4.15 (m, 1H), 3.70 (s, 3H), 2.57-2.37 (m, 2H), 2.20-2.11 (m, 1H), 1.99-1.90 (m, 1H), 1.44 (s, 9H); MS (ESI), 499 (M+Na)$^+$.

Step 2. Preparation of (S)-methyl 4-(tert-butoxycarbonylamino)-5-((S)-1-(4-iodobenzylamino)-5-methoxy-1,5-dioxopentan-2-ylamino)-5-oxopentanoate A solution of (S)-methyl 4-(tert-butoxycarbonylamino)-5-(4-iodobenzylamino)-5-oxopentanoate (2.129 g, 4.47 mmol)

in DCM (15 mL) and TFA (10 mL) was stirred at room temperature for 4 h. After the solvent was evaporated, the reaction mixture was diluted with DCM, washed with sat. K₂CO₃ aqueous solution and concentrated in vacuo to afford (S)-methyl 4-amino-5-(4-iodobenzylamino)-5-oxopentanoate (1.67 g). A solution of (S)-methyl 4-amino-5-(4-iodobenzylamino)-5-oxopentanoate (1.67 g), Boc-Glu(OMe)—OH.DCHA (1.97 g, 4.44 mmol), EDCI (1.02 g, 5.33 mmol), HOBt (0.599 g, 4.44 mmol) in DCM (100 mL) containing DIPEA (2.26 mL) was stirred at room temperature under nitrogen for 20 h. The reaction mixture was diluted with DCM, washed with 1N HCl aqueous solution, sat. NaHCO₃ aqueous solution and brine. The organic phase was separated and evaporated under reduced pressure to give a crude product, which was purified by flash chromatography with hexane/ethyl acetate as eluent to give (S)-methyl 4-(tert-butoxycarbonylamino)-5-((S)-1-(4-iodobenzylamino)-5-methoxy-1,5-dioxopentan-2-ylamino)-5-oxopentanoate (2.137 g, 77% over 2 steps) as a white solid. ¹H NMR (400 MHz, CDCl₃) δ 7.62 (d, J=8.4 Hz, 2H), 7.20 (s, 1H), 7.00 (d, J=8.4 Hz, 2H), 5.44 (brs, 1H), 4.48-4.30 (m, 3H), 4.06-4.02 (m, 1H), 3.69 (s, 6H), 2.54-2.37 (m, 4H), 2.20-1.93 (m, 3H), 1.37 (s, 9H); MS (ESI), 620 (M+H)⁺.

Step 3. Preparation of (S)-methyl 5-(4-iodobenzylamino)-4-((S)-5-methoxy-5-oxo-2-(3-(4-sulfamoylphenyl)thioureido)pentanamido)-5-oxopentanoate A solution of (S)-methyl 4-(tert-butoxycarbonylamino)-5-((S)-1-(4-iodobenzylamino)-5-methoxy-1,5-dioxopentan-2-ylamino)-5-oxopentanoate (0.448 g, 0.723 mmol) in DCM (10 mL) and TFA (4.0 mL) was stirred at room temperature overnight. After the solvent was evaporated, the reaction mixture was diluted with DCM, washed with sat. K₂CO₃ and concentrated in vacuo to afford (S)-methyl 4-amino-5-((S)-1-(4-iodobenzylamino)-5-methoxy-1,5-dioxopentan-2-ylamino)-5-oxopentanoate. A solution of the above product ((S)-methyl 4-amino-5-((S)-1-(4-iodobenzylamino)-5-methoxy-1,5-dioxopentan-2-ylamino)-5-oxopentanoate), 4-isothiocyanatobenzenesulfonamide (0.171 g, 0.80 mmol) in acetonitrile (10 mL) containing DIPEA (0.40 mL) was stirred at room temperature under nitrogen for 48 h. The solvent was evaporated under reduced pressure to give a crude product, which was purified by flash chromatography 5% MeOH in DCM as eluent to give (S)-methyl 5-(4-iodobenzylamino)-4-((S)-5-methoxy-5-oxo-2-(3-(4-sulfamoylphenyl)thioureido)pentanamido)-5-oxopentanoate (0.469 g) as a white solid. MS (ESI), 756 (M+Na)⁺, 377 (M/2+H)⁺.

Step 4. (S)-5-((S)-4-carboxy-1-(4-iodobenzylamino)-1-oxobutan-2-ylamino)-5-oxo-4-(3-(4-sulfamoylphenyl)thioureido)pentanoic Acid A solution of (S)-methyl 5-(4-iodobenzylamino)-4-((S)-5-methoxy-5-oxo-2-(3-(4-sulfamoylphenyl)thioureido)pentanamido)-5-oxopentanoate (0.200 g, 0.27 mmol) and lithium hydroxide (48 mg) in methanol (3.0 mL) and water (1.0 mL) was stirred at room temperature for overnight. The reaction mixture was purified by HPLC to give the title product (49.4 mg) as a yellow solid. MS (ESI), 728 (M+Na)⁺.

Example 42

4-(3-(4-(2-(2-(2-(4-((4-iodophenoxy)methyl)-1H-1,2,3-triazol-1-yl)ethoxy)ethoxy)-ethoxy)phenyl)thioureido)benzenesulfonamide (MIP-1229)

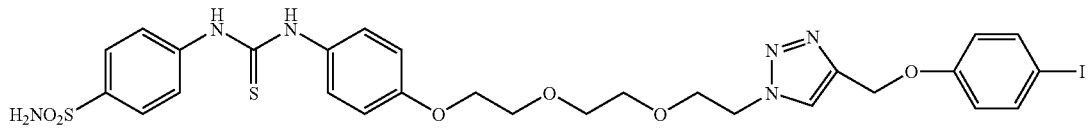 [SMILES: NS(=O)(=O)c1ccc(NC(=S)Nc2ccc(OCCOCCOCCn3cc(COc4ccc(I)cc4)nn3)cc2)cc1]

Step 1. Preparation of tert-butyl 4-(2-(2-(2-azidoethoxy)ethoxy)ethoxy)phenylcarbamate A suspension of tert-butyl 4-hydroxyphenylcarbamate (1.24 g, 5.93 mmol), 2-(2-(2-azidoethoxy)ethoxy)ethyl 4-methylbenzenesulfonate (1.50 g, 4.56 mmol) and K₂CO₃ (2.45 g, 17.79 mmol) in acetonitrile was stirred at 80° C. overnight. The reaction mixture was filtered and washed with acetonitrile. After the solvent was evaporated, the reaction mixture was diluted with DCM. The DCM solution was washed with sat. K₂CO₃ aqueous solution and brine. The organic phase was dried, and concentrated in vacuo to afford tert-butyl 4-(2-(2-(2-azidoethoxy)ethoxy)ethoxy)phenylcarbamate (1.88 g, 100%). ¹H NMR (400 MHz, CDCl₃) δ 7.26 (d, J=8.8 Hz, 2H), 6.86 (d, J=8.8 Hz, 2H), 6.35 (s, 1H), 4.10 (t, J=4.8 Hz, 2H), 3.85 (t, J=4.8 Hz, 2H), 3.76-3.62 (m, 6H), 3.39 (t, J=5.2 Hz, 2H), 1.52 (s, 9H); MS (ESI), 389 (M+Na)⁺.

Step 2. Preparation of tert-butyl 4-(2-(2-(2-(4-((4-iodophenoxy)methyl)-1H-1,2,3-triazol-1-yl)ethoxy)ethoxy)ethoxy)phenylcarbamate To a solution of tert-butyl 4-(2-(2-(2-azidoethoxy)ethoxy)ethoxy)phenylcarbamate (1.78 g, 4.86 mmol) and 1-iodo-4-(prop-2-ynyloxy)benzene (1.25 g, 4.86 mmol) in THF (30 mL) was added H₂O (8.0 mL), Cu powder (0.31 g, 4.86 mmol) and CuSO₄ (0.12 g, 0.486 mmol). The reaction mixture was stirred at room temperature for at least 12 hours (overnight). The reaction mixture was filtered through celite and washed with EtOAc. The organic layer was separated, washed with EDTA solution, dried and concentrated in vacuo to give a crude product which was purified by flash chromatography with hexane/EtOAc (1:1) as eluent to give tert-butyl 4-(2-(2-(2-(4-((4-iodophenoxy)methyl)-1H-1,2,3-triazol-1-yl)ethoxy)ethoxy)ethoxy)phenylcarbamate (2.069 g, 68%). ¹H NMR (400 MHz, CDCl₃) δ 7.74 (s, 1H), 7.46 (d, J=9.2 Hz, 2H), 7.15 (d, J=8.8 Hz, 2H), 6.74 (d, J=9.2 Hz, 2H), 6.66 (d, J=8.8 Hz, 2H), 6.25 (brs, 1H), 5.04 (s, 2H), 4.47 (t, J=5.0 Hz, 2H), 3.99 (t, J=4.8 Hz, 2H), 3.79 (t, J=5.0 Hz, 2H), 3.80 (t, J=5.0 Hz, 2H), 3.71 (t, J=5.0 Hz, 2H), 3.60-3.53 (m, 4H), 1.44 (s, 9H); MS (ESI), 625 (M+H)⁺.

Step 3. Preparation of 4-(3-(4-(2-(2-(2-(4-((4-iodophenoxy)methyl)-1H-1,2,3-triazol-1-yl)ethoxy)ethoxy)-ethoxy)phenyl)thioureido)benzenesulfonamide The title compound was prepared by following the same procedure as described in step 3 of Example 6, except tert-butyl 4-(2-(2-(2-(4-((4-iodophenoxy)methyl)-1H-1,2,3-triazol-1-yl)ethoxy)ethoxy)ethoxy)phenylcarbamate was used in place of (S)-methyl 4-(tert-butoxycarbonylamino)-5-((S)-1-(4-iodobenzylamino)-5-methoxy-1,5-dioxopentan-2-ylamino)-5-oxopentanoate. $^1$H NMR (400 MHz, DMSO) δ 10.00 (s, 1H), 9.93 (s, 1H), 8.18 (s, 1H), 7.74 (d, J=8.8 Hz, 2H), 7.68 (d, J=8.8 Hz, 2H), 7.58 (d, J=8.8 Hz, 2H), 7.32 (d, J=8.8 Hz, 2H), 7.27 (s, 2H), 6.88 (t, J=5.6 Hz, 2H), 5.09 (s, 2H), 4.52 (t, J=5.2 Hz, 2H), 4.00 (t, J=4.8 Hz, 2H), 3.81 (t, J=5.0 Hz, 2H), 3.68 (t, J=5.0 Hz, 2H), 3.63-3.57 (m, 4H); MS (ESI), 739 (M+H)$^+$.

Example 43

4-(5-iodopyridin-2-yl)-N-(4-sulfamoylphenyl)piperazine-1-carbothioamide (MIP-1238)

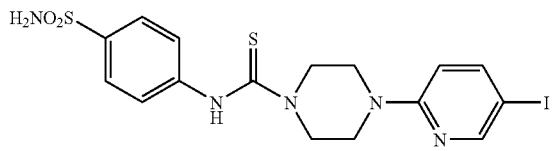 [SMILES: C[N+]1(c2ccc(I)cn2)CCN(C(=S)Nc2ccc(S(N)(=O)=O)cc2)CC1]

To a solution of 1-(5-iodopyridin-2-yl)piperazine (0.360 g, 1.247 mmol) in acetonitrile (40 mL) was added sulfanilamide (0.266 g, 1.247 mmol). The mixture was stirred at 50° C. for 7 h. The reaction mixture which went clear formed a white precipitate. The solid was filtered, washed with acetonitrile and dried to afford 4-(5-iodopyridin-2-yl)-N-(4-sulfamoylphenyl)piperazine-1-carbothioamide as a white sold (0.360 g, 57%). $^1$H NMR (400 MHz, DMSO) δ 9.60 (s, 1H), 8.28 (d, J=2.0 Hz, 1H), 7.81 (dd, J=8.8, 2.4 Hz, 1H), 7.70 (d, J=8.8 Hz, 2H), 7.48 (d, J=8.4 Hz, 2H), 7.27 (s, 2H), 6.76 (d, J=8.8 Hz, 1H), 4.02 (t, J=5.2 Hz, 4H), 3.62 (t, J=5.2 Hz, 4H); MS (ESI), 504 (M+H)$^+$.

Example 44

1-(5-iodopyridin-2-yl)-1-methyl-4-(4-sulfamoylphenylcarbamothioyl)piperazin-1-ium (MIP-1252)

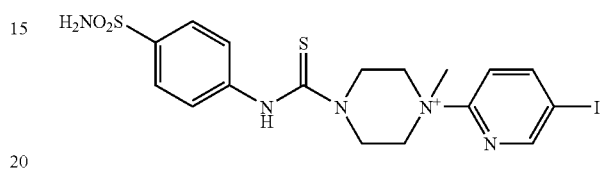

A solution of 4-(5-iodopyridin-2-yl)-N-(4-sulfamoylphenyl)piperazine-1-carbothioamide (100 mg, 0.20 mmol) and iodomethane (0.40 mL) in DMF (1.0 mL) was stirred at room temperature for 3 h. The reaction mixture was diluted with ether, the solid was filtered and washed with ether to give the title product (95 mg, 74%) as a white solid. $^1$H NMR (400 MHz, DMSO) δ 8.28 (d, J=2.4 Hz, 1H), 7.83 (dd, J=8.8, 2.4 Hz, 1H), 7.77 (d, J=8.4 Hz, 2H), 7.30-7.18 (m, 4H), 6.79 (d, J=9.2 Hz, 1H), 3.76-3.66 (m, 8H), 2.28 (s, 3H); MS (ESI), 518 M$^+$.

Example 45

General Iodine-123/131 Radiolabeling Procedure and Radiolabeling of MIP-1222

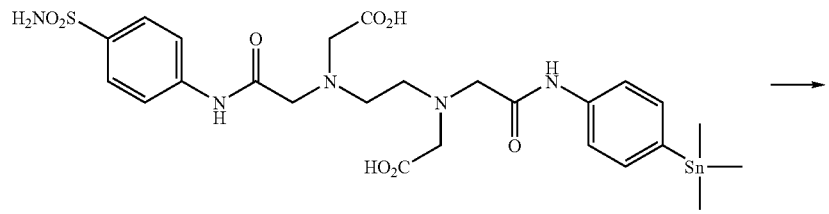

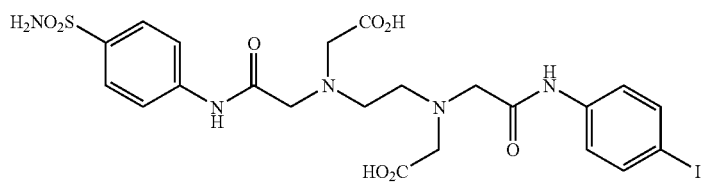

Into a 5 cc vial containing [$^{123}$I]—NaI or [13 I]—NaI (300 mCi) was added 100 µL of sterile water for injection (SWFI), followed by 305 µL of an acid solution [acetic acid (300 µL) and sulfuric acid (5 µL)], followed by 300 µL oxidant [acetic acid (0.2 mL) and 30% hydrogen peroxide (0.335 mL) brought to a final volume of 5 mL with SWFI], to which was added 100 µL of the trimethylstannane precursor of MIP-1222 (1 mg/mL solution in acetonitrile). The mixture was vortexed for 2 minutes and allowed to incubate at room temperature for an additional 10 minutes. The reaction was quenched with 200 µL of 0.1 M sodium thiosulfate. The radiochemical yields ranged from 50-70%, RCP>90% specific activity ≥4000 mCi/µmol by reverse-phase HPLC analysis.

Example 46

As a further illustration of the invention, the reader is referred to the following Tables of Compounds, which provide non-limiting, preferred embodiments.

TABLE 1

Formula I

Metal-Chelate—(—)$_m$—V—(—)$_n$—W—Z—S(=O)$_2$—NH$_2$

I

| Compound # | Metal | Chelate | V | W | Z | m | n |
|---|---|---|---|---|---|---|---|
| 1 | Re | DPA | bond | bond | phenylene | 0 | 0 |
| 2 | Re | DPA | bond | bond | thiadiazole | 0 | 0 |
| 3 | Re | DPA | bond | bond | phenylene | 0 | 1 |
| 4 | Re | DPA | bond | bond | phenylene | 0 | 2 |
| 5 | Re | DPA | bond | bond | thiadiazolene | 0 | 2 |
| 6 | Re | DPA | NH—C(O)(CH$_2$)$_2$—C(O)—NH— | bond | phenylene | 4 | 2 |
| 7 | Re | DPA | NH—C(O)(CH$_2$)$_2$—C(O)—NH— | bond | thiadiazolene | 4 | 2 |
| 8 | Tc | DPA | bond | bond | phenylene | 0 | 0 |
| 9 | Re | DPA | O | O | phenylene | 2 | 1 |
| 10 | Tc | DPA | C(O)—NH | bond | phenylene | 3 | 3 |
| 11 | Re | DPA | C(O)—NH | bond | thiadiazolene | 3 | 2 |
| 12 | Re | DPA | NH—C(S)—NH | bond | phenylene | 4 | 4 |
| 13 | Tc | DPA | NH—C(S)—NH | bond | thiadiazolene | 3 | 3 |
| 14 | Re | DPA | (OCH$_2$CH$_2$O)$_2$—CH$_2$CH$_2$—NH—C(S)—NH | bond | phenylene | 3 | 2 |
| 15 | Tc | DPA | (OCH$_2$CH$_2$O)$_2$—CH$_2$CH$_2$—NH—C(S)—NH | bond | thiadiazolene | 4 | 2 |
| 16 | Re | DPA | C(O)(CH$_2$)$_2$C(O)NH | bond | phenylene | 4 | 2 |
| 17 | Tc | DPA | C(O)—NH | bond | thiadiazolene | 4 | 0 |
| 18 | Tc | DPA | C(O)—NH | bond | indane | 3 | 0 |
| 19 | Re | DPA | C(O)(CH$_2$)$_2$C(O)NH | bond | indane | 4 | 0 |
| 20 | Tc | DPA | C(O)—NH | bond | indane | 3 | 0 |

TABLE 1-continued

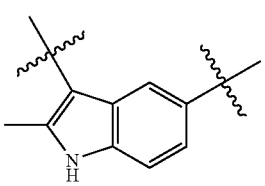 [SMILES: *c1ccc2[nH]c(C)c(*)c2c1]

Formula I

| Compound # | Metal | Chelate | V | W | Z | m | n |
|---|---|---|---|---|---|---|---|
| 21 | Re | DPA | bond | bond | (indole structure) | 2 | 0 |
| 22 | Tc | DPA | C(S)—NH | bond | phenylene | 0 | 0 |
| 23 | Re | DPA | C(S)—NH | bond | phenylene | 0 | 6 |
| 24 | Re | PAMA | bond | bond | phenylene | 0 | 0 |
| 25 | Tc | PAMA | bond | bond | phenylene | 0 | 0 |
| 26 | Re | PAMA | NH—C(S)—NH | bond | phenylene | 8 | 0 |
| 27 | Re | PAMA | C(O)—NH | bond | phenylene | 5 | 0 |
| 28 | Re | MTMA | bond | bond | phenylene | 0 | 0 |
| 29 | Re | MTMA | bond | bond | phenylene | 0 | 6 |
| 30 | Re | MTMA | NH—C(S)—NH | bond | phenylene | 8 | 0 |
| 31 | Re | MTMA | C(O)—NH | bond | phenylene | 5 | 0 |
| 32 | Re | DMI | bond | bond | phenylene | 0 | 0 |
| 33 | Re | DMI | bond | bond | phenylene | 0 | 6 |
| 34 | Re | DMI | NH—C(S)—NH | bond | phenylene | 8 | 0 |
| 35 | Re | DMI | C(O)—NH | bond | phenylene | 5 | 0 |
| 36 | Re | DMI | C(O)—NH | bond | phenylene | 10 | 0 |
| 37 | Re | DHI | bond | bond | phenylene | 0 | 0 |
| 38 | Tc | DHI | bond | bond | phenylene | 0 | 0 |
| 39 | Re | DHI | NH—C(S)—NH | bond | phenylene | 8 | 0 |
| 40 | Re | DHI | C(O)—NH | bond | phenylene | 5 | 0 |
| 41 | Re | DCMI | bond | bond | phenylene | 0 | 0 |
| 42 | Tc | DCMI | bond | bond | phenylene | 0 | 0 |
| 43 | Re | DCMI | NH—C(S)—NH | bond | phenylene | 8 | 0 |
| 44 | Re | DCMI | C(O)—NH | bond | phenylene | 5 | 0 |
| 45 | Re | DMEI | bond | bond | phenylene | 0 | 0 |
| 46 | Tc | DMEI | bond | bond | phenylene | 0 | 0 |
| 47 | Re | DMEI | NH—C(S)—NH | bond | phenylene | 8 | 0 |
| 48 | Re | DMEI | C(O)—NH | bond | phenylene | 5 | 0 |
| 49 | Re | DTK | bond | bond | phenylene | 0 | 0 |
| 50 | Tc | DTK | bond | bond | phenylene | 0 | 0 |
| 51 | Re | DTK | NH—C(S)—NH | bond | phenylene | 8 | 0 |
| 52 | Re | DTK | C(O)—NH | bond | phenylene | 5 | 0 |

Note:
In a preferred embodiment of the invention, the phenylene moiety may be linked to the rest of the molecule via a 1,3- or 1,4-disubstitution pattern. In another preferred embodiment of the invention, the thiadiazole is preferably a 1,3,4-thiadiazole with the 2-position of the thiadiazole being linked to the rest of the molecule bearing the sulfonamide group and the 5-position of the thiadiazole being linked to the rest of the molecule bearing the substituted phenyl group. Abbreviations: bis(2-pyridylmethylamine) (DPA); pyridine-2-ylmethylamino acetic acid (PAMA), bis(thiazol-2-ylmethyl)amine (DTK), and thiazol-2-ylmethylamino acetic acid (MTMA), bis(N-carboxymethylimidazoylamine) (DCMI), bis(N-1,1-dimethoxyethylimidazoylamine) (DMEI), bis(N-methylimidazoylamine) (DMI): bis(N-hydroxyethylimidazoylamine) (DHI).
The structures of these chelating moieties are depicted below:

TABLE 1-continued
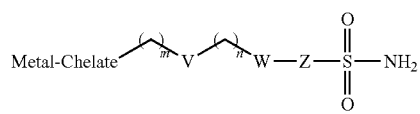
Formula I
| Compound # | Metal | Chelate | V | W | Z | m | n |
|---|---|---|---|---|---|---|---|
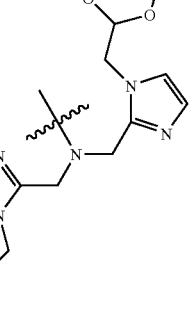
DMEI
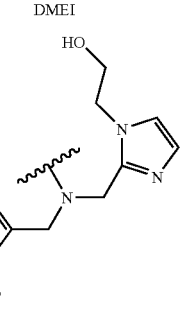
DHI
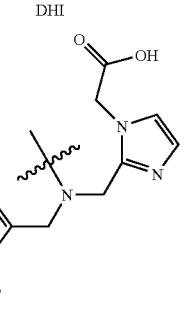
DCMI
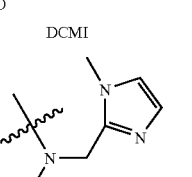
DMI TABLE 1-continued
Formula I
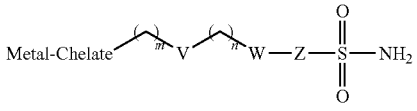
| Compound # | Metal Chelate | V | W | Z | m | n |
|---|---|---|---|---|---|---|
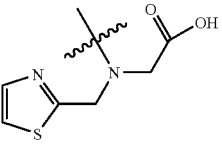
MTMA
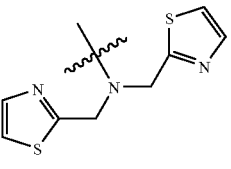
DTK
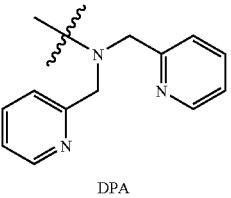 [SMILES: *N(Cc1ccccn1)Cc1ccccn1]
DPA
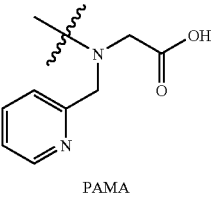 [SMILES: *N(CC(=O)O)Cc1ccccn1]
PAMA
TABLE 2
Formula II
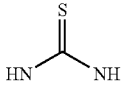
| Compound # | R1 | R2 | R3 | R4 | R5 | V1 | W1 | W |
|---|---|---|---|---|---|---|---|---|
| 1 | H | I | H | H | H | bond | 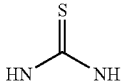 | bond |
| 2 | H | H | I | H | F | bond | (same as above) | bond |

TABLE 2-continued

| | | | | | | | | |
|---|---|---|---|---|---|---|---|---|
| 3 | H | H | H | H | I | bond | 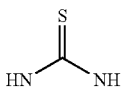 | bond |
| 4 | H | H | I | H | H | bond | 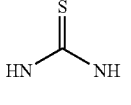 | bond |
| 5 | H | H | CO2H | H | I | bond | 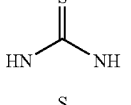 | bond |
| 6 | H | H | I | H | F | bond | 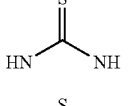 | bond |
| 7 | H | F | CH3 | I | OMe | bond | 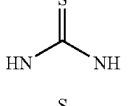 | bond |
| 8 | H | I | H | H | H | bond | 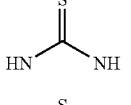 | bond |
| 9 | H | H | I | H | H | bond | 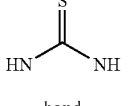 | bond |
| 10 | H | H | I | H | H | bond | bond | NH |
| 11 | H | H | I | H | H | bond | bond | NH |
| 12 | H | H | I | H | H | bond | bond | NH |
| 13 | F | H | I | H | H | bond | 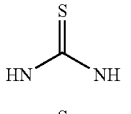 | bond |
| 14 | F | H | I | H | H | bond | 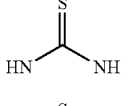 | bond |
| 15 | F | H | I | H | H | bond | 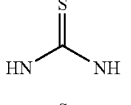 | bond |
| 16 | F | H | I | H | H | bond | 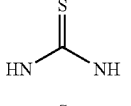 | bond |
| 17 | F | H | I | H | H | bond | 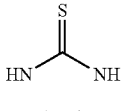 | bond |
| 18 | F | H | I | H | H | bond | bond | NH |
| 19 | F | H | I | H | H | bond | bond | NH |
| 20 | F | H | I | H | H | bond | bond | NH |
| 21 | F | H | I | H | H | bond | bond | NH |
| 22 | F | H | I | H | H | bond | bond | NH |
| 23 | F | H | I | H | H | bond | bond | NH |
| 24 | H | H | I | H | H | bond | bond | NH |
| 25 | F | H | I | H | H | bond | bond | NH |
| 26 | F | F | I | F | F | bond | bond | NH |

TABLE 2-continued
| | | | | | | | | |
|---|---|---|---|---|---|---|---|---|
| 27 | H | I | H | H | H | bond | 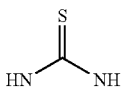 | bond |
| 28 | H | I | H | H | F | bond | 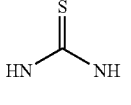 | bond |
| 29 | H | I | H | F | H | bond | 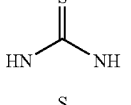 | bond |
| 30 | H | I | H | H | OMe | bond | 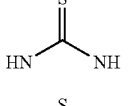 | bond |
| 31 | H | I | Me | H | H | bond | 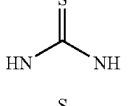 | bond |
| 32 | H | I | H | H | Me | bond | 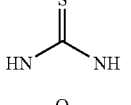 | bond |
| 33 | H | I | H | H | H | bond | 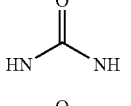 | bond |
| 34 | I | H | H | H | H | bond | 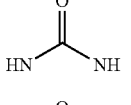 | bond |
| 35 | H | H | I | H | H | bond | 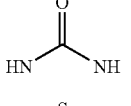 | bond |
| 36 | I | H | H | H | H | bond | 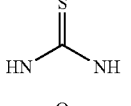 | bond |
| 37 | I | H | H | H | H | bond | 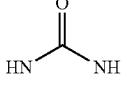 | bond |
| 38 | H | I | H | H | H | bond | 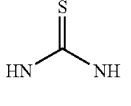 | bond |
| 39 | H | I | H | H | H | bond | 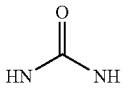 | bond |
| 40 | H | H | I | H | H | bond | 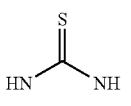 | bond |
| 41 | H | H | I | H | H | bond | 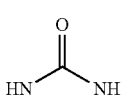 | bond |
| 42 | I | H | H | H | H | bond | 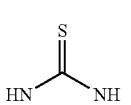 | bond |

TABLE 2-continued

| | | | | | | | | |
|---|---|---|---|---|---|---|---|---|
| 43 | I | H | H | H | | bond | urea | bond |
| 44 | H | I | H | H | | bond | thiourea | bond |
| 45 | H | I | H | H | | bond | urea | bond |
| 46 | H | H | I | H | | bond | thiourea | bond |
| 47 | H | H | I | H | | bond | urea | bond |
| 48 | H | I | H | H | CO$_2$H | bond | thiourea | bond |
| 49 | H | I | OMe | H | H | bond | thiourea | bond |
| 50 | H | H | I | H | H | DTPA-linker | NH | NH |
| 51 | H | H | I | H | H | DTPA-linker | NH | NH |
| 52 | H | H | I | H | H | DTPA-linker | NH | NH |
| 53 | H | H | I | H | H | DTPA-linker | NH | NH |
| 54 | H | H | H | I | H | bond | thiourea | bond |

TABLE 2-continued
| 55 | H | H | I | H | H | 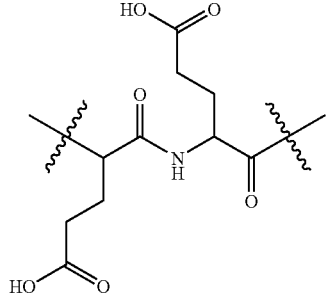 [SMILES: *C(=O)C(CCC(=O)O)NC(=O)C(*)CCC(=O)O] | NH | bond |
| 56 | H | H | I | H | H | 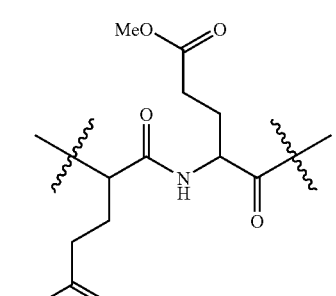 | NH | bond |
| 57 | H | H | I | H | H | 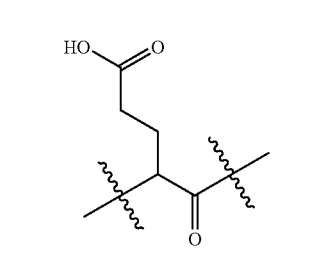 [SMILES: *C(=O)C(*)CCC(=O)O] | NH | bond |
| 58 | H | H | I | H | H | 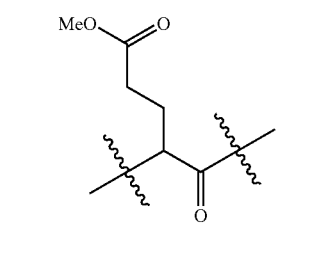 [SMILES: *C(=O)C(*)CCC(=O)OC] | NH | bond |
| 59 | H | H | I | H | H | 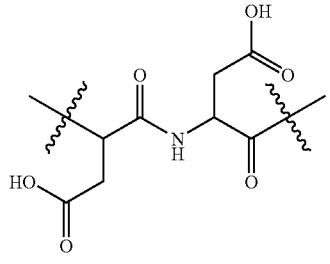 [SMILES: *C(=O)C(CC(=O)O)NC(=O)C(*)CC(=O)O] | NH | bond |
| 60 | H | H | I | H | H | 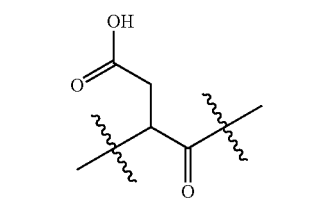 [SMILES: *C(=O)C(*)CC(=O)O] | NH | bond |

TABLE 2-continued
| 61 | H | H | I | H | H | 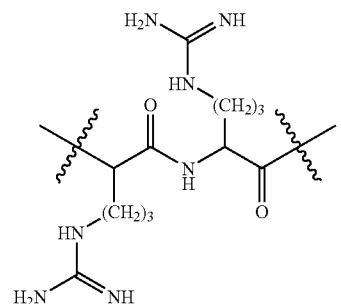 | NH | bond |
| 62 | H | H | I | H | H | 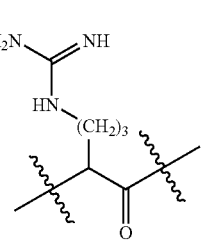 | NH | bond |
| Compound # | W2 | Z | Z1 | m | n |
|---|---|---|---|---|---|
| 1 | bond | 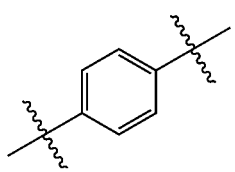 [SMILES: *c1ccc(*)cc1] | bond | 1 | 0 |
| 2 | bond | 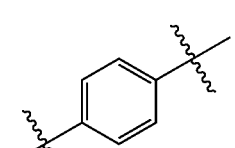 | bond | 0 | 0 |
| 3 | bond | 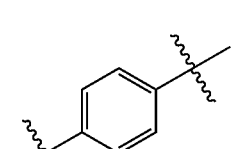 | bond | 0 | 0 |
| 4 | bond | 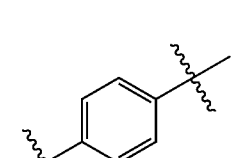 | bond | 0 | 0 |
| 5 | bond | 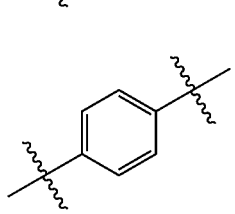 | bond | 2 | 0 |

TABLE 2-continued
| | | | | | |
|---|---|---|---|---|---|
| 6 | bond | 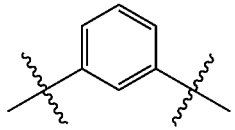 [SMILES: *c1cccc(*)c1] | bond | 0 | 0 |
| 7 | bond | 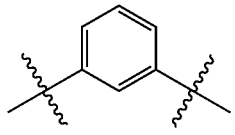 [SMILES: *c1cccc(*)c1] | bond | 1 | 0 |
| 8 | bond | 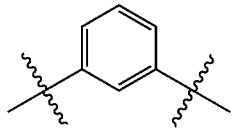 [SMILES: *c1cccc(*)c1] | bond | 0 | 0 |
| 9 | bond | 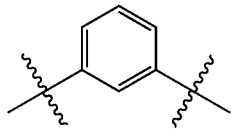 [SMILES: *c1cccc(*)c1] | bond | 0 | 0 |
| 10 | C=O | 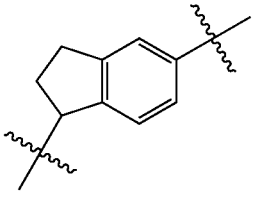 [SMILES: *c1ccc2c(c1)CCC2*] | bond | 0 | 0 |
| 11 | C=O | thiadiazole | bond | 0 | 0 |
| 12 | C=O | 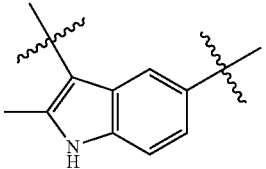 [SMILES: *c1ccc2[nH]c(C)c(*)c2c1] | bond | 0 | 0 |
| 13 | bond | thiadiazole | bond | 0 | 0 |
| 14 | bond | thiadiazole | bond | 1 | 0 |
| 15 | bond | thiadiazole | bond | 2 | 0 |
| 16 | bond | thiadiazole | bond | 3 | 0 |
| 17 | bond | thiadiazole | bond | 4 | 0 |
| 18 | C=O | thiadiazole | bond | 0 | 2 |
| 19 | C=O | thiadiazole | bond | 1 | 0 |
| 20 | C=O | thiadiazole | bond | 2 | 0 |
| 21 | C=O | thiadiazole | bond | 3 | 0 |
| 22 | C=O | thiadiazole | bond | 4 | 0 |
| 23 | C=O | 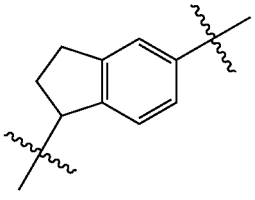 [SMILES: *c1ccc2c(c1)CCC2*] | bond | 0 | 0 |

TABLE 2-continued
| | | | | | | |
|---|---|---|---|---|---|---|
| 24 | C=O | 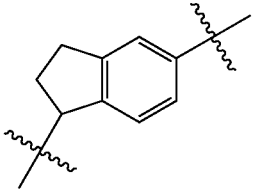 [SMILES: *c1ccc2c(c1)CCC2*] | bond | 0 | 0 |
| 25 | C=O | 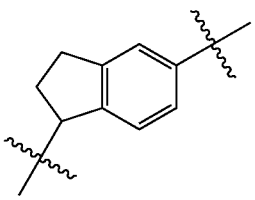 [SMILES: *c1ccc2c(c1)CCC2*] | bond | 0 | 0 |
| 26 | C=O | 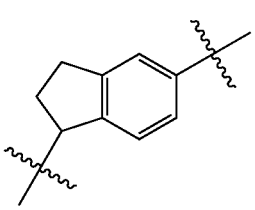 [SMILES: *c1ccc2c(c1)CCC2*] | bond | 0 | 0 |
| 27 | bond | 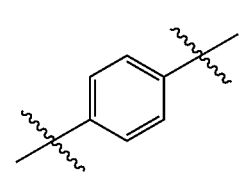 | bond | 0 | 0 |
| 28 | bond | 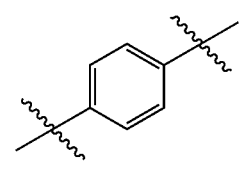 | bond | 0 | 0 |
| 29 | bond | 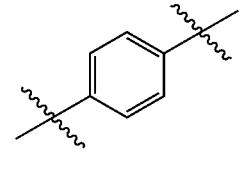 [SMILES: *c1ccc(*)cc1] | bond | 0 | 0 |
| 30 | bond | 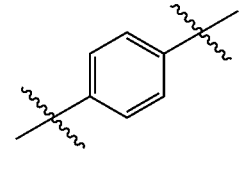 [SMILES: *c1ccc(*)cc1] | bond | 0 | 0 |
| 31 | bond | 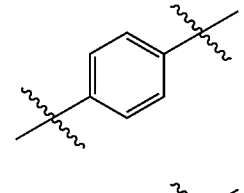 | bond | 0 | 0 |
| 32 | bond | 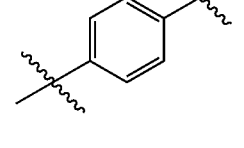 | bond | 0 | 0 |

TABLE 2-continued
| | | | | | |
|---|---|---|---|---|---|
| 33 | bond | 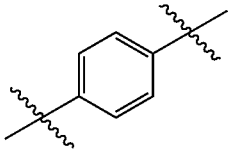 [SMILES: *c1ccc(*)cc1] | bond | 0 | 0 |
| 34 | bond | 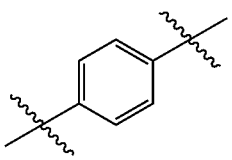 | bond | 0 | 0 |
| 35 | bond | 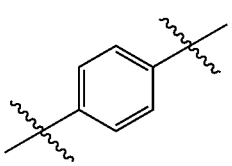 | bond | 0 | 0 |
| 36 | bond | 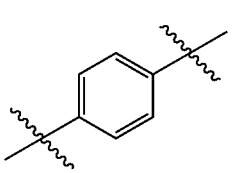 [SMILES: *c1ccc(*)cc1] | bond | 0 | 1 |
| 37 | bond | 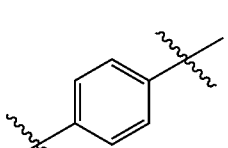 | bond | 0 | 1 |
| 38 | bond | 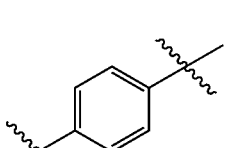 | bond | 0 | 1 |
| 39 | bond | 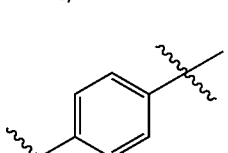 | bond | 0 | 1 |
| 40 | bond | 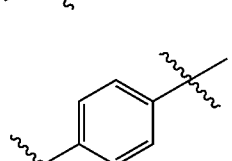 | bond | 0 | 1 |
| 41 | bond | 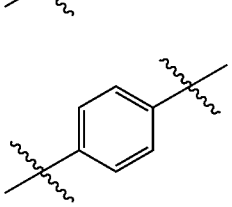 | bond | 0 | 1 |

TABLE 2-continued
| | | | | | | |
|---|---|---|---|---|---|---|
| 42 | bond | 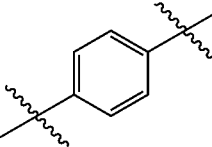 | bond | 0 | 2 |
| 43 | bond | 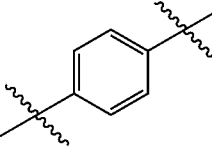 | bond | 0 | 2 |
| 44 | bond | 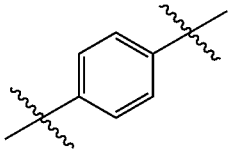 | bond | 0 | 2 |
| 45 | bond | 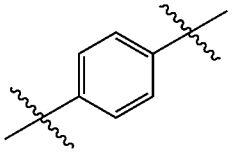 [SMILES: *c1ccc(*)cc1] | bond | 0 | 2 |
| 46 | bond | 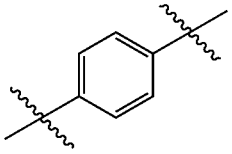 [SMILES: *c1ccc(*)cc1] | bond | 0 | 2 |
| 47 | bond | 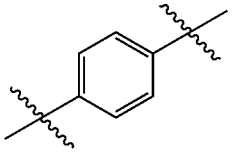 [SMILES: *c1ccc(*)cc1] | bond | 0 | 2 |
| 48 | bond | 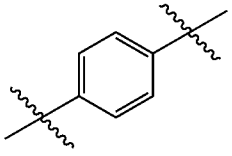 [SMILES: *c1ccc(*)cc1] | bond | 0 | 0 |
| 49 | bond | 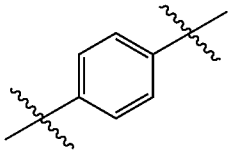 [SMILES: *c1ccc(*)cc1] | bond | 0 | 0 |
| 50 | bond | 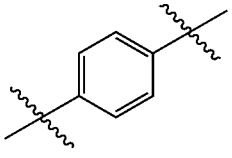 [SMILES: *c1ccc(*)cc1] | bond | 0 | 0 |

TABLE 2-continued
| | | | | | | |
|---|---|---|---|---|---|---|
| 51 | bond | 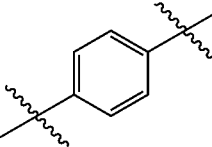 | | bond | 0 | 2 |
| 52 | bond | 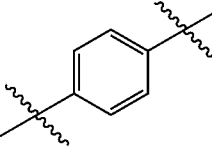 | | bond | 0 | 1 |
| 53 | 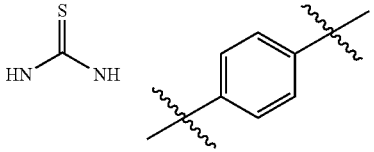 | 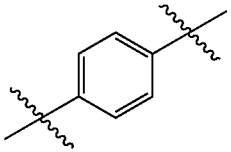 | 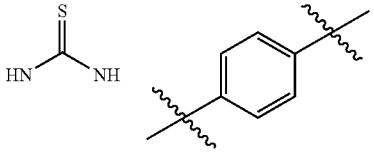 | | 0 | 0 |
| 54 | 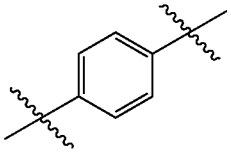 [SMILES: *c1ccc(*)cc1] | 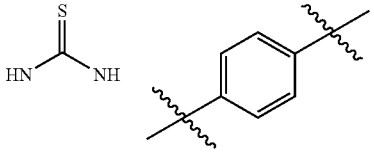 | 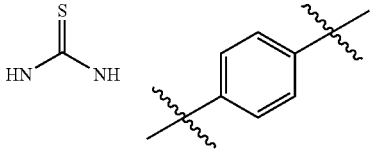 | | 0 | 0 |
| 55 | 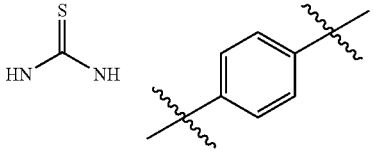 | 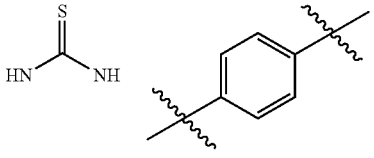 | | bond | 1 | 0 |
| 56 | 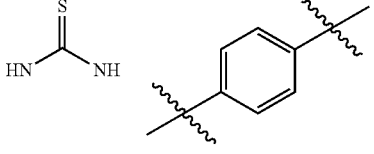 | | | bond | 1 | 0 |
| 57 | | | | bond | 1 | 0 |
| 58 | | | | bond | 1 | 0 |
| 59 | | | | bond | 1 | 0 |

TABLE 2-continued

| # | | | W1 | m | n |
|---|---|---|---|---|---|
| 60 | 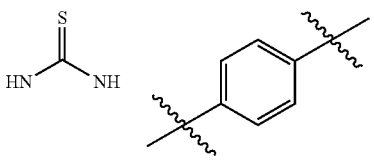 | 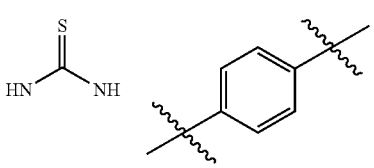 | bond | 1 | 0 |
| 61 | 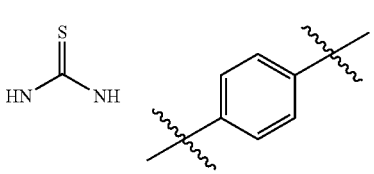 | 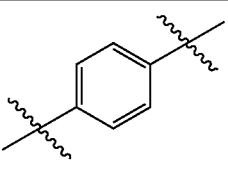 | bond | 1 | 0 |
| 62 | 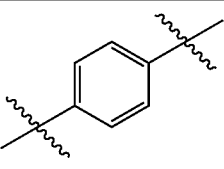 | 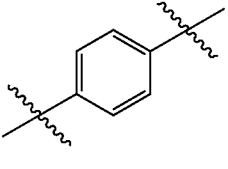 | bond | 1 | 0 |

Note:
In a preferred embodiment of the invention, the thiadiazole is preferably a 1,3,4-thiadiazole with the 2-position of the thiadiazole being linked to the rest of the molecule bearing the sulfonamide group and the 5-position of the thiadiazole being linked to the rest of the molecule bearing the substituted phenyl group.

TABLE 3

Formula III

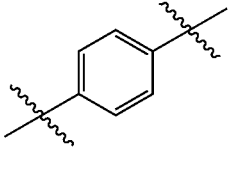 [SMILES: *c1ccc(*)cc1]

| Compound # | R1 | R2 | R3 | R4 | R5 | V1 | V2 | W1 | Z | Z1 | m | n | y |
|---|---|---|---|---|---|---|---|---|---|---|---|---|---|
| 1 (MIP-1229) | H | H | I | H | H | O | O—(CH$_2$CH$_2$O)$_2$ | NHC(S)NH | 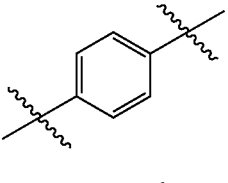 | 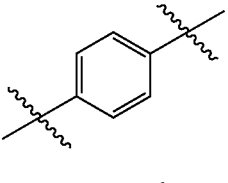 | 1 | 0 | 2 |
| 2 | H | H | I | H | H | O | O—(CH$_2$CH$_2$O)$_2$ | NHC(S)NH | 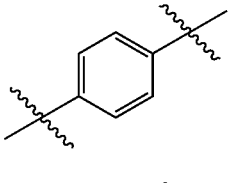 | 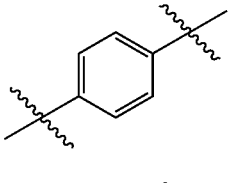 | 1 | 0 | 3 |
| 3 | H | H | I | H | H | O | OCH$_2$CH$_2$O | NHC(S)NH | 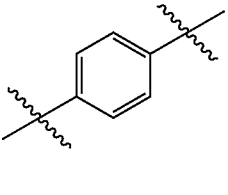 [SMILES: *c1ccc(*)cc1] | 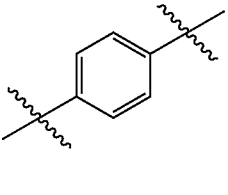 [SMILES: *c1ccc(*)cc1] | 1 | 0 | 2 |
| 4 | H | H | I | H | H | O | NH | NHC(S)NH | 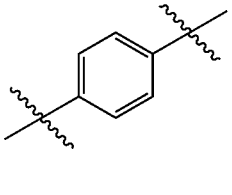 [SMILES: *c1ccc(*)cc1] | 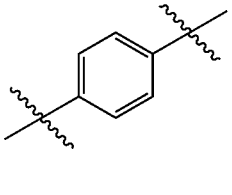 [SMILES: *c1ccc(*)cc1] | 1 | 0 | 2 |

TABLE 3-continued

Formula III

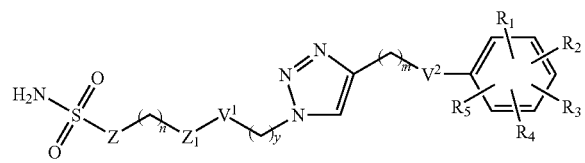

| Compound # | R1 | R2 | R3 | R4 | R5 | V1 | V2 | W1 | Z | Z1 | m | n | y |
|---|---|---|---|---|---|---|---|---|---|---|---|---|---|
| 5 | H | H | I | H | H | O—(CH₂CH₂O)₂ | O | NHC(S)NH | 1,4-phenylene | 1,4-phenylene | 1 | 1 | 2 |
| 6 | H | H | I | H | H | OCH₂CH₂O | O—(CH₂CH₂O)₂ | NHC(S)NH | 1,3-phenylene | 1,4-phenylene | 1 | 2 | 2 |
| 7 | H | H | I | H | H | OCH₂CH₂O | NH | NH | 1,3-phenylene | 1,4-phenylene | 1 | 0 | 2 |
| 8 | H | H | I | H | F | O | O—(CH₂CH₂O)₃ | NH | 1,3-phenylene | 1,4-phenylene | 1 | 0 | 2 |
| 9 | H | H | I | H | H | NH | O—(CH₂CH₂O)₃ | NHC(O)NH | 1,3-phenylene | 1,4-phenylene | 1 | 0 | 2 |
| 10 | H | H | I | H | H | O | O—(CH₂CH₂O)₂ | NHC(S)NH | 1,3-phenylene | 1,4-phenylene | 1 | 0 | 3 |
| 11 | H | H | I | H | H | O | O—(CH₂CH₂O)₂ | NHC(S)NH | 1,3-phenylene | 1,4-phenylene | 1 | 0 | 2 |
| 12 | H | H | I | H | H | O | OCH₂CH₂O | NHC(S)NH | 1,4-phenylene | 1,4-phenylene | 1 | 0 | 2 |

TABLE 3-continued

Formula III

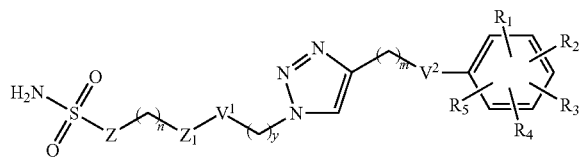

| Compound # | R1 | R2 | R3 | R4 | R5 | V1 | V2 | W1 | Z | Z1 | m | n | y |
|---|---|---|---|---|---|---|---|---|---|---|---|---|---|
| 13 | H | H | I | H | H | O | NH | NHC(S)NH | 1,4-phenylene | 1,4-phenylene | 1 | 0 | 3 |
| 14 | F | H | I | H | H | O | O—(CH$_2$CH$_2$O)$_2$ | NHC(S)NH | 1,3-phenylene | 1,4-phenylene | 1 | 0 | 3 |
| 15 | F | H | I | H | H | O | O—(CH$_2$CH$_2$O)$_2$ | NHC(S)NH | 1,3-phenylene | 1,4-phenylene | 1 | 0 | 2 |
| 16 | F | H | I | H | H | O | OCH$_2$CH$_2$O | NHC(S)NH | 1,4-phenylene | 1,4-phenylene | 1 | 0 | 2 |
| 17 | F | H | I | H | H | O | NH | NHC(S)NH | 1,4-phenylene | 1,4-phenylene | 1 | 0 | 3 |
| 18 | F | H | I | H | H | O | O—(CH$_2$CH$_2$O)$_2$ | NHC(S)NH | thiadiazole | 1,4-phenylene | 1 | 0 | 2 |
| 19 | F | H | I | H | H | O | OCH$_2$CH$_2$O | NHC(S)NH | thiadiazole | 1,4-phenylene | 1 | 0 | 2 |

TABLE 3-continued

Formula III

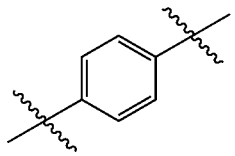 [SMILES: *c1ccc(*)cc1]

| Compound # | R1 | R2 | R3 | R4 | R5 | V1 | V2 | W1 | Z | Z1 | m | n | y |
|---|---|---|---|---|---|---|---|---|---|---|---|---|---|
| 20 | F | H | I | H | H | O | NH | NHC(S)NH | thiadiazole | *p*-phenylene | 1 | 0 | 3 |

Note:
In a preferred embodiment of the invention, the thiadiazole is preferably a 1,3,4-thiadiazole with the 2-position of the thiadiazole being linked to the rest of the molecule bearing the sulfonamide group and the 5-position of the thiadiazole being linked to the rest of the molecule bearing the substituted phenyl group.

TABLE 4

Formula IV

| Compound # | R1 | R2 | R3 | R4 | R5 | V1 | Z | n |
|---|---|---|---|---|---|---|---|---|
| 1 | H | H | I | H | H | O—(CH$_2$CH$_2$O)$_2$— | *p*-phenylene | 0 |
| 2 | H | H | I | H | H | O—(CH$_2$CH$_2$O)$_2$— | *p*-phenylene | 1 |
| 3 | H | H | I | H | H | O—(CH$_2$CH$_2$O)$_2$— | *p*-phenylene | 2 |
| 4 | H | H | I | H | H | O—(CH$_2$CH$_2$O)$_2$— | *p*-phenylene | 3 |

TABLE 4-continued
Formula IV
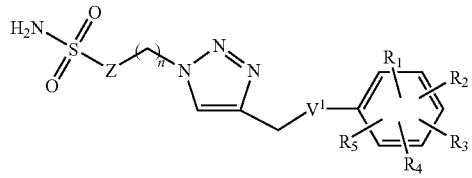
| Compound # | R1 | R2 | R3 | R4 | R5 | V1 | Z | n |
|---|---|---|---|---|---|---|---|---|
| 5 | H | H | I | H | H | NHC(S)NH | 1,4-phenylene | 0 |
| 6 | H | H | I | H | H | NHC(S)NH | 1,4-phenylene | 1 |
| 7 | H | H | I | H | H | NHC(S)NH | 1,4-phenylene | 2 |
| 8 | H | H | I | H | H | NHC(S)NH | 1,4-phenylene | 3 |
| 9 | H | H | I | H | H | O—(CH$_2$CH$_2$O)$_2$— | 1,3-phenylene | 0 |
| 10 | H | H | I | H | H | O—(CH$_2$CH$_2$O)$_2$— | 1,3-phenylene | 1 |
| 11 | H | H | I | H | H | O—(CH$_2$CH$_2$O)$_2$— | 1,3-phenylene | 2 |
| 12 | H | H | I | H | H | O—(CH$_2$CH$_2$O)$_2$— | 1,3-phenylene | 3 |

TABLE 4-continued

Formula IV

| Compound # | R1 | R2 | R3 | R4 | R5 | V1 | Z | n |
|---|---|---|---|---|---|---|---|---|
| 13 | H | H | I | H | H | NHC(S)NH | *m*-phenylene | 0 |
| 14 | H | H | I | H | H | NHC(S)NH | *m*-phenylene | 1 |
| 15 | H | H | I | H | H | NHC(S)NH | *m*-phenylene | 2 |
| 16 | H | H | I | H | H | O—(CH$_2$CH$_2$O)$_2$— | thiadiazole | 1 |
| 17 | H | H | I | H | H | O—(CH$_2$CH$_2$O)$_2$— | thiadiazole | 2 |
| 18 | H | H | I | H | H | O—(CH$_2$CH$_2$O)$_2$— | thiadiazole | 3 |
| 19 | H | H | I | H | H | NHC(S)NH | thiadiazole | 1 |
| 20 | H | H | I | H | H | NHC(S)NH | thiadiazole | 2 |
| 21 | H | H | I | H | H | NHC(S)NH | thiadiazole | 3 |

Note:
In a preferred embodiment of the invention, the thiadiazole is preferably a 1,3,4-thiadiazole with the 2-position of the thiadiazole being linked to the rest of the molecule bearing the sulfonamide group and the 5-position of the thiadiazole being linked to the rest of the molecule bearing the substituted phenyl group.

TABLE 5

Formula V

| Compound # | R1 | R2 | R3 | R4 | R7 | X | Z | m | n |
|---|---|---|---|---|---|---|---|---|---|
| 1 (MIP-1252) | H | H | I | H | Me | S | *p*-phenylene | 0 | 0 |
| 2 (MIP-1238) | H | H | I | H |  | S | *p*-phenylene | 0 | 0 |

TABLE 5-continued
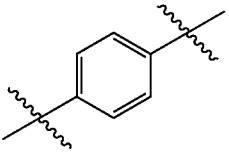 [SMILES: *c1ccc(*)cc1]
Formula V
| Compound # | R1 | R2 | R3 | R4 | R7 | X | Z | m | n |
|---|---|---|---|---|---|---|---|---|---|
| 3 | H | H | I | H | Et | S | 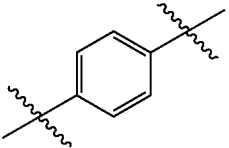 [SMILES: *c1ccc(*)cc1] | 0 | 0 |
| 4 | H | H | I | H | n-Pr | S | 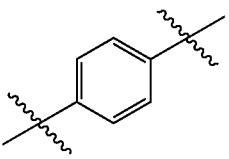 | 0 | 0 |
| 5 | H | I | H | H | | S | 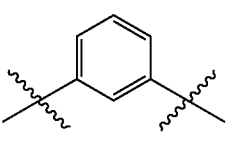 [SMILES: *c1cccc(*)c1] | 0 | 0 |
| 6 | H | I | H | H | Me | S | 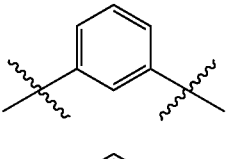 | 0 | 0 |
| 7 | H | I | H | F | Et | S | 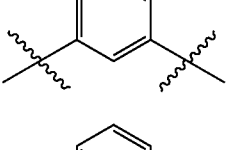 | 0 | 0 |
| 8 | H | H | I | H | | S | 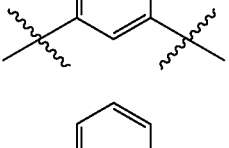 | 0 | 1 |
| 9 | H | H | I | H | Me | S | 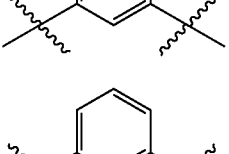 | 0 | 2 |
| 10 | H | H | I | H | Me | S |  | 0 | 3 |
| 11 | H | H | I | H | Me | S | | 1 | 0 |

TABLE 5-continued
Formula V
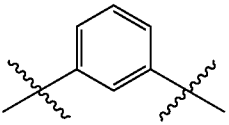 [SMILES: *c1cccc(*)c1]
| Compound # | R1 | R2 | R3 | R4 | R7 | X | Z | m | n |
|---|---|---|---|---|---|---|---|---|---|
| 12 | H | H | I | H | Me | S | 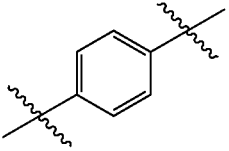 [SMILES: *c1ccc(*)cc1] | 1 | 1 |
| 13 | H | H | I | H | Me | S | 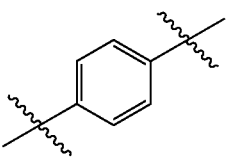 [SMILES: *c1ccc(*)cc1] | 0 | 0 |
| 14 | H | H | I | H |  | S | 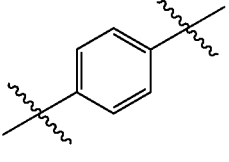 | 0 | 0 |
| 15 | H | H | I | H | Et | S | 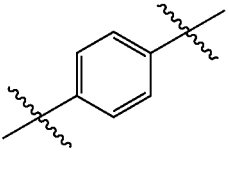 | 0 | 0 |
| 16 | H | H | I | H | n-Pr | S | 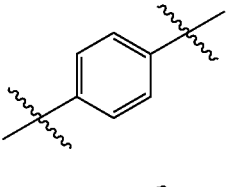 | 0 | 0 |
| 17 | H | I | H | H |  | S | 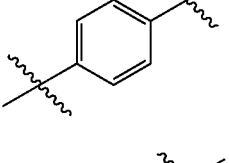 | 0 | 0 |
| 18 | H | I | H | H | Me | S | 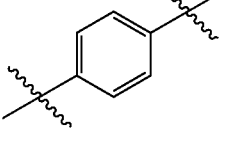 | 0 | 0 |
| 19 | H | H | I | H | Me | O |  | 0 | 0 |

TABLE 5-continued

Formula V

H₂N-S(=O)(=O)-Z-(CH)ₙ-NH-C(=X)-N(piperazine)N⁺(R7)-(CH)ₘ-pyridine(R1,R2,R3,R4)

| Compound # | R1 | R2 | R3 | R4 | R7 | X | Z | m | n |
|---|---|---|---|---|---|---|---|---|---|
| 20 | H | H | I | H |  | O | phenyl | 0 | 0 |
| 21 | H | H | I | H | Et | O | phenyl | 0 | 0 |
| 22 | H | H | I | H | n-Pr | O | phenyl | 0 | 0 |
| 23 | H | H | I | H | Me | S | thiadiazole | 0 | 0 |
| 24 | H | H | I | H | Et | S | thiadiazole | 0 | 0 |
| 25 | H | H | I | H | n-Pr | S | thiadiazole | 0 | 0 |

Note:
In a preferred embodiment of the invention, the thiadiazole is preferably a 1,3,4-thiadiazole with the 2-position of the thiadiazole being linked to the rest of the molecule bearing the sulfonamide group and the 5-position of the thiadiazole being linked to the rest of the molecule bearing the substituted phenyl group.

Example 47

In Vitro Screening

Figure 2:
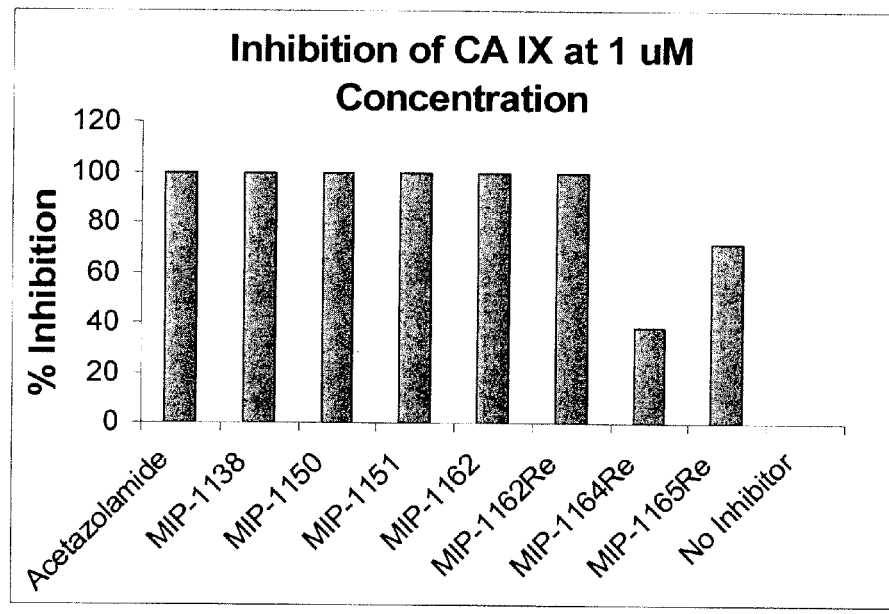
FIG. 2 is a graph illustrating inhibition of CA IX activity by some compounds in accordance with several embodiments of the present invention.
Figure 3:
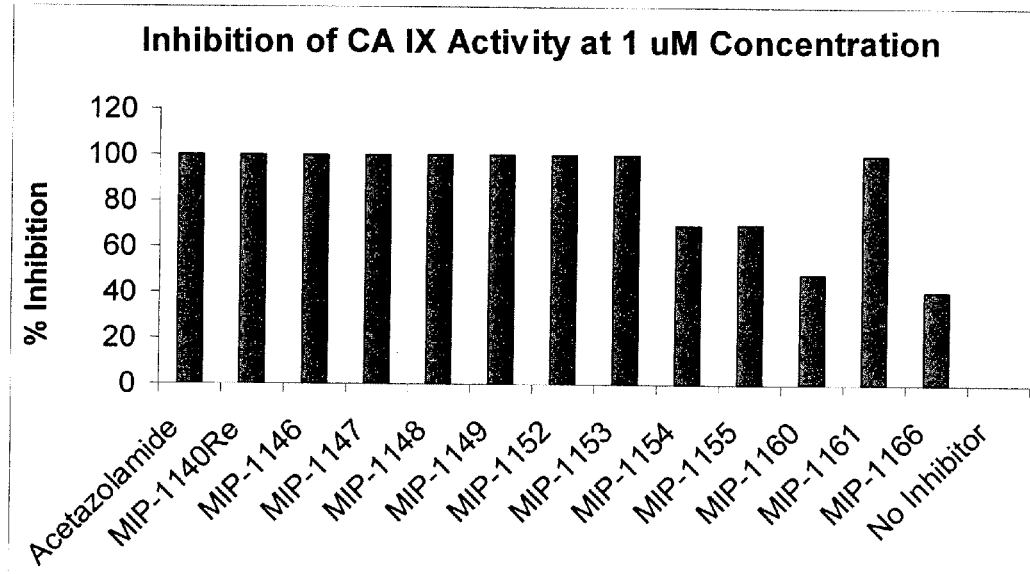
FIG. 3 is a graph illustrating inhibition of CA IX activity by some compounds in accordance with several embodiments of the present invention.
Figure 4A:
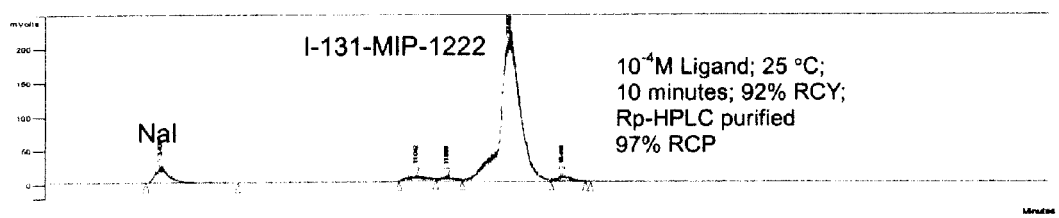
FIGS. 4A and 4B are graphs showing a radiochromatogram of crude $^{131}$I-MIP-1222 prepared from the stannane precursor (see, scheme immediately below) and an UV-Visible trace of MIP-1222.
Figure 4B:
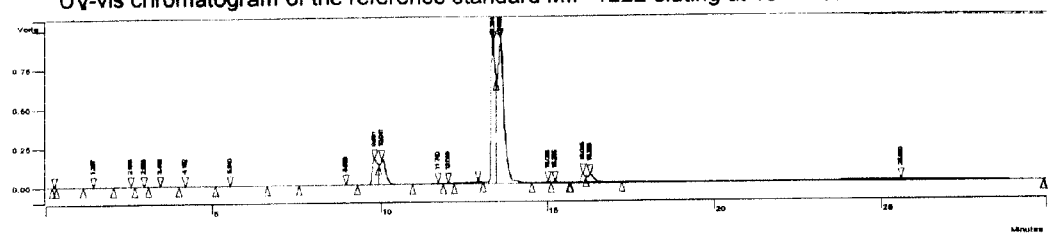
Figure 4C:
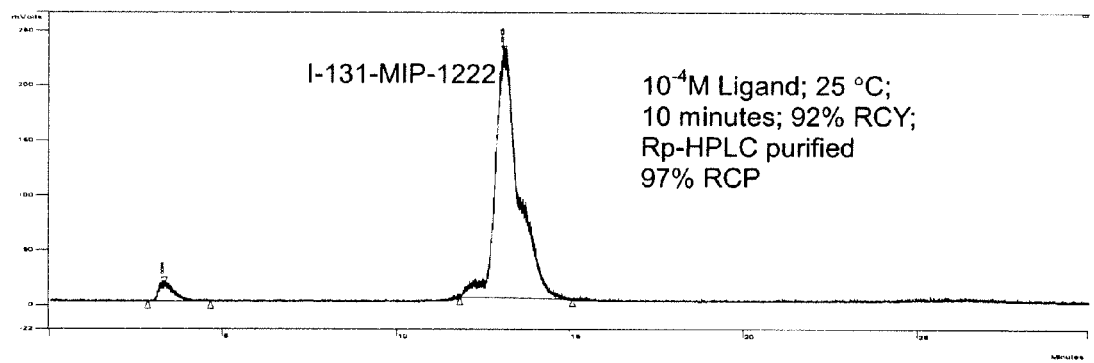
FIG. 4C is a graph showing a radiochromatogram of the HPLC-purified $^{131}$I-MIP-1222 at TOM+3 days in accordance with one embodiment of the present invention.

Test compounds were dissolved in either methanol or dimethylsulfoxide as a 100× stock. Carbonic anhydrase IX (67 nM) and test compound (1 µM) were incubated in assay buffer (300 µL of 9 mM Tris-HCl, 81 mM sodium chloride, pH 7.5) for 10 minutes at room temperature. The carbonic anhydrase substrate, 4-nitrophenylacetate (6.7 mM in acetonitrile), was then added to the mixture and incubated for 1 hour at room temperature. The carbonic anhydrase catalyzed hydrolysis of 4-nitrophenylacetate was monitored at 400 nm using a Wallac 1420 multilabel counter. Non-enzymatic hydrolysis was subtracted from the enzyme specific hydrolysis of 4-nitrophenylacetate. The carbonic anhydrase inhibitor, acetazolamide, was used as a positive control. FIGS. 2 and 3 illustrate the results expressed as percent inhibition of the reaction when no inhibitor was added.

From the foregoing it will be appreciated that, although specific embodiments of the invention have been described herein for purposes of illustration, various modifications may be made without deviating from the spirit and scope of the invention claimed in the claims.

What is claimed is:

1. A complex of formula I, its stereoisomer or pharmaceutically acceptable salt:

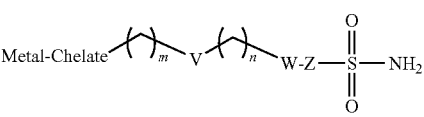

I wherein:

V is a bond, O, C=O, C(=X)—NH, a group of

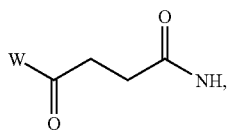

or a group of

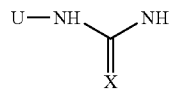

wherein X is O or S; U is a bond or a group of (O—CH$_2$—CH$_2$—O)$_p$—CH$_2$—CH$_2$ wherein p is an integer ranging from 1 to 3;

each W is independently a bond, O, or NH;

Z is an aromatic, bicyclic aromatic, heteroaromatic, bicyclic heteroaromatic or heterocyclic ring;

m is an integer ranging from 0 to 6;

n is an integer ranging from 0 to 6;

Metal represents a radionuclide selected from the group consisting of $^{99m}$Tc, $^{68}$Ga, $^{62}$Cu, $^{111}$In, $^{186}$Re, $^{188}$Re, $^{90}$Y, $^{212}$Bi, $^{211}$At, $^{89}$Sr, $^{166}$Ho, $^{153}$Sm, $^{67}$Cu, $^{64}$Cu, $^{100}$Pd, $^{212}$Pb, $^{109}$Pd, $^{68}$Ga, $^{94}$Tc, $^{105}$Rh, $^{95}$Ru, $^{177}$Lu, and $^{170}$Lu; and Chelate represents a chelating moiety that coordinates with said radionuclide to form said complex, and the Chelate is selected from the group consisting of tetra-azacyclododecanetetra-acetic acid (DOTA), diethylenetriaminepentaacetic acid (DTPA), bis(pyridin-2-ylmethyl)amine (DPA), quinolinemethylamino acetic acid (QAA), bis(isoquinolinemethyl)amine, bis(quinolinemethyl)amine (DQA), pyridine-2-ylmethylamino acetic acid (PAMA), isoquinolin-3-ylmethylamino acetic acid, bis(thiazol-2-ylmethyl)amine (DTK), and thiazol-2-ylmethylamino acetic acid (MTMA), bis(N-carboxymethylimidazoylamine) (DCMI), bis(N-1,1-dimethoxyethylimidazoylamine) (DMEI), bis(N-methylimidazoylamine) (DMI) and bis(N-hydroxyethylimidazoylamine) (DHI).

2. The complex of claim 1 wherein said radionuclide is selected from the group consisting of $^{99m}$Tc, $^{186}$Re, $^{188}$Re, $^{90}$Y, $^{64}$Cu, $^{177}$Lu, $^{68}$Ga and $^{111}$In.

3. The complex of claim 1 wherein said radionuclide is gamma emitting or positron emitting.

4. A method of imaging tissue of a mammal which expresses CA IX comprising administering to said mammal an effective amount of a complex or compound selected from the group consisting of formulae I, II, III, IV and V, its stereoisomer or pharmaceutically acceptable salt:

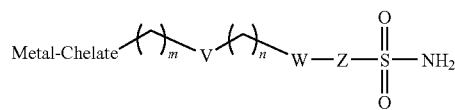

(I)

wherein in formula I:

V is a bond, O, C=O, C(=X)—NH, a group of

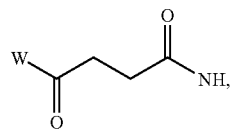

or a group of

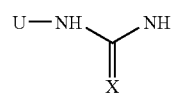

wherein X is O or S; U is a bond or a group of (O—CH$_2$—CH$_2$—O)$_p$—CH$_2$—CH$_2$ wherein p is an integer ranging from 1 to 3;

each W is independently a bond, O, or NH;

Z is an aromatic, bicyclic aromatic, heteroaromatic, bicyclic heteroaromatic or heterocyclic ring;

m is an integer ranging from 0 to 6;

n is an integer ranging from 0 to 6;

Metal represents a radionuclide selected from the group consisting of $^{99m}$Tc, $^{68}$Ga, $^{62}$Cu, $^{111}$In, $^{186}$Re, $^{188}$Re, $^{90}$Y, $^{212}$Bi, $^{211}$At, $^{89}$Sr, $^{166}$Ho, $^{153}$Sm, $^{67}$Cu, $^{64}$Cu, $^{100}$Pd, $^{212}$Pb, $^{109}$Pd, $^{67}$Ga, $^{94}$Tc, $^{105}$Rh, $^{95}$Ru, $^{177}$Lu, and $^{170}$Lu; and Chelate represents a chelating moiety that coordinates with said radionuclide to form said complex, and the Chelate is selected from the group consisting of tetra-azacyclododecanetetra-acetic acid (DOTA), diethylenetriaminepentaacetic acid (DTPA), bis(pyridin-2-ylmethyl)amine (DPA), quinolinemethylamino acetic acid (QAA), bis(isoquinolinemethyl)amine, bis(quinolinemethyl)amine (DQA), pyridine-2-ylmethylamino acetic acid (PAMA), isoquinolin-3-ylmethylamino acetic acid, bis(thiazol-2-ylmethyl)amine (DTK), and thiazol-2-ylmethylamino acetic acid (MTMA), bis(N-carboxymethylimidazoylamine) (DCMI), bis(N-1,1-dimethoxyethylimidazoylamine) (DMEI), bis(N-methylimidazoylamine) (DMI) and bis(N-hydroxyethylimidazoylamine) (DHI);

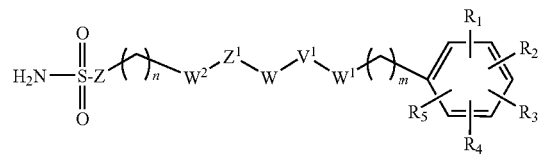

(II)

wherein in formula II:

$V^1$ is selected from the group consisting of a bond, O, NH, O—(CH$_2$—CH$_2$—O)$_q$, a group of

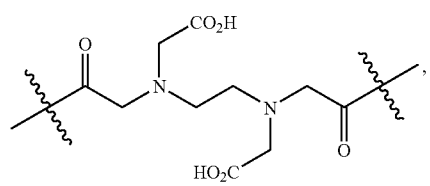

a group of CHR$_6$—CO and CHR$_6$—CO—NH—CHR$_6$—CO wherein R$_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

W is a bond, O, or NH;

$W^1$ and $W^2$ are independently a bond, NH, C=X, or a group of

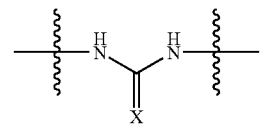

wherein X is O or S;
Z is an aromatic, bicyclic aromatic, heteroaromatic, bicyclic heteroaromatic or heterocyclic ring;
$Z^1$ is a bond, aromatic, bicyclic aromatic, heteroaromatic, bicyclic heteroaromatic or heterocyclic ring;
m is an integer ranging from 0 to 8;
n is an integer ranging from 0 to 8;
q is an integer ranging from 1 to 6; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected;

(III)

wherein in formula III:
$V^1$ and $V^2$ are independently selected from the group consisting of a bond, O, NH, O—$(CH_2—CH_2—O)_q$, a group of a group of $CHR_6$—CO or $CHR_6$—CO—NH—$CHR_6$—CO wherein $R_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;
$W^1$ is a bond, NH, C=X, or a group of wherein X is O or S;
Z is an aromatic, bicyclic aromatic, heteroaromatic, bicyclic heteroaromatic or heterocyclic ring;
$Z^1$ is a bond, aromatic, bicyclic aromatic, heteroaromatic, bicyclic heteroaromatic or heterocyclic ring;
m is an integer ranging from 0 to 8;
n is an integer ranging from 0 to 8;
q is an integer ranging from 1 to 6;
y is an integer ranging from 0 to 6; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected;

(IV)

wherein in formula IV:
$V^1$ is selected from the group consisting of a bond, O, NH, O—$(CH_2—CH_2—O)_q$, a group of a group of $CHR_6$—CO or $CHR_6$—CO—NH—$CHR_6$—CO wherein $R_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;
Z is an aromatic, bicyclic aromatic, heteroaromatic, bicyclic heteroaromatic or heterocyclic ring;
n is an integer ranging from 0 to 8;
q is an integer ranging from 1 to 6; and
$R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected; and (V)

wherein in formula V:
X is O or S;
m is an integer ranging from 0 to 8;
n is an integer ranging from 0 to 8;
$R_1$, $R_2$, $R_3$, and $R_4$ are independently selected from the group consisting of hydrogen, carboxyl, halogen, alkyl, alkoxy, and substituted or unsubstituted amino wherein at least one halogen is selected; and
$R_7$ is H or lower alkyl.

5. The method of claim 4 further comprising determining the level of CA IX in said tissue.

6. The method of claim 4 further comprising monitoring the changes of the level of CA IX in said tissue over a period of time.

7. The method of claim 4 wherein said administration is carried out intravenously.

8. A method of treating a mammal suffering a disease which is characterized by over expression of CA IX, the method comprising administering to said mammal a therapeutically effective amount of a complex or compound selected from the group consisting of formulae I, II, III, IV and V, its stereoisomer or pharmaceutically acceptable salt:

$$\text{Metal-Chelate} \mathrm{-\!\!\!\!-\!\!\!\!\{\!-\!\}_{\!m}\!\!\!-V\!\!-\!\!\{\!-\!\}_{\!n}\!\!\!-W\!\!-\!\!Z\!\!-\!\!\overset{\overset{O}{\|}}{\underset{\underset{O}{\|}}{S}}\!\!-\!\!NH_2} \quad (I)$$

wherein in formula I:
V is a bond, O, C=O, C(=X)—NH, a group of

[structure: W—C(=O)—CH₂CH₂—C(=O)—NH]

or a group of

[structure: U—NH—C(=X)—NH]

wherein X is O or S; U is a bond or a group of (O—CH₂—CH₂—O)$_p$—CH₂—CH₂ wherein p is an integer ranging from 1 to 3;
  each W is independently a bond, O, or NH;
  Z is an aromatic, bicyclic aromatic, heteroaromatic, bicyclic heteroaromatic or heterocyclic ring;
  m is an integer ranging from 0 to 6;
  n is an integer ranging from 0 to 6;
  Metal represents a radionuclide selected from the group consisting of $^{99m}$Tc, $^{68}$Ga, $^{62}$Cu, $^{111}$In, $^{186}$Re, $^{188}$Re, $^{90}$Y, $^{212}$Bi, $^{211}$At, $^{89}$Sr, $^{166}$Ho, $^{153}$Sm, $^{67}$Cu, $^{64}$Cu, $^{100}$Pd, $^{212}$Pb, $^{109}$Pd, $^{67}$Ga, $^{94}$Tc, $^{105}$Rh, $^{95}$Ru, $^{177}$Lu, and $^{170}$Lu; and
  Chelate represents a chelating moiety that coordinates with said radionuclide to form said complex, and the Chelate is selected from the group consisting of tetra-azacyclododecanetetra-acetic acid (DOTA), diethylenetriaminepentaacetic acid (DTPA), bis(pyridin-2-ylmethyl)amine (DPA), quinolinemethylamino acetic acid (QAA), bis(isoquinolinemethyl)amine, bis(quinolinemethyl)amine (DQA), pyridine-2-ylmethylamino acetic acid (PAMA), isoquinolin-3-ylmethylamino acetic acid, bis(thiazol-2-ylmethyl)amine (DTK), and thiazol-2-ylmethylamino acetic acid (MTMA), bis(N-carboxymethylimidazoylamine) (DCMI), bis(N-1,1-dimethoxyethylimidazoylamine) (DMEI), bis(N-methylimidazoylamine) (DMI) and bis(N-hydroxyethylimidazoylamine) (DHI);

$$\mathrm{H_2N\!\!-\!\!\overset{\overset{O}{\|}}{\underset{\underset{O}{\|}}{S}}\!\!-\!\!Z\!\!-\!\!\{\!-\!\}_{\!n}\!\!-\!\!W^2\!\!-\!\!Z^1\!\!-\!\!W\!\!-\!\!V^1\!\!-\!\!\{\!-\!\}_{\!m}\!\!-\!\!\text{Ar}(R_1,R_2,R_3,R_4,R_5)} \quad (II)$$

wherein in formula II:
V¹ is selected from the group consisting of a bond, O, NH, O—(CH₂—CH₂—O)$_q$, a group of

[structure: N,N'-bis(carboxymethyl)ethylenediamine-N,N'-diacetyl linker]

a group of CHR₆—CO and CHR₆—CO—NH—CHR₆—CO
wherein R₆ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;
  W¹ is a bond, NH, C=X, or a group of

[structure: —NH—C(=X)—NH—]

wherein X is O or S;
  Z is an aromatic, bicyclic aromatic, heteroaromatic, bicyclic heteroaromatic or heterocyclic ring;
  Z¹ is a bond, aromatic, bicyclic aromatic, heteroaromatic, bicyclic heteroaromatic or heterocyclic ring;
  m is an integer ranging from 0 to 8;
  n is an integer ranging from 0 to 8;
  q is an integer ranging from 0 to 6; and
  R₁, R₂, R₃, R₄ and R₅ are independently selected from the group consisting of hydrogen, carboxyl, halogen, alkyl, alkoxy, and substituted or unsubstituted amino wherein at least one halogen is selected;

$$\mathrm{H_2N\!\!-\!\!\overset{\overset{O}{\|}}{\underset{\underset{O}{\|}}{S}}\!\!-\!\!Z\!\!-\!\!\{\!-\!\}_{\!n}\!\!-\!\!W\!\!-\!\!Z^1\!\!-\!\!V^2\!\!-\!\!\text{triazole}\!\!-\!\!\{\!-\!\}_{\!m}\!\!-\!\!V^1\!\!-\!\!\text{Ar}(R_1..R_5)} \quad (III)$$

wherein in formula III:
V¹ and V² are independently selected from the group consisting of a bond, O, NH, O—(CH₂—CH₂—O)$_q$, a group of

[structure: N,N'-bis(carboxymethyl)ethylenediamine-N,N'-diacetyl linker]

a group of CHR₆—CO or CHR₆—CO—NH—CHR₆—CO
wherein R₆ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

$W^1$ is a bond, NH, C=X, or a group of

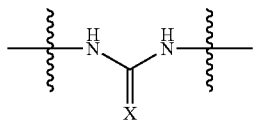

wherein X is O or S;

Z is an aromatic, bicyclic aromatic, heteroaromatic, bicyclic heteroaromatic or heterocyclic ring;

$Z^1$ is a bond, aromatic, bicyclic aromatic, heteroaromatic, bicyclic heteroaromatic or heterocyclic ring;

m is an integer ranging from 0 to 8;

n is an integer ranging from 0 to 8;

q is an integer ranging from 1 to 6;

y is an integer ranging from 0 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected; and

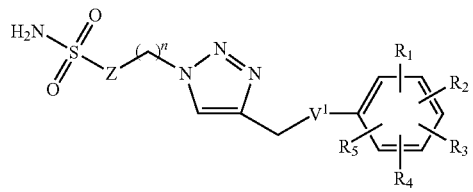

(IV)

wherein in formula IV:

$V^1$ is selected from the group consisting of a bond, O, NH, O—(CH$_2$—CH$_2$—O)$_q$, a group of

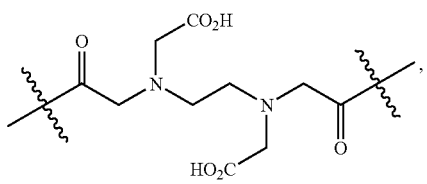 [SMILES: *C(=O)CN(CCN(CC(*)=O)CC(=O)O)CC(=O)O]

a group of CHR$_6$—CO or CHR$_6$—CO—NH—CHR$_6$—CO wherein R$_6$ is lower alkyl substituted with carboxylic acid, sulfonic acid, sulfuric acid, phosphonic acid, phosphinic acid, phosphoric acid, amine, guanidine, amidine or N-containing heterocycle, and combinations thereof;

Z is an aromatic, bicyclic aromatic, heteroaromatic, bicyclic heteroaromatic or heterocyclic ring;

n is an integer ranging from 0 to 8;

q is an integer ranging from 1 to 6; and $R_1$, $R_2$, $R_3$, $R_4$ and $R_5$ are independently selected from the group consisting of hydrogen, carboxyl, halogen, alkyl, alkoxy, and substituted or unsubstituted amino wherein at least one halogen is selected; and

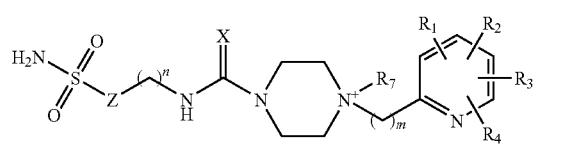

(V)

wherein in formula V:

X is O or S;

m is an integer ranging from 0 to 8;

n is an integer ranging from 0 to 8;

$R_1$, $R_2$, $R_3$, and $R_4$ are independently selected from the group consisting of hydrogen, carboxyl, halogen, alkyl, alkoxy, and substituted or unsubstituted amino wherein at least one halogen is selected; and $R_7$ is H or lower alkyl.

9. The complex of claim 2 wherein said radionuclide is selected from the group consisting of $^{99m}$Tc, $^{186}$Re, and $^{188}$Re.

* * * * *